United States Patent
Scarborough et al.

(10) Patent No.: US 7,294,635 B2
(45) Date of Patent: Nov. 13, 2007

(54) SUBSTITUTED ISOQUINOLINONES

(75) Inventors: Robert M. Scarborough, Half Moon Bay, CA (US); Kim A. Kane-MaGuire, Belmont, CA (US); Charles K. Marlowe, Redwood City, CA (US); Mark S. Smyth, Foster City, CA (US); Xiaoming Zhang, Sunnyvale, CA (US)

(73) Assignee: Portola Pharmaceuticals, Inc., S. San Francisco, CA (US)

( * ) Notice: Subject to any disclaimer, the term of this patent is extended or adjusted under 35 U.S.C. 154(b) by 499 days.

(21) Appl. No.: 10/956,006

(22) Filed: Sep. 29, 2004

(65) Prior Publication Data

US 2005/0113399 A1 May 26, 2005

Related U.S. Application Data

(60) Provisional application No. 60/508,402, filed on Oct. 3, 2003.

(51) Int. Cl.
*C07D 407/04* (2006.01)
*A61K 31/506* (2006.01)
*A61K 31/4709* (2006.01)

(52) U.S. Cl. ............... 514/275; 514/309; 544/331; 546/141

(58) Field of Classification Search ............ 544/331; 546/141; 514/275, 309
See application file for complete search history.

(56) References Cited

U.S. PATENT DOCUMENTS

2002/0077486 A1 6/2002 Scarborough et al.

FOREIGN PATENT DOCUMENTS

| WO | WO 99/05144 A1 | 2/1999 |
| WO | WO 99/36425 A1 | 7/1999 |
| WO | WO 01/57037 A1 | 8/2001 |

OTHER PUBLICATIONS

Yin, J. and S.L. Buchwald, "Palladium catalyzed intermolecular coupling of aryl halides and amides." *Org. Lett.*, vol. 2, pp. 1101-1104 (2000).

Berge, S.M., et al, "Pharmaceutical salts." *J. Pharmaceut. Sci.*, vol. 66, No. 1., pp. 1-19 (1977).

Fratantoni J.C. and B.J. Poindexter, "Measuring platelet aggregation with microplate reader. A new technical approach to platelet aggregation studies." *Am. J. Clin. Pathol.*, vol. 94, No. 5; pp. 613-617 (1990).

Fredholm, B.B. et al., "Towards a revised nomenclature for P1 and P2 receptors." *Trends Pharmacol. Sci.*, vol. 18, No. 3; pp. 79-82 (1997).

Hechler, B. et al., "The P2Y1 receptor is necessary for adenosine 5'-diphosphate-induced platelet aggregation." *Blood*, vol. 92, No. 1; pp. 152-159 (1998).

Hollopeter, G. et. al., "Identification of the platelet ADP receptor targeted by antithrombotic drugs." *Nature*, vol. 409, No. 6817; pp. 202-207 (2001).

Humphries et al., "A novel series of P2T purinoceptor antagonists: definition of the role of ADP in arterial thrombosis." *Trends Pharmacol. Sci.*, vol. 16, No. 6; pp. 179-181 (1995).

Ingall, A.H. et al., "Antagonists of the platelet P2T receptor: a novel approach to antithrombotic therapy." *J. Med. Chem.*, vol. 42, No. 2, pp. 213-220 (1999).

Jantzen, H.M. et al., "Evidence for two distinct G-protein-coupled ADP receptors mediating platelet activation." *Thromb. Haemost.*, vol. 81, No. 1; pp. 111-117 (1999).

King, B.F. et al., "Metabotropic receptors for ATP and UTP: exploring the correspondence between native and recombinant nucleotide receptors." *Trends Pharmacol. Sci.*, vol. 19, No. 12; pp. 506-514 (1998).

Kunapuli, S.P. and J.L. Daniel, "P2 receptor subtypes in the cardiovascular system." *Biochem. J.*, vol. 336, No. 3; pp. 513-523 (1998).

Kunapuli, S.P., "Multiple P2 receptor subtypes on platelets: a new interpretation of their function." *Trends Pharmacol. Sci.*, vol. 19, No. 10; pp. 391-394 (1998).

Mills, D.C.B.. "ADP receptors on platelets." *Thromb. Haemost.*, vol. 76, No. 6, pp. 835-856 (1996).

Quinn, M.J. and D.J. Fitzgerald, "Ticlopidine and clopidogrel." *Circulation*, vol. 100, No. 15; pp. 1667-1672 (1999).

*Primary Examiner*—Zinna N. Davis
(74) *Attorney, Agent, or Firm*—Townsend and Townsend and Crew LLP

(57) ABSTRACT

Isoquinolinone compounds are provided that are useful for the inhibition of ADP-platelet aggregation, particularly in the treatment of thrombosis and thrombosis related conditions or disorders.

30 Claims, No Drawings

SUBSTITUTED ISOQUINOLINONES

CROSS-REFERENCES TO RELATED APPLICATIONS

This application claims the benefit of Provisional Application Ser. No. 60/508,402, filed Oct. 3, 2003, the disclosure of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) *Thromb. Hemost.* 76:835-856). Therefore, platelet ADP receptors are members of the family of P2 receptors activated by purine and/or pyrimidine nucleotides (King, B. F., Townsend-Nicholson, A. & Burnstock, G. (1998) *Trends Pharmacol. Sci.* 19:506-514).

Recent pharmacological data using selective antagonists suggests that ADP-dependent platelet aggregation requires activation of at least two ADP receptors (Kunapuli, S. P. (1998), *Trends Pharmacol. Sci.* 19:391-394; Kunapuli, S. P. & Daniel, J. L. (1998) *Biochem. J.* 336:513-523; Jantzen, H. M. et al. (1999) *Thromb. Hemost.* 81:111-117). One receptor appears to be identical to the cloned P2Y₁ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor (P2Y$_{12}$) has recently been reported (Hollopeter, G. et. al. (2001) *Nature* 409:202-207). Based on its pharmacological and signaling properties this receptor has been previously termed P2Y$_{ADP}$ (Fredholm, B. B. et al. (1997) *TIPS* 18:79-82), P2T$_{AC}$ (Kunapuli, S. P. (1998), *Trends Pharmacol. Sci.* 19:391-394) or P2Ycyc (Hechler, B. et al. (1998) Blood 92, 152-159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) *Circulation* 100: 1667-1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), *Trends Pharmacol. Sci.* 16, 179; Ingall, A. H. et al. (1999) J. Med. Chem. 42, 213-230). Novel triazolo[4,5-d]pyrimidine compounds have been disclosed as P$_{2T}$—antagonists (WO 99/05144). Tricyclic compounds as platelet ADP receptor inhibitors have also been disclosed in WO 99/36425. The target of these antithrombotic compounds appears to be the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

BRIEF SUMMARY OF THE INVENTION

In view of the above, the present invention provides, in one aspect, compounds that are specifically substituted isoquinolinones. The compounds are represented by the formula:

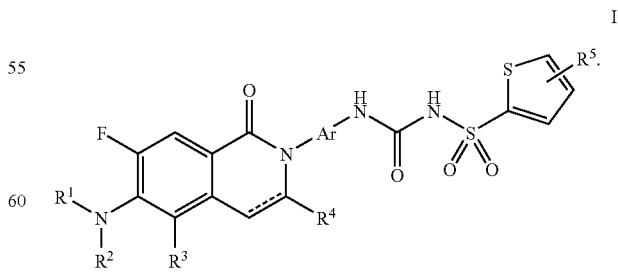

I

With respect to formula I, the dotted line represents an optional double bond; the symbol $R^1$ represents $C_{1-6}$ alkyl, $C_{1-6}$ haloalkyl, $C_{3-5}$ cycloalkyl, $C_{3-5}$ cycloalkyl-alkyl or benzyl; and the symbol $R^2$ represents H, $C_{1-6}$ alkyl or $C_{1-6}$ haloalkyl. The symbol $R^3$ represents H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, cyano or —C(O)$R^{3a}$, wherein $R^{3a}$ is H, hydroxy, $C_{1-6}$ alkyl, $C_{1-6}$ alkoxy, amino, $C_{1-6}$ alkylamino and di-$C_{1-6}$ alkylamino; and $R^4$ represents H or $C_{1-6}$ alkyl.

Turning next to the substituents on the thiophene ring, $R^5$ represents H, halogen, $C_{1-6}$ alkyl, $C_{2-6}$ alkenyl, $C_{2-6}$ alkynyl, $C_{1-6}$ haloalkyl, $C_{1-6}$ alkoxy, cyano or —C(O)$R^{5a}$, wherein $R^{5a}$ represents $C_{1-6}$ alkoxy, amino, $C_{1-6}$ alkylamino and di-$C_{1-6}$ alkylamino.

The symbol Ar represents an aromatic ring selected from benzene, pyridine and pyrimidine, each of which is optionally substituted with from 1-2 $R^6$ substituents, wherein each $R^6$ is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, amino, $C_{1-6}$ alkylamino, di-$C_{1-6}$ alkylamino, —C(O)$R^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_m$N(R$^{6b}$)$_2$, wherein the subscript m is an integer of from 1 to 3, each $R^{6a}$ is independently selected from H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine or piperidine ring.

The present invention further provides pharmaceutically acceptable salts of the above compounds, as well as pharmaceutical compositions containing those compounds.

In other aspects, the present invention provides methods of treating thrombosis and thrombosis related conditions or disorders.

BRIEF DESCRIPTION OF THE DRAWINGS

Not applicable.

DETAILED DESCRIPTION OF THE INVENTION

Definitions

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. When "cycloalkyl" is used in combination with "alkyl", as in $C_{3-5}$ cycloalkyl-alkyl, the cycloalkyl portion is meant to have from three to five carbon atoms, while the alkyl portion is an alkylene moiety having from one to three carbon atoms (e.g., —CH$_2$—, —CH$_2$CH$_2$— or —CH$_2$CH$_2$CH$_2$—).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. For brevity, the term $C_{1-6}$alkylamino is meant to include straight chain, branched or cyclic alkyl groups or combinations thereof, such as methyl, ethyl, 2-methylpropyl, cyclobutyl and cyclopropylmethyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Exemplary aryl groups are phenyl, naphthyl, biphenyl and the like. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers (e.g., separate enantiomers) are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

DESCRIPTION OF THE EMBODIMENTS

Compounds

In view of the above, the present invention provides, in one aspect, compounds that are specifically substituted isoquinolinones. The compounds are represented by the formula:

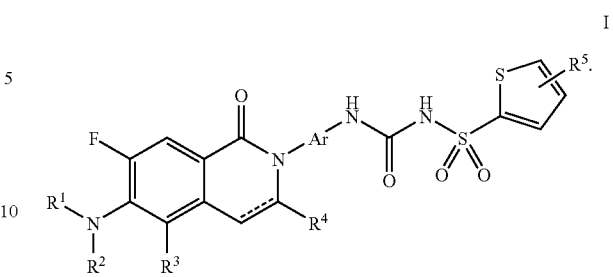

Turning first to the symbols $R^1$ through $R^4$, the symbol $R^1$ represents $C_{1-6}$ alkyl, $C_{1-6}$ haloalkyl, $C_{3-5}$ cycloalkyl, $C_{3-5}$ cycloalkyl-alkyl or benzyl. For the terms $C_{3-5}$ cycloalkyl-alkyl and (as used below) $C_{3-5}$ cycloalkyl-alkoxy, the alkyl or alkoxy portions respectively are meant to have from one to three carbon atoms, exclusive of the carbon atoms used in the cycloalkyl portion. For example, $C_{3-5}$ cycloalkyl-alkyl is meant to include cyclopropylmethyl, cyclopentylmethyl, 3-cyclobutylpropyl, 2-cylcopropylethyl, and the like. Similarly, $C_{3-5}$ cycloalkyl-alkoxy is meant to include cyclopropylmethoxy, cyclopentylmethoxy, 3-cyclobutylpropyloxy, 2-cylcopropylethoxy, and the like. Preferably, $R^1$ is $C_{1-6}$ alkyl, $C_{3-5}$ cycloalkyl, or $C_{3-5}$ cycloalkyl-alkyl. More preferably, $R^1$ is $C_{1-4}$ alkyl, $C_{3-5}$ cycloalkyl, or $C_{3-5}$ cycloalkyl-alkyl. Still more preferably, $R^1$ is $C_{1-4}$ alkyl, particularly $CH_3$ or $CH_2CH_3$ with $CH_3$ being the most preferred.

The symbol $R^2$ represents H, $C_{1-6}$ alkyl or $C_{1-6}$ haloalkyl. Preferably, $R^2$ is H or $C_{1-6}$ alkyl; more preferably H or $C_{1-4}$ alkyl. Still more preferably, $R^2$ is H or $CH_3$, with H being the most preferred.

The symbol $R^3$ represents H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, cyano or —C(O)$R^{3a}$, wherein $R^{3a}$ is selected from H, hydroxy, $C_{1-6}$ alkyl, $C_{1-6}$ alkoxy, amino, $C_{1-6}$ alkylamino and di- $C_{1-6}$ alkylamino. Preferably, $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$. More preferably, $R^3$ is H, $C_{1-4}$ alkyl, $C_{2-4}$ alkenyl, $C_{2-4}$ alkynyl, $C_{3-5}$ cycloalkyl, or $C_{3-5}$ cycloalkyl-alkyl.

The symbol $R^4$ represents H or $C_{1-6}$ alkyl. Preferably, $R^4$ is H or $C_{1-4}$ alkyl. More preferably, $R^4$ is H or $CH_3$.

Turning next to the substituents on the thiophene ring, $R^5$ represents H, halogen, $C_{1-6}$ alkyl, $C_{2-6}$ alkenyl, $C_{2-6}$ alkynyl, $C_{1-6}$ haloalkyl, $C_{1-6}$ alkoxy, cyano or —C(O)$R^{5a}$, wherein $R^{5a}$ represents $C_{1-6}$ alkoxy, amino, $C_{1-6}$ alkylamino and di-$C_{1-6}$ alkylamino. Preferably, $R^5$ is H, halogen, $C_{1-4}$ alkyl, $C_{2-4}$ alkenyl, $C_{2-4}$ alkynyl, $C_{1-4}$ haloalkyl, $C_{1-4}$ alkoxy, cyano or —C(O)$R^{5a}$. More preferably, $R^5$ is halogen, $C_{1-4}$ alkyl, $C_{1-4}$ haloalkyl, $C_{1-4}$ alkoxy, cyano, —C≡CH or —C(O)NH$_2$. Still more preferably, $R^5$ is halogen or $C_{1-4}$ alkyl. Most preferably, $R^5$ is chloro, and is attached to the 5-position of the thienyl ring.

The symbol Ar represents an aromatic ring selected from benzene, pyridine and pyrimidine, each of which is optionally substituted with from 1-2 $R^6$ substituents, wherein each $R^6$ is independently selected from halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, amino, $C_{1-6}$ alkylamino, di-$C_{1-6}$ alkylamino, —C(O)$R^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_m$N(R$^6$)$_2$, wherein the subscript m is an integer of from 1 to 3, each $R^{6a}$ is independently selected from H, hydroxy, $C_{1-6}$ alkyl, $C_{1-6}$ alkoxy, amino, $C_{1-6}$ alkylamino and di-$C_{1-6}$ alkylamino, and each $R^{6b}$ is independently selected from H, $C_{1-4}$ alkyl and $C_{1-4}$ alkanoyl, and optionally, two $R^{6b}$ groups attached to nitrogen are combined with the nitrogen atom to form an azetidine, pyrrolidine or piperidine ring. Each of the aromatic rings (optionally substituted) is a separate and preferred embodiment of the present invention.

The dotted line in Formula I represents an optional double bond. In most embodiments, the double bond is present, and preferred. In some embodiments, however, the double bond is not present, the remaining valences being filled with hydrogen atoms. As a result, the dotted line is meant to represent both of the following:

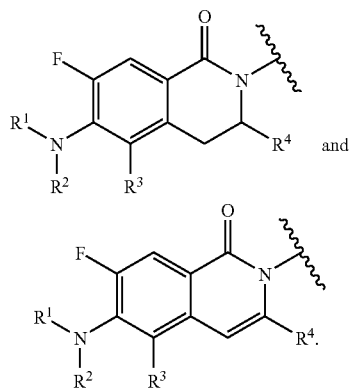

A number of particularly preferred embodiments are provided as formulae Ia, Ib and Ic.

In a first group of preferred embodiments, the compounds of the present invention have the formula:

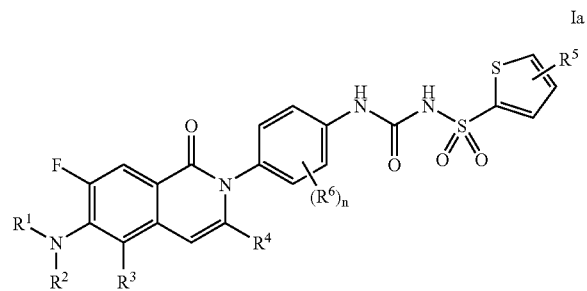

wherein each of $R^1$, $R^2$, $R^3$, $R^4$, $R^5$, and $R^6$ have the meanings provided above, and the subscript n is an integer of from 0 to 2, indicating the absence (n is 0) or presence (n is 1 or 2) of substituents that are independently selected from the groups provided above for $R^6$. Further preferred are those embodiments in which $R^6$, when present, occupy positions on the benzene ring that are adjacent to the carbon atom bearing the urea-sulfonyl (—NHC(O)NHS(O)$_2$—) component. Additionally, preferred components provided above with respect to the general formula I are also preferred for compounds of formula Ia.

In one group of preferred embodiments of formula Ia, n is an integer of from 0 to 2; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl. Still further preferred are those embodiments in which $R^1$ is $C_{1-4}$ alkyl; $R^4$ is H or CH$_3$; $R^5$ is halogen or $C_{1-4}$ alkyl; and each $R^6$ when present is selected from $C_{1-4}$ alkyl, —O(CH$_2$)$_m$OR$^{6b}$ and —O(CH$_2$)$_m$N(R$^{6b}$)$_2$. Even further preferred are those embodiments in which $R^1$ is methyl; $R^5$ is chloro, and is attached at the 5-position of the thienyl ring; and each $R^6$ when present is selected from CH$_3$, —OCH$_2$CH$_2$OH, —OCH$_2$CH$_2$OCH$_3$, —OCH$_2$OCH$_3$, —OCH$_2$CH$_2$OC(O)CH$_3$ and —O(CH$_2$)$_2$N(CH$_3$)$_2$. In separate, but preferred groups of embodiments, the subscript n is 0, or 1, or 2.

In a second group of preferred embodiments, the compounds of the present invention have the formula:

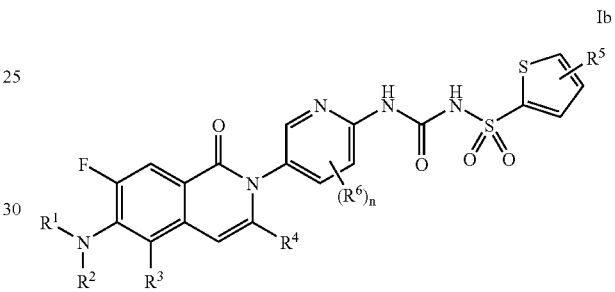

wherein each of $R^1$, $R^2$, $R^3$, $R^4$, $R^5$, and $R^6$ have the meanings provided above, and the subscript n is an integer of from 0 to 2, indicating the absence (n is 0) or presence (n is 1 or 2) of substituents that are independently selected from the groups provided above for $R^6$. Further preferred are those embodiments in which $R^6$, when present as a single substituent, occupies the 3-position on the pyridine ring (i.e., that position adjacent to the carbon atom bearing the urea-sulfonyl (—NHC(O)NHS(O)$_2$—) component). Additionally, preferred components provided above with respect to the general formula I are also preferred for compounds of formula Ib.

In one group of preferred embodiments of formula Ib, n is an integer of from 0 to 2; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^6$)$_2$ wherein the subscript m is 1 or 2 and each $R^{6b}$ is independently selected from the group consisting of H, $C_{1-4}$ alkyl and $C_{1-4}$ alkanoyl. Still further preferred are those embodiments in which $R^1$ is $C_{1-4}$ alkyl; $R^4$ is H or CH$_3$; $R^5$ is halogen or $C_{1-4}$ alkyl; and each $R^6$ when present is selected from $C_{1-4}$ alkyl, —O(CH$_2$)$_m$OR$^{6b}$ and —O(CH$_2$)$_m$N(R$^{6b}$)$_2$. Even further preferred are those embodiments in which $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or CH$_3$; $R^5$ is chloro and is attached at the 5-position of the thienyl ring; and $R^6$, when present is selected from $C_{1-4}$ alkyl, O(CH$_2$)$_m$ $OR^{6b}$ and —$O(CH_2)_mN(R^{6b})_2$ wherein the subscript m is 1 or 2 and each $R^{6b}$ is independently selected from H, $C_{1-4}$ alkyl and $C_{1-4}$ alkanoyl.

In still other embodiments, the compounds of the invention have the formula Ic:

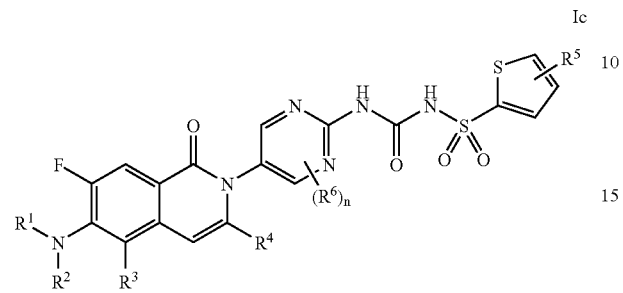

Ic wherein each of $R^1$, $R^2$, $R^3$, $R^4$, $R^5$, and $R^6$ have the meanings provided above, and the subscript n is an integer of from 0 to 2, indicating the absence (n is 0) or presence (n is 1 or 2) of substituents that are independently selected from the groups provided above for $R^6$. Preferred components provided above with respect to the general formula I are also preferred for compounds of formula Ic.

In one group of preferred embodiments of formula Ic, n is an integer of from 0 to 2; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —$C(O)R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —$CONH_2$; and $R^6$, when present is selected from the group consisting of $C_{1-4}$ alkyl, $C_{1-4}$ alkoxy, $C_{3-5}$ cycloalkyl-alkoxy, —$O(CH_2)_mOR^{6b}$ and —$O(CH_2)_mN(R^{6b})_2$ wherein the subscript m is 1 or 2 and each $R^{6b}$ is independently selected from the group consisting of H, $C_{1-4}$ alkyl and $C_{1-4}$ alkanoyl. Still further preferred are those embodiments in which $R^1$ is $C_{1-4}$ alkyl; $R^4$ is H or $CH_3$; $R^5$ is halogen or $C_{1-4}$ alkyl; and each $R^6$ when present is selected from $C_{1-4}$ alkyl, —$O(CH_2)_mOR^{6b}$ and —$O(CH_2)_mN(R^{6b})_2$. Even further preferred are those embodiments in which $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or $CH_3$; $R^5$ is chloro and is attached at the 5-position of the thienyl ring; and $R^6$, when present is selected from $C_4$ alkyl, $O(CH_2)_mOR^{6b}$ and $O(CH_2)_mN(R^{6b})_2$ wherein the subscript m is 1 or 2 and each $R^{6b}$ is independently selected from H, $C_{1-4}$ alkyl and $C_{1-4}$ alkanoyl.

Among the most preferred embodiments of the invention are the compounds provided below, as well as in the Examples.

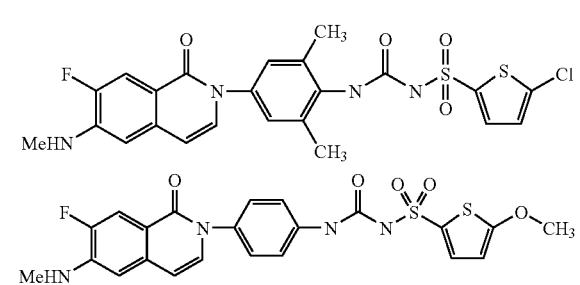

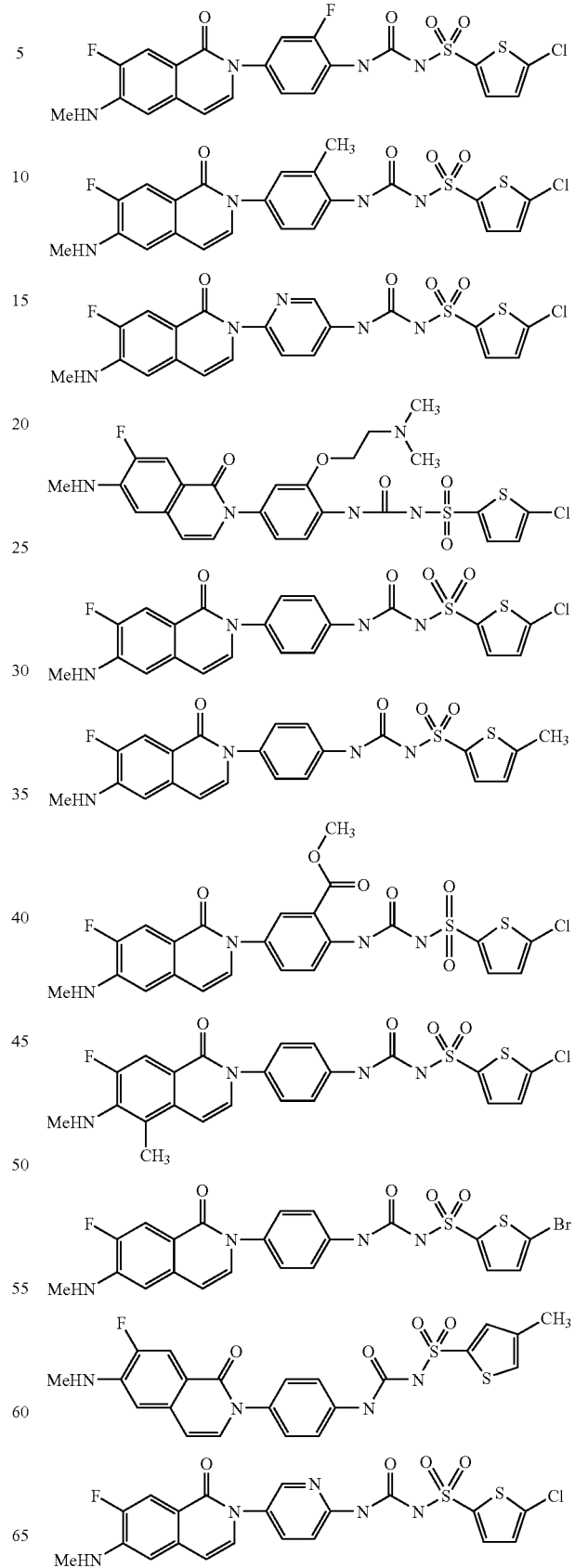

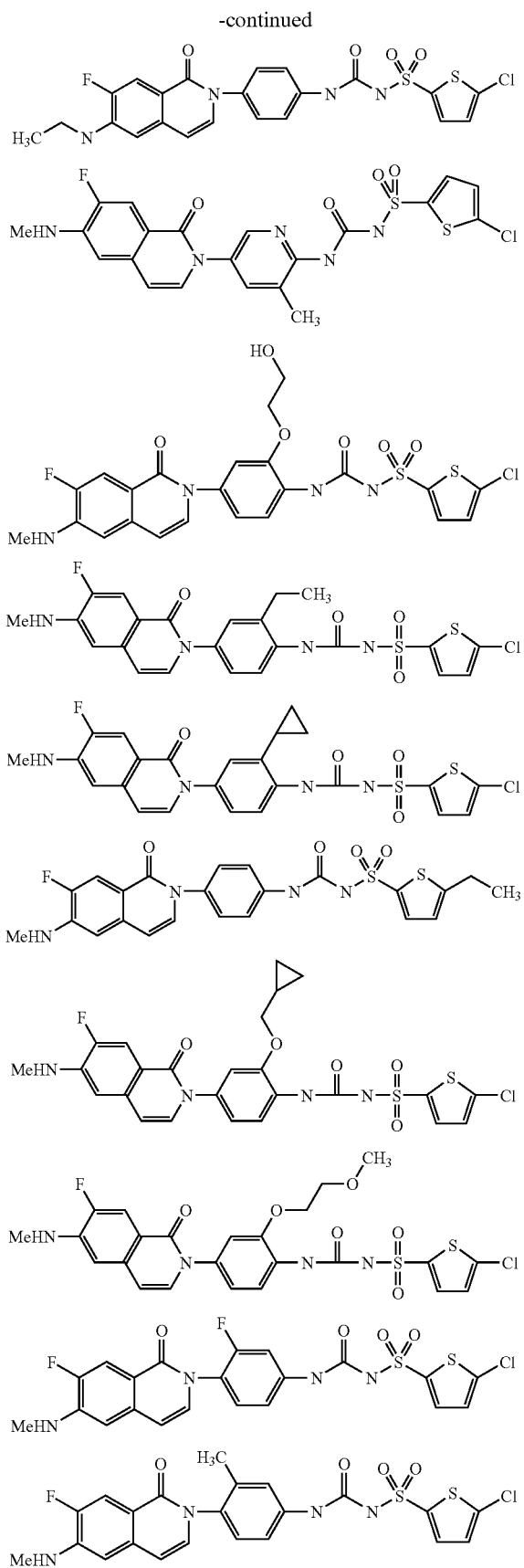
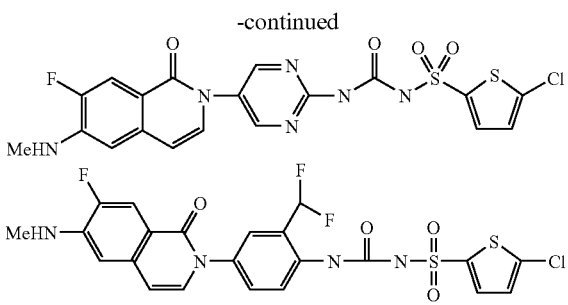
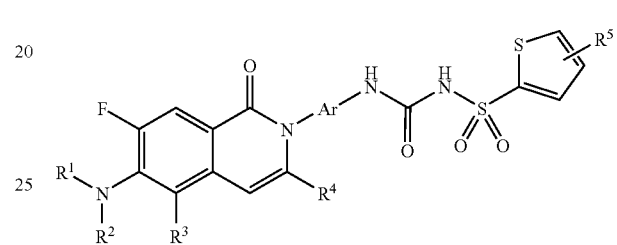
Schemes for the Preparation of Compounds of Formula I
Scheme A describes a method of preparing compounds of Formula I wherein $R^4$=H, $R^1$, $R^2$, $R^3$, $R^5$ is described hereinbefore, Ar is substituted aryl and heteroaryl.
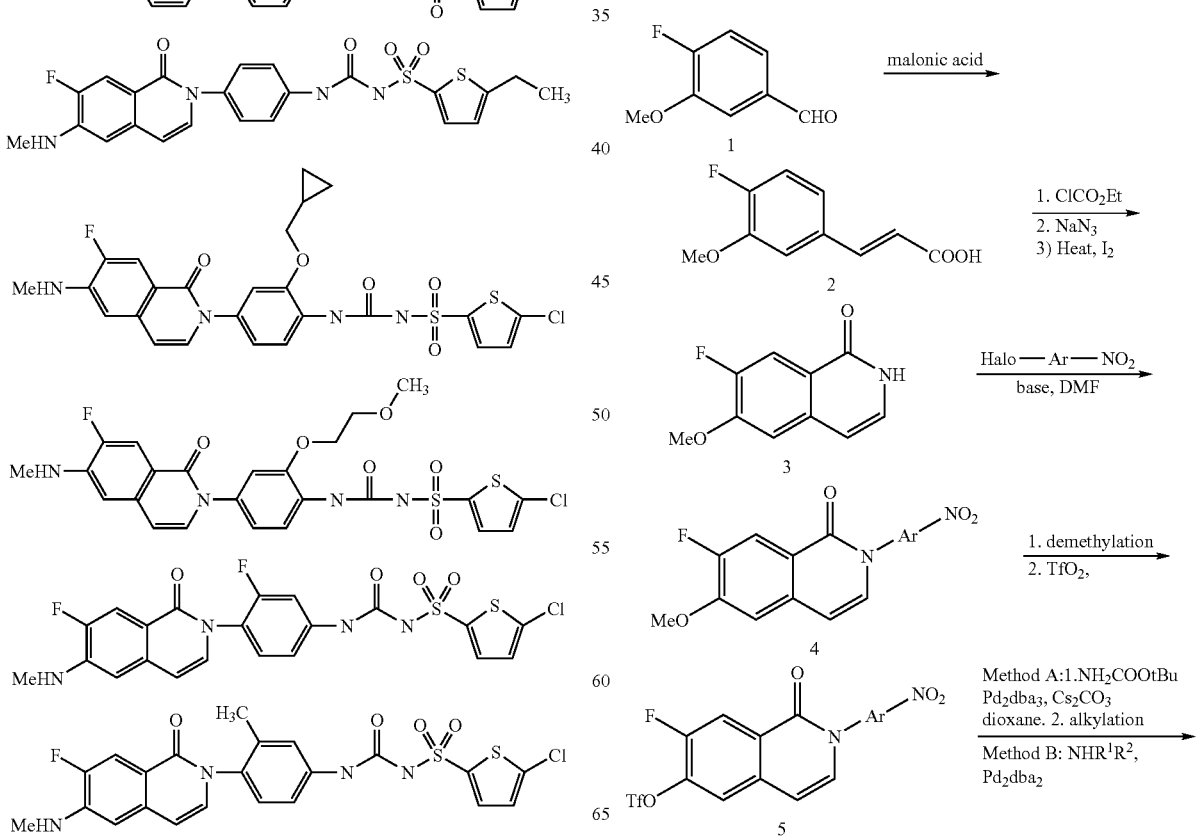

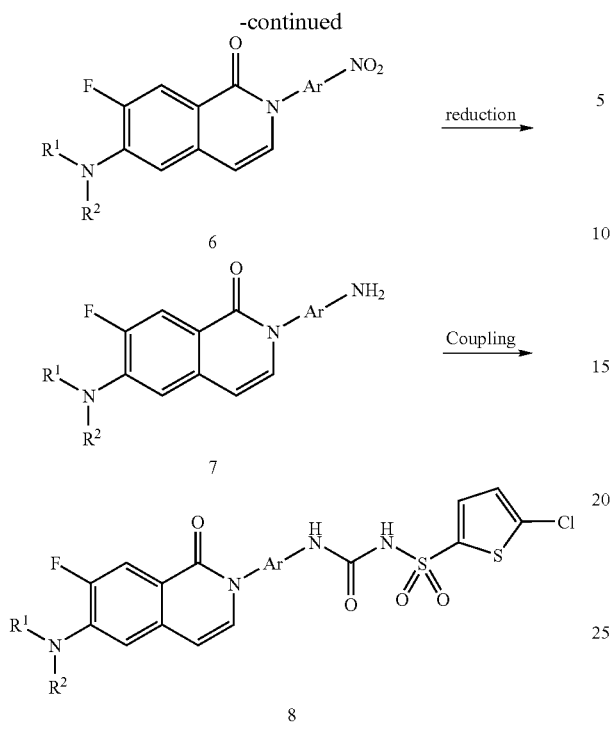

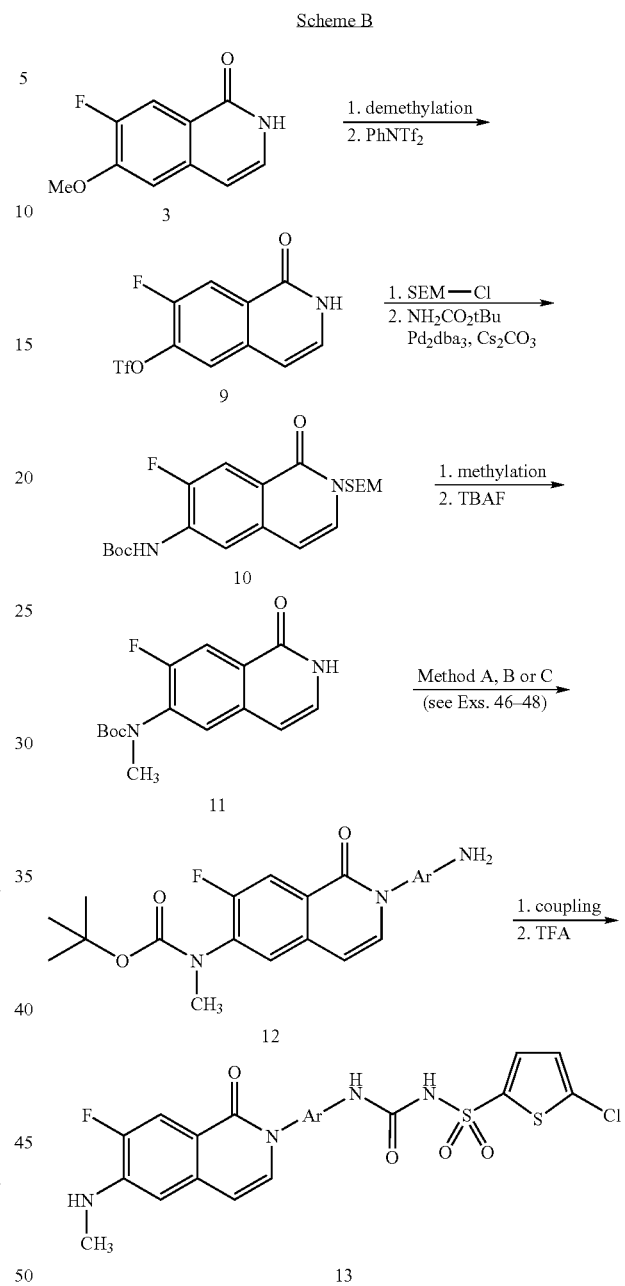

Scheme B

A compound of Formula I can be prepared by reacting malonic acid and benzaldehyde 1 in pyridine to provide cinnamic acid 2, which can be converted to an acryloyl azide by first treating with ethyl chloroformate then sodium azide. Curtius rearrangement and cyclization of acryloyl azide, in the presence of a catalyst such as iodine in an inert solvent such as 1,2-dichlorobenzene provides isoquinolone 3. The substituted isoquinolone 4 can be prepared by treating the amide functionality of isquinolone 3 with a halogen substituted aromatic or heteroaromatic compound, wherein the halogen is a leaving group, preferably chloro or fluoro, in the presence of a base such as potassium carbonate or cesium carbonate. Preferred solvents for this transformation are inert solvents such as DMF, DMSO, and lower alcohols. The methyl group can then be removed by treatment of $BBr_3$ in dichloromethane, or alternatively lithium iodide in an inert solvent such as DMSO or DMF. The C—N coupling reaction of the aryltriflate 5 with carbamic acid tert-butyl ester, or primary or secondary amines can be carried out according to methods described in Buchwald et al., *Org. Lett.* 2000, 2, 1101-1104. The products from coupling reaction of the aryltriflate 5 with carbamic acid tert-butyl ester can be alkylated under basic condition. The nitro group of compound 6 can be reduced by procedures known to one skilled in the art to yield a free amino group. For example, one suitable method of reduction involves hydrogenation, with a suitable catalyst (e.g., 10% palladium on carbon) in an appropriate solvent, typically an alcohol. The formation of the sulfonylurea linkage can be accomplished by treating the reduced product aniline 7 with a pre-mixed solution of 5-chlorothiophene-2-sulfonamide, N,N'-disuccinimidyl carbonate and tetramethylguanidine in dichloromethane, followed by treatment with TFA in dichloromethane at room temperature to afford the sulfonylurea 8.

A compound of Formula I with varying Ar groups can be prepared by first synthesizing the common intermediate 11 in 6 steps (see Scheme B). Compound 3 from Scheme A can be demethylated by treatment with boron tribromide in dichloromethane, followed by selective triflation with phenyltrifluoromethylsulfonimide to give the triflate 9. Protection of the lactam nitrogen, with SEM—Cl and C—N coupling using carbamic acid tert-butyl ester can be carried out according to Buchwald et al., *Org. Lett.* 2000, 2, 1101-1104, to give bis-protected intermediate 10. Standard methylating conditions and removal of the SEM group with TBAF provides the key intermediate 11. A variety of halo-substituted nitroaromatic compounds can be coupled with 11 using Method A or B conditions, followed by reduction using catalytic hydrogenation or tin(II) dichloride dihydrate to give 12 (see, Examples 46 and 47 below). Also, a variety of halo-substituted anilines can be coupled to 10 using Method C conditions as outlined below to give 12 (see, Example 48). The formation of sulfonylurea linkage can be accomplished by treating the product aniline 12 with the ethyl carbamate of 5-chloro-thiophene-2-sulfonamide in refluxing toluene, followed by treatment with TFA in dichloromethane at room temperature to afford the sulfonylurea 13.

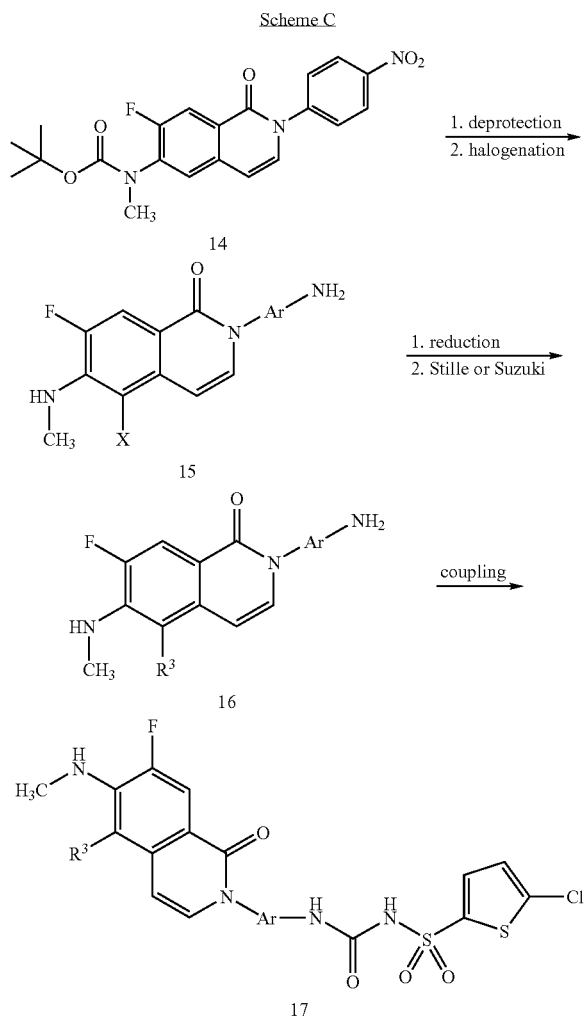

Scheme C describes a method of preparing a compounds of Formula I wherein $R^4$=H, $R^1$=Me, $R^2$=H, $R^5$=Cl, $R^3$ is described hereinbefore. Ar is a substituted or unsubstituted aryl or heteroaryl group.

As seen in Scheme C, compounds of Formula I can be prepared by starting with deprotection of the t-Boc group of compound 14 which can be readily obtained from Scheme B, followed by halogenation to provide compound 15. Conversion of 15 to compound 16 can be accomplished using Stille or Suzuki coupling conditions to provide compound 16 with appropriately substituted $R^3$ group. The formation of a sulfonylurea linkage can be accomplished by treating the reduced product aniline 7 with a pre-mixed solution of 5-chlorothiophene-2-sulfonamide, N,N'-disuccinimidyl carbonate and tetramethylguanidine in dichloromethane, followed by treatment with TFA in dichloromethane at room temperature to afford the sulfonylurea 17.

Compositions

In another aspect of the invention, pharmaceutical compositions are provided in which compounds of formulae I, Ia, Ib, or Ic, alone or in combination, are combined with a pharmaceutically acceptable carrier. Preferred compounds for use in the compositions of the present invention are those compounds identified above as specific or preferred embodiments.

The pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Additionally, dosage formulations of compounds of formulae I, Ia, Ib, or Ic, or pharmaceutical compositions containing a compound of the invention, to be used for therapeutic administration must be sterile. Sterility can be readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae I, Ia, Ib, or Ic, or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae I, Ia, Ib, or Ic, and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be provided in the form of liposome delivery systems, such as small unilamellar vesicles, large unilamellar vesicles and multilamellar vesicles. Liposomes can be formed from a variety of lipids, such as cholesterol, stearylamine or phosphatidylcholines, used methods well known to one of skill in the art.

Methods of Treatment/Administration

In yet another aspect, the present invention provides methods for preventing or treating thrombosis in a mammal by administering to the mammal a therapeutically effective amount of a compound of formulae I, Ia, Ib, or Ic, alone or as part of a pharmaceutical composition of the invention as described above. Compounds of formulae I, Ia, Ib, or Ic, and pharmaceutical compositions of the invention containing a compound of formulae I, Ia, Ib, or Ic, of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Still other agents that can be administered with the compounds of the present invention include antiplatelet compounds, fibrinolytics, anti-inflammatory compounds, cholesterol-lowering agents, blood-pressure-lowering agents and serotonin blockers. Suitable antiplatelet compounds include GPIIB-IIIa antagonists, aspirin, phosphodiesterase III inhibitors and thromboxane A2 receptor antagonists. Suitable anticoagulants include thrombin inhibitors, coumadin (Warfarin), heparin and Lovenox®. Suitable anti-inflammatory compounds include non-steroidal anti-inflammatory agents, cyclooxygenase-2 inhibitors and rheumatoid arthritis agents. Coadministrations of these agents with the compounds of the invention may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

In related methods, the compounds of the invention are useful for the prevention of a secondary ischemic event. In these methods, compounds of the invention or their pharmaceutical compositions are administered to a patient who has suffered a primary ischemic event in an amount sufficient to prevent or reduce the likely occurrence of a secondary event. Generally, the primary and/or secondary ischemic event is selected from myocardial infraction, stable or unstable angina, acute reocclusion after percutaneous transluminal coronary angioplasty, restenosis, thrombotic stroke, transient ischemic attack, reversible ischemic neurological deficit and intermittent claudication.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae I, Ia, Ib, or Ic employed, the specific use for which the compound or pharmaceutical composition is employed, and other factors which those skilled in the medical arts will recognize.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae I, Ia, Ib, or Ic, is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

The following preparations and examples are given to enable those skilled in the art to more clearly understand and to practice the present invention. They should not be considered as limiting the scope of the invention, but merely as being illustrative and representative thereof.

EXAMPLES

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Example 1

3-(4-Fluoro-3-methoxyphenyl)-acrylic acid

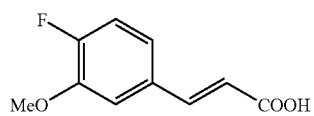

To a solution of 4-fluoro-3-methoxybenzaldehyde (32 g, 0.2 mol) in pyridine (100 mL) was added malonic acid (43 g, 0.4 mol) and piperidine (3 mL, 0.03 mol). The reaction solution was stirred at 85° C. for 13 hr. Upon cooling, the resulting suspension was added to cold water (500 mL) and acidified with conc. HCl (80 mL). The white solid was filtered off, washed with water and dried to yield 36 g (92%) of 3-(4-fluoro-3-methoxyphenyl)-acrylic acid. RP-HPLC: 3.71 min. 1H-NMR (DMSO-$d_6$) δ (ppm) 3.85 (s, 3), 6.53 (d, 1, J=16), 7.20 (m, 2), 7.50 (m, 1), 7.52 (d, 1, J=16).

Example 2

3-(4-Fluoro-3-methoxyphenyl)-acryloyl azide

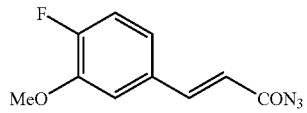

To a chilled solution (ice/acetone) of 3-(4-fluoro-3-methoxyphenyl)-acrylic acid (37 g, 0.194 mmol) in dry THF (280 mL) and triethylamine (352 mL) was added ethyl chloroformate (22.5 mL) in THF (50 mL) dropwise over 20 minutes. The resulting suspension was allowed to warm to 23° C. for 1 h, re-cooled, and a solution of $NaN_3$ (18.7 g) in water (80 mL) was added. The reaction was stirred at 23° C. for 1-2 hr. Workup involved addition of dichloromethane (250 mL) followed by incremental slow addition of 1N HCl. The aqueous layer was further extracted 2 times with dichloromethane. The organic layers were combined, washed with 1N HCl and brine, dried over $MgSO_4$, and concentrated in vacuo to afford 39.8 g (95%) of the acyl azide. RP-HPLC: 5.31 min.

Example 3

7-Fluoro-6-methoxy-2H-isoquinolin-1-one

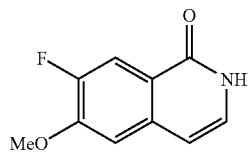

A solution of the acyl azide (39 g, see Example 2) in 1,2-dichlorobenzene (300 mL) was heated to 140° C. for approximately 1 h until gas formation subsides. Catalytic iodine was added and the temperature was increased to 180° C. for 1.5 h. The reaction mixture was allowed to cool to ambient temperature with stirring; the precipitate which formed was collected by filtration, washed with benzene and dried under vacumn to afford 22.6 g (67%) of 7-fluoro-6-methoxy-2H-isoquinolin-1-one as a tan solid. RP-HPLC: 2.58 min; ES-MS (M+H)$^+$=194.1; 1H-NMR (DMSO-$d_6$) δ(ppm): 3.8 (3H, s), 6.48 (1,d), 7.11 (t, 1), 7.33 (d, 1); 6.77 (d, 1).

Example 4

7-Fluoro-6-methoxy-2-(4-nitrophenyl)-2H-isoquinolin-1-one

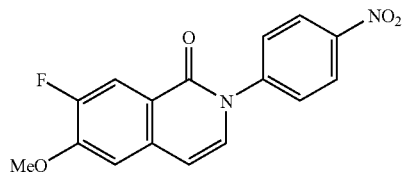

To a solution of 11.0 g of 7-Fluoro-6-methoxy-2H-isoquinolin-1-one (57 mmol) in DMF (108 mL) was added potassium carbonate (11.8 g), followed by 10.6 g of 1-fluoro-4-nitrobenzene (75 mmol). The reaction mixture was stirred at 120° C. for 6 hr then poured onto ice water. The slurry was extracted with ether to remove excess pFPhNO$_2$. The precipitate was collected by filtration, washed with ether and dried in vacuo to give 12.1 g (68%) of the product as a yellow solid. RP-HPLC: 4.79 min; ES-MS (M+H)$^+$=315.0; 1H-NMR (DMSO-d$_6$) δ (ppm): 4.0 (3H, s), 6.76 (1,d), 7.48 (d, 1), 7.53 (d, 1), 7.83 (d,2), 7.92 (d, 1), 8.38 (d, 2).

Example 5

7-Fluoro-6-hydroxy-2-(4-nitro-phenyl)-2H-isoquinolin-1-one

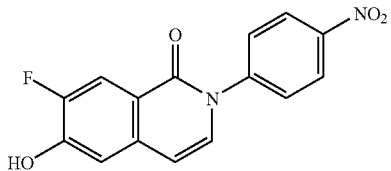

To a chilled suspension of 7-Fluoro-6-methoxy-2-(4-nitrophenyl)-2H-isoquinolin-1-one (3.14 g, 10 mmol) in dichloromethane (50 mL) was added neat boron tribromide (8 mL, 85 mmol) via syringe. The brown suspension was stirred at room temperature for 24 hr. The solvent was decanted, washed with cold DCM, leaving a black residue, which was triturated on ice with methanol (80 mL). The solid was collected by filtration, then washed with water and dried to give 2.66 g (89%) of 7-Fluoro-6-hydroxy-2-(4-nitro-phenyl)-2H-isoquinolin-1-one. RP-HPLC: 3.93 min; ES-MS (M+H)$^+$=301.0; 1H-NMR (DMSO-d$_6$) δ (ppm): 6.66 (d,1), 7.16 (d, 1), 7.43 (d, 1); 7.76 (d, 2), 7.84 (d, 1), 8.33 (d, 2), 11.1 (br s, 1).

Example 6

Trifluoro-methanesulfonic Acid 7-fluoro-2-(4-nitro-phenyl)-1-oxo-1,2-dihydro-isoquinolin-6-yl ester

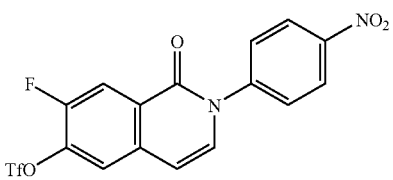

To a suspension of 7-Fluoro-6-hydroxy-2-(4-nitrophenyl)-2H-isoquinolin-1-one (1.15 g, 3.8 mmol) in dry pyridine (25 mL) and dichloromethane (20 mL) was added neat trifluoromethanesulfonic anhydride (0.8 mL, 4.76 mmol) dropwise over 5 min. The resulting solution was stirred at room temp for 2 hr. The reaction mixture was diluted with ethyl acetate (200 mL), washed with 1N HCl (60 mL), water (50 mL) and brine (50 mL), dried over sodium sulfate, filtered, concentrated in vacuo and dried to give 1.37 g (83%) of pure trifluoromethanesulfonic acid 7-fluoro-2-(4-nitro-phenyl)-1-oxo-1,2-dihydro-isoquinolin-6-yl ester. RP-HPLC: 6.20 min; ES-MS (M+H)$^+$=433.0; 1H-NMR (DMSO-d$_6$) δ (ppm): 6.88 (d, 1), 7.64 (d, 1), 7.80 (d, 2), 8.24 (m, 2,; 8.37 (d, 2).

Example 7

[7-Fluoro-2-(4-nitro-phenyl)-1-oxo-1,2-dihydro-isoquinolin-6-yl]-carbamic acid tert-butyl ester

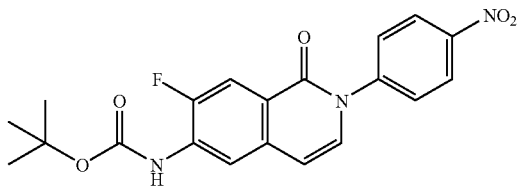

In a dry flask was combined trifluoromethanesulfonic acid 7-fluoro-2-(4-nitro-phenyl)-1-oxo-1,2-dihydro-isoquinolin-6-yl ester (0.86 g, 2 mmol), t-butyl carbamate (0.33 g, 2.8 mmol), dry powdered cesium carbonate (1.1 g, 3.4 mmol), 9,9-dimethyl-4,5-bis(diphenylphosphino)xanthene (Xantphos, 0.14 g, 0.24 mmol), and tris(dibenzylideneacetone) dipalladium(0) (Pd$_2$dba$_3$, 38 mg, 0.08 mmol). Under Ar atmosphere, dry THF (17 mL) was added to the flask, and the mixture was stirred at 75° C. for 25 hr. The reaction was concentrated and purified on silica gel using EtOAc/hexane as eluent to give 0.64 g (80%) of pure [7-Fluoro-2-(4-nitro-phenyl)-1-oxo-1,2-dihydro-isoquinolin-6-yl]-carbamic acid tert-butyl ester as a white solid. RP-HPLC: 5.98 min; ES-MS (M+H)$^+$=400.0; 1H-NMR (DMSO-d$_6$) δ (ppm): 1.47 (s, 9), 6.77 (d, 1), 7.46 (d, 1), 7.78 (d, 2), 7.87 (d, 1), 8.17 (d, 1), 8.33 (d, 2), 9.54 (s, 1).

Example 8

[7-Fluoro-2-(4-nitro-phenyl)-1-oxo-1,2-dihydro-isoquinolin-6-yl]-methyl-carbamic acid tert-butyl ester

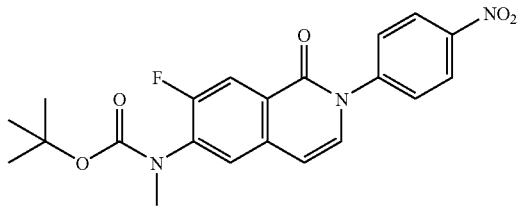

To a solution of [7-Fluoro-2-(4-nitro-phenyl)-1-oxo-1,2-dihydro-isoquinolin-6-yl]-carbamic acid tert-butyl ester (0.36 g, 0.9 mmol) in dry DMF (9 mL) was added cesium carbonate (1.04 g, 3.19 mmol) followed by neat methyl iodide (0.064 mL, 1.03 mmol). The mixture was stirred at room temperature for 3.5 hr, extracted into ethyl acetate (150 mL), washed with water (2×50 mL) and brine (50 mL), dried over sodium sulfate, filtered, concentrated in vacuo and dried to give 0.34 g (93%) of pure [7-Fluoro-2-(4-nitro-phenyl)-1-oxo-1,2-dihydro-isoquinolin-6-yl]-methyl-carbamic acid tert-butyl ester. RP-HPLC: 5.89 min; ES-MS (M+H)⁺=414.0; 1H-NMR (DMSO-d₆) δ (ppm): 1.33 (s, 9), 3.20 (s, 3), 6.75 (d, 1), 7.52 (d, 1), 7.80 (d, 2), 7.83 (d, 1), 7.93 (d, 1), 8.35 (d, 2).

Example 9

[2-(4-Amino-phenyl)-7-fluoro-1-oxo-1,2-dihydro-isoquinolin-6-yl]-methyl-carbamic acid tert-butyl ester

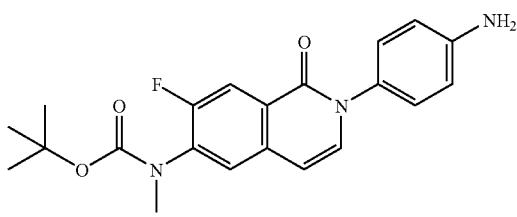

To a suspension of [7-Fluoro-2-(4-nitro-phenyl)-1-oxo-1,2-dihydro-isoquinolin-6-yl]-methyl-carbamic acid tert-butyl ester (0.33 g, 0.79 mmol) in ethyl acetate (6 mL) and ethanol (2 mL) under Ar was added 10% Pd/C (0.13 g, 0.12 mmol Pd). The mixture was hydrogenated under 1 atm H₂ for 2 hr, filtered through Celite and concentrated to give 0.28 g (92%) of [2-(4-Amino-phenyl)-7-fluoro-1-oxo-1,2-dihydro-isoquinolin-6-yl]-methyl-carbamic acid tert-butyl ester. RP-HPLC: 3.83 min; ES-MS (M+H)⁺=384.0; 1H-NMR (DMSO-d₆) δ (ppm): 1.32 (s, 9), 3.17 (s, 3), 5.31 (br s, 2), 6.60 (m, 3), 7.00 (d, 2), 7.32 (d, 2), 7.75 (d, 1), 7.86 (d, 1).

Example 10

5-chloro-N-[({4-[7-fluoro-6-(methylamino)-1-oxoisoquinolin-2(1H)-yl]phenyl}amino)carbonyl]thiophene-2-sulfonamide

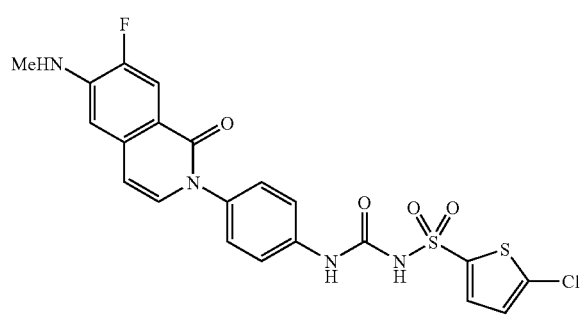

To a suspension of 5-chlorothiophene-2-sulfonamide (0.17 g, 0.84 mmol) and N,N'-disuccinimidyl carbonate (DSC, 0.23 g, 0.91 mmol) in dichloromethane (5 mL) was added tetramethylguanidine (TMG, 0.19 mL). The resulting solution was stirred at room temperature for 15 hr. The reaction was concentrated and a solution of [2-(4-Amino-phenyl)-7-fluoro-1-oxo-1,2-dihydro-isoquinolin-6-yl]-methyl-carbamic acid tert-butyl ester (0.27 g, 0.7 mmol) in acetonitrile (5 mL) was added. The resulting solution was stirred at 70° C. for 9 hr. The reaction was diluted with dichloromethane, washed with 0.5 N HCl, dried over sodium sulfate and concentrated to give 0.48 g of crude sulfonylurea.

To a chilled solution of the crude product in dichloromethane (6 mL) and triethylsilane (2 mL) was added neat trifluoroacetic acid (6 mL). After stirring at room temp for 1 hr, the reaction was concentrated, azeotroped with heptane and dried under high vac to give 0.65 g of crude 5-chloro-N-[[[4-(7-chloro-6-methylamino-1-oxo-2(1H)-isoquinolinyl)phenyl]amino]carbonyl]-2-thiophenesulfonamide. This crude material was triturated with acetonitrile (5 mL), chilled and filtered to give 0.22 g (63%) of pure 5-chloro-N-[({4-[7-fluoro-6-(methylamino)-1-oxoisoquinolin-2(1H)-yl]phenyl}amino)carbonyl]thiophene-2-sulfonamide as a white solid. RP-HPLC: 5.18 min; ES-MS (M+H)⁺=507.0; 1H-NMR (DMSO-d₆) δ (ppm): 2.79 (s, 3), 6.50 (d, 1), 6.53 (br s, 1), 6.70 (d, 1), 7.24 (m, 2), 7.30 (d, 2), 7.46 (d, 2), 7.64 (m, 2).

Example 11

2-(4-Amino-phenyl)-6-cyclopropylamino-7-fluoro-2H-isoquinolin-1-one

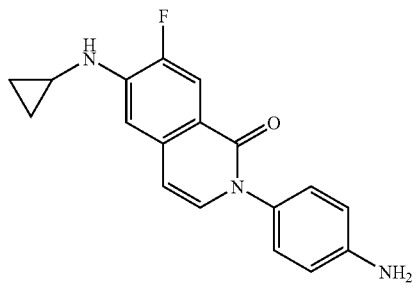

An analogous C—N coupling procedure to that described in Example 7 was performed on trifluoro-methanesulfonic acid 7-fluoro-2-(4-nitro-phenyl)-1-oxo-1,2-dihydro-isoquinolin-6-yl ester (Example 6) using cyclopropylamine as the nucleophile. Reduction of the nitro group was effected using the procedure outlined in Example 9. ES-MS (M+H)⁺= 310.

Example 12

(5-Chloro-thiophene-2-sulfonyl)-carbamic acid ethyl ester

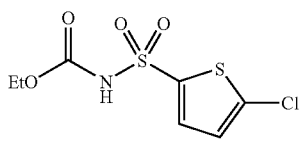

To a solution of 5-Chloro-thiophene-2-sulfonic acid amide (4.0 g, 20.2 mmol) in dry THF (200 mL) was added cesium carbonate (9.9 g, 30.3 mmol) and ethyl chloroformate (2.9 mL, 30.3 mmol). The mixture was stirred at room temperature for 48 h. The product was taken up in H₂O (150 mL) and washed with EtOAc (100 mL). The aqueous layer was acidified to pH=3 with 1N HCl (90 mL) and the product extracted with EtOAc (100 mL). The organic layer was washed with brine (100 mL), dried over Na₂SO₄ and concentrated to give a dense clear oil which solidified upon standing to give 4.41 g (81%) of 5-Chloro-thiophene-2-sulfonyl)-carbamic acid ethyl ester. RP-HPLC: 4.45 min. 1H-NMR (CDCl$_3$) δ (ppm): 7.63 (d, J=4, 1H), 7.44 (bs, 1H), 6.95 (d, J=4, 1H), 4.20 (q, J=7, 2H), 1.27 (t, J=7, 3H).

Example 13

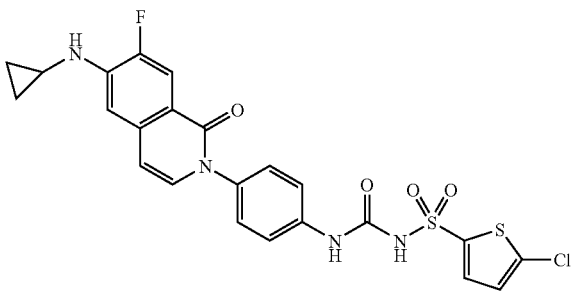

A mixture of 2-(4-Amino-phenyl)-6-cyclopropylamino-7-fluoro-2H-isoquinolin-1-one (Example 11) (23 mg, 0.073 mmol) and (5-Chloro-thiophene-2-sulfonyl)-carbamic acid ethyl ester (Example 12) (28 mg, 0.10 mmol, 1.35 eq) in dry toluene (1.5 mL) was heated at 110° C. for 2 hr. Upon cooling, the reaction was concentrated in vacuo and the crude residue was purified by HPLC (C-18) to give 17 mg (46%) of pure 5-chloro-N-[({4-[6-(cyclopropylamino)-7-fluoro-1-oxoisoquinolin-2(1H)-yl]phenyl}amino)carbonyl]thiophene-2-sulfonamide. ES-MS (M+H)$^+$=533, 535 (Cl).

Example 14

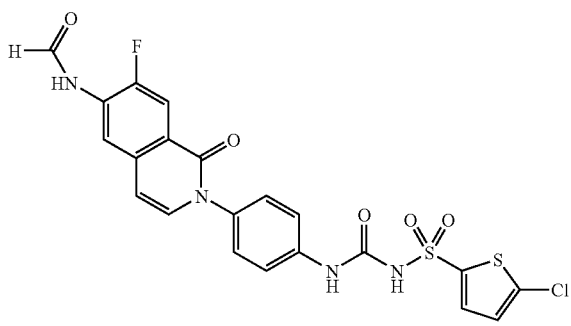

An analogous C—N coupling procedure to that described in Example 7 was performed on trifluoro-methanesulfonic acid 7-fluoro-2-(4-nitro-phenyl)-1-oxo-1,2-dihydro-isoquinolin-6-yl ester (Example 6) using formamide as the nucleophile. Reduction of the nitro group was effected using the procedure outlined in Example 9. Coupling to form the sulfonyl urea was achieved using the method described in Example 13 to give 5-chloro-N-[({4-[7-fluoro-6-(formylamino)-1-oxoisoquinolin-2(1H)-yl]phenyl}amino)carbonyl]thiophene-2-sulfonamide. ES-MS (M+H)$^+$=521, 523 (Cl).

Example 15

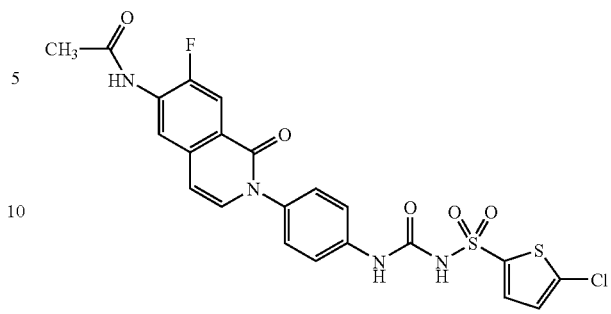

An analogous C—N coupling procedure to that described in Example 7 was performed on trifluoro-methanesulfonic acid 7-fluoro-2-(4-nitro-phenyl)-1-oxo-1,2-dihydro-isoquinolin-6-yl ester (Example 6) using acetamide as the nucleophile. Reduction of the nitro group was effected using the procedure outlined in Example 9. Coupling to form the sulfonyl urea was achieved using the method described in Example 13 to give N-(2-{4-[({[(5-chlorothien-2-yl)sulfonyl]amino}carbonyl)amino]phenyl}-7-fluoro-1-oxo-1,2-dihydroisoquinolin-6-yl)acetamide. ES-MS (M+H)$^+$=535, 537 (Cl).

Example 16

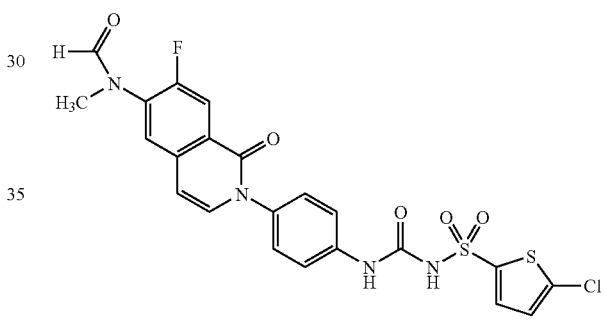

An analogous C—N coupling procedure to that described in Example 7 was performed on Trifluoro-methanesulfonic acid 7-fluoro-2-(4-nitro-phenyl)-1-oxo-1,2-dihydro-isoquinolin-6-yl ester (Example 6) using N-methylformamide as the nucleophile, followed by alkylation and reduction of the nitro group using the procedure outlined in Examples 8 and 9. Coupling to form the sulfonyl urea was achieved using the method described in Example 13 to give 5-chloro-N-[({4-[7-fluoro-6-[formyl(methyl)amino]-1-oxoisoquinolin-2(1H)-yl]phenyl}amino)carbonyl]thiophene-2-sulfonamide. ES-MS (M+H)$^+$=535, 537 (Cl).

Example 17

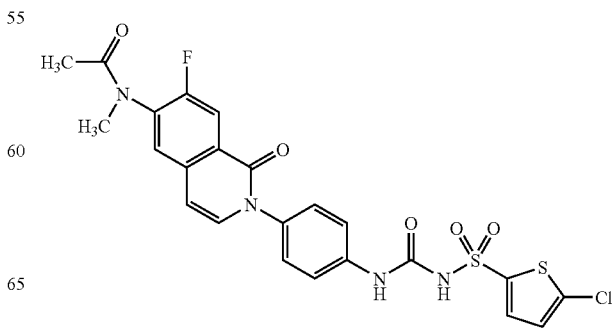

An analogous C—N coupling procedure to that described in Example 7 was performed on trifluoro-methanesulfonic acid 7-fluoro-2-(4-nitro-phenyl)-1-oxo-1,2-dihydro-isoquinolin-6-yl ester (Example 6) using N-methylacetamide as the nucleophile, followed by alkylation and reduction of the nitro group using the procedure outlined in Examples 8 and 9. Coupling to form the sulfonyl urea was achieved using the method described in Example 13 to give N-(2-{4-[({[(5-chlorothien-2-yl)sulfonyl]amino}carbonyl)amino]phenyl}-7-fluoro-1-oxo-1,2-dihydroisoquinolin-6-yl)-N-methylacetamide. ES-MS (M+H)$^+$=549, 551 (Cl).

Example 18

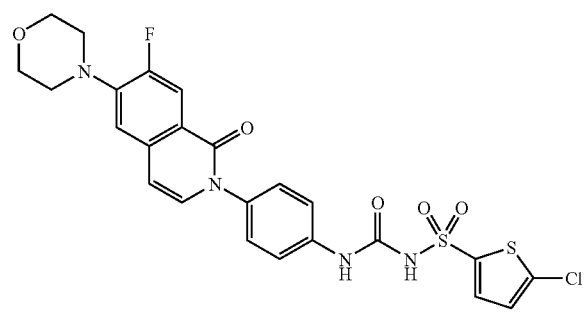

An analogous C—N coupling procedure to that described in Example 7 was performed on trifluoro-methanesulfonic acid 7-fluoro-2-(4-nitro-phenyl)-1-oxo-1,2-dihydro-isoquinolin-6-yl ester (Example 6) using morpholine as the nucleophile. Reduction of the nitro group was effected using the procedure outlined in Example 9. Coupling to form the sulfonyl urea was achieved using the method described in Example 13 to give 5-chloro-N-({[4-(7-fluoro-6-morpholin-4-yl-1-oxoisoquinolin-2(1H)-yl)phenyl]amino}carbonyl)thiophene-2-sulfonamide. ES-MS (M+H)$^+$=563, 565 (Cl).

Example 149

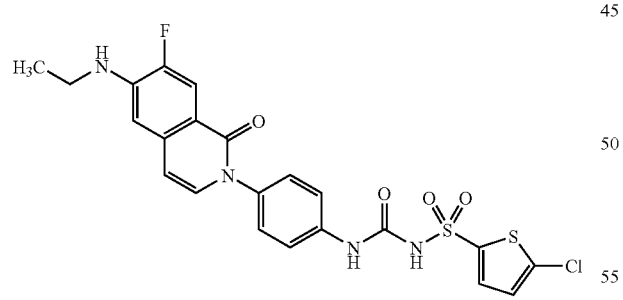

An analogous alkylation procedure to that described in Example 8 was performed on [7-fluoro-2-(4-nitro-phenyl)-1-oxo-1,2-dihydro-isoquinolin-6-yl]-carbamic acid tert-butyl ester (Example 7) using ethyl iodide as the alkylating agent. Reduction of the nitro group and coupling to form the sulfonyl urea was achieved using the method described in Exs. 9 and 10, resp. to give 5-chloro-N-[({4-[6-(ethylamino)-7-fluoro-1-oxoisoquinolin-2(1H)-yl]phenyl}amino)carbonyl]thiophene-2-sulfonamide. ES-MS (M+H)$^+$=521, 523 (Cl).

Example 20

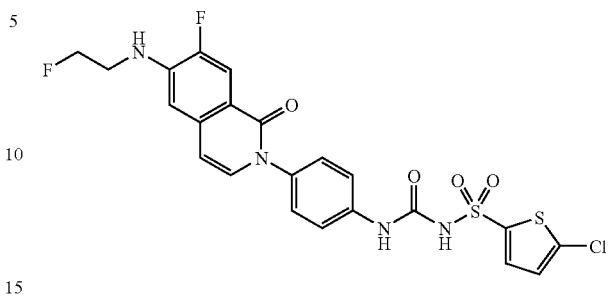

An analogous alkylation procedure to that described in Example 8 was performed on [7-fluoro-2-(4-nitro-phenyl)-1-oxo-1,2-dihydro-isoquinolin-6-yl]-carbamic acid tert-butyl ester (Example 7) using 1-bromo-2-fluoroethane as the alkylating agent. Reduction of the nitro group and coupling to form the sulfonyl urea was achieved using the method described in Exs. 9 and 10, resp. to give 5-chloro-N-[({4-[7-fluoro-6-[(2-fluoroethyl)amino]-1-oxoisoquinolin-2(1H)-yl]phenyl}amino)carbonyl]thiophene-2-sulfonamide. ES-MS (M+H)$^+$=539, 541 (Cl).

Example 21

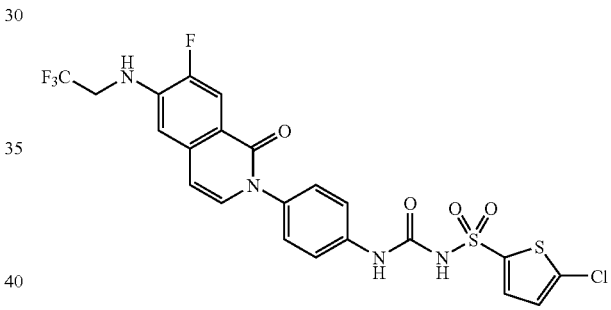

An analogous alkylation procedure to that described in Example 8 was performed on [7-fluoro-2-(4-nitro-phenyl)-1-oxo-1,2-dihydro-isoquinolin-6-yl]-carbamic acid tert-butyl ester (Example 7) using 2,2,2-trifluoroethyl-p-toluenesulfonate as the alkylating agent with additional heating at 95° C. Reduction of the nitro group and coupling to form the sulfonyl urea was achieved using the method described in Exs. 9 and 10, respectively, to give 5-chloro-N-[({4-[7-fluoro-1-oxo-6-[(2,2,2-trifluoroethyl)amino]isoquinolin-2(1H)-yl]phenyl}amino)carbonyl]thiophene-2-sulfonamide. ES-MS (M+H)$^+$=575, 577 (Cl).

Example 22

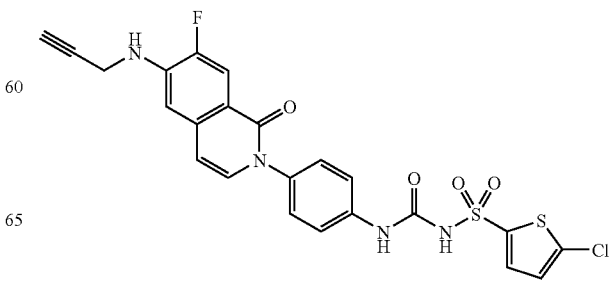

An analogous alkylation procedure to that described in Example 8 was performed on [7-fluoro-2-(4-nitro-phenyl)-1-oxo-1,2-dihydro-isoquinolin-6-yl]-carbamic acid tert-butyl ester (Example 7) using proparyl bromide as the alkylating agent. Reduction of the nitro group and coupling to form the sulfonyl urea was achieved using the method described in Exs. 9 and 10, resp. to give 5-chloro-N-[({4-[7-fluoro-1-oxo-6-(prop-2-ynylamino)isoquinolin-2(1H)-yl]phenyl}amino)carbonyl]thiophene-2-sulfonamide. ES-MS (M+H)$^+$=531, 533 (Cl).

Example 23

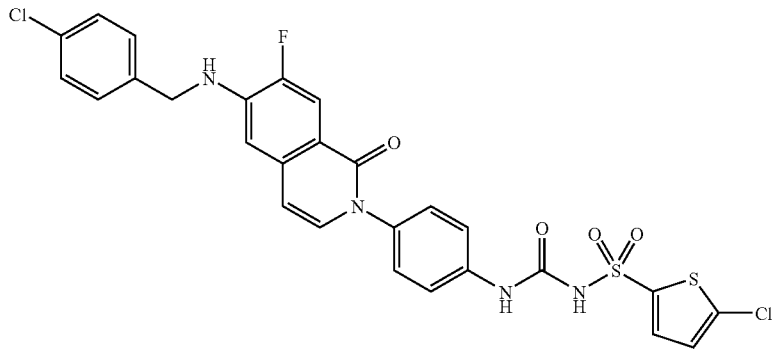

An analogous alkylation procedure to that described in Example 8 was performed on [7-fluoro-2-(4-nitro-phenyl)-1-oxo-1,2-dihydro-isoquinolin-6-yl]-carbamic acid tert-butyl ester (Example 7) using 4-chlorobenzylbromide as the alkylating agent. Reduction of the nitro group and coupling to form the sulfonyl urea was achieved using the method described in Exs. 9 and 10, resp. to give 5-chloro-N-[({4-[6-[(4-chlorobenzyl)amino]-7-fluoro-1-oxoisoquinolin-2(1H)-yl]phenyl}amino)carbonyl]thiophene-2-sulfonamide. ES-MS (M+H)$^+$=617, 619 (2Cl).

Example 24

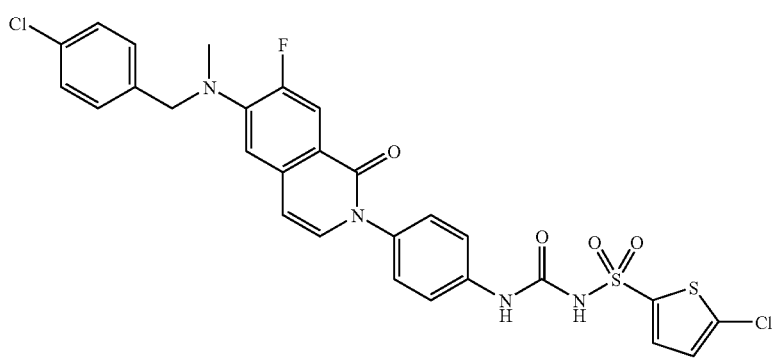

The alkylated intermediate synthesized in Example 23 was treated with TFA and methylated with methyl iodide and cesium carbonate. Reduction of the nitro group and coupling to form the sulfonyl urea was achieved using the method described in Example 9 and 10, to give 5-chloro-N-[({4-[6-[(4-chlorobenzyl)(methyl)amino]-7-fluoro-1-oxoisoquinolin-2(1H)-yl]phenyl}amino)carbonyl]thiophene-2-sulfonamide. ES-MS (M+H)$^+$=631, 633 (2Cl).

Example 25

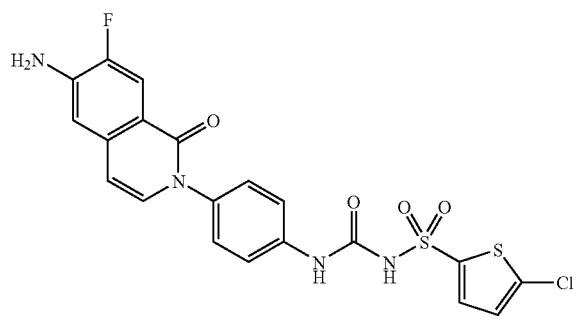

Reduction of [7-fluoro-2-(4-nitro-phenyl)-1-oxo-1,2-dihydro-isoquinolin-6-yl]-carbamic acid tert-butyl ester (Example 7) was effected using the procedure outlined in Example 9. Coupling to form the sulfonyl urea was achieved using the method described in Example 10 to give N-({[4-(6-amino-7-fluoro-1-oxoisoquinolin-2(1H)-yl)phenyl]amino}carbonyl)-5-chlorothiophene-2-sulfonamide. ES-MS (M+H)$^+$=493, 495 (Cl).

Example 26

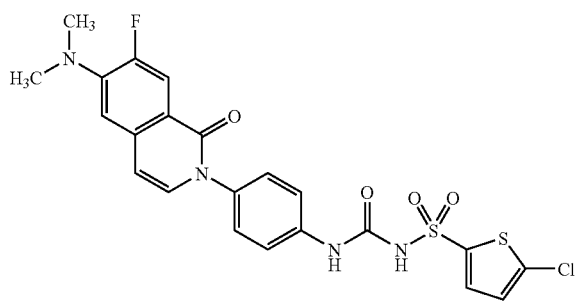

To a suspension of the sulfonyl urea from Example 25 (11 mg, 0.023 mmol) in glacial acetic acid (0.9 mL) was added formaldehyde (37 wt % in water) (12 uL, 0.16 mmol) followed by sodium triacetoxyborohydride (11 mg, 0.052 mmol). The reaction mixture was stirred at room temperature overnight and concentrated in vacuo. The crude residue was purified by HPLC to give 5-chloro-N-[({4-[6-(dimethylamino)-7-fluoro-1-oxoisoquinolin-2(1H)-yl]phenyl}amino)carbonyl]thiophene-2-sulfonamide. ES-MS (M+H)$^+$=521, 523 (Cl).

Example 27

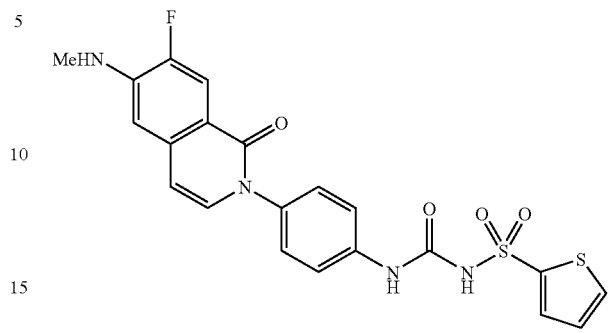

An analogous coupling procedure described in Example 10 was performed on [2-(4-Amino-phenyl)-7-fluoro-1-oxo-1,2-dihydro-isoquinolin-6-yl]-methyl-carbamic acid tert-butyl ester (Example 9) using commercially available thiophene-2-sulfonamide to give N-[({4-[7-fluoro-6-(methylamino)-1-oxoisoquinolin-2(1H)-yl]phenyl}amino) carbonyl]thiophene-2-sulfonamide. ES-MS (M+H)$^+$=473.

Example 28

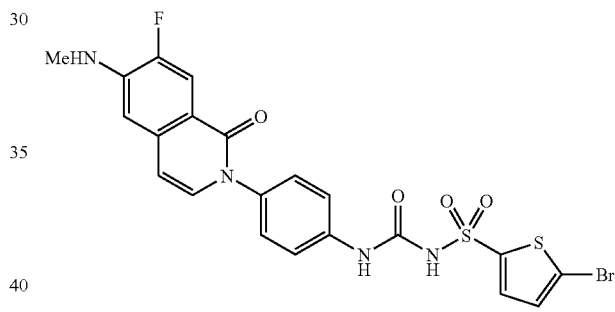

An analogous coupling procedure as that described in Example 10 was performed on [2-(4-Amino-phenyl)-7-fluoro-1-oxo-1,2-dihydro-isoquinolin-6-yl]-methyl-carbamic acid tert-butyl ester (Example 9) and commercially available 5-bromothiophene-2-sulfonamide to give 5-bromo-N-[({4-[7-fluoro-6-(methylamino)-1-oxoisoquinolin-2(1H)-yl]phenyl}amino)carbonyl]thiophene-2-sulfonamide. ES-MS (M+H)$^+$=551, 553 (Br).

Example 29

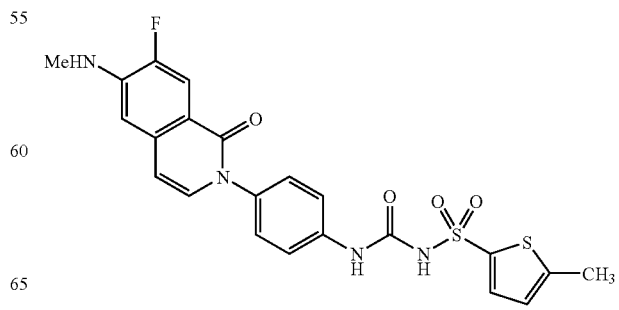

To a solution of triphosgene (9 mg, 31 μmol) in dichloromethane (0.2 mL) was slowly added a solution of [2-(4-Amino-phenyl)-7-fluoro-1-oxo-1,2-dihydro-isoquinolin-6-yl]-methyl-carbamic acid tert-butyl ester (30 mg, 78 μmol) and DIEA (27 μL, 156 μmol) in dichloromethane (1.0 mL). The mixture was stirred at room temperature for 15 min. To this solution was then quickly added a solution of 5-methylthiophene-2-sulfonamide (28 mg, 156 μmol) and DIEA (27 μL, 156 μmol) in dichloromethane (1.0 mL). The mixture was then stirred at room temperature for 15 min. The reaction mixture was then diluted with dichloromethane, washed with 0.5 N HCl, dried over sodium sulfate and concentrated to give 62 mg of crude sulfonylurea as a cloudy oil. The crude mixture was dissolved in TFA, reacted at room temperature for 15 min., and concentrated in vacuo to give the crude final product as yellow oil which was purified by HPLC to give 17 mg (45%) of N-({[4-(6-amino-7-fluoro-1-oxoisoquinolin-2(1H)-yl)phenyl]amino}carbonyl)-5-methylthiophene-2-sulfonamide as a white solid. ES-MS (M+H)$^+$=487.1; 1H-NMR (DMSO-d$_6$) δ (ppm): 8.84-8.80 (bd, J=4.5 Hz, 1H), 7.66-7.60 (d, J=12.8 Hz, 1H), 7.50-7.44 (d, J=8.8 Hz, 2H), 7.40-7.36 (bs, 1H), 7.25-7.15 (m, 3H), 6.80-6-74 (bs, 1H), 6.74-6.66 (d, J=8.4 Hz, 1H), 6.56-6.48 (bs, 1H), 6.50-6.46 (d, J=8 Hz, 1H), 2.82-2.77 (bd, J=4.5 Hz, 3H).

Example 30

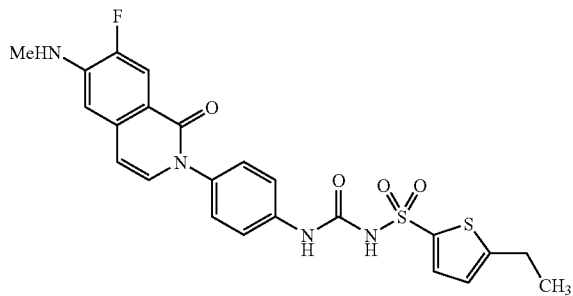

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-ethylthiophene-2-sulfonamide to give N-({[4-(6-amino-7-fluoro-1-oxoisoquinolin-2(1H)-yl)phenyl]amino}carbonyl)-5-ethylthiophene-2-sulfonamide. ES-MS (M+H)$^+$=501.1.

Example 31

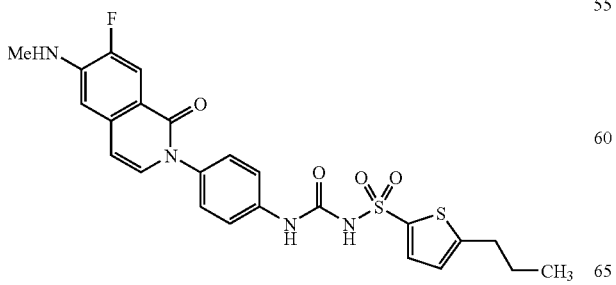

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-propylthiophene-2-sulfonic acid amide to give N-({[4-(6-amino-7-fluoro-1-oxoisoquinolin-2(1H)-yl)phenyl]amino}carbonyl)-5-propylthiophene-2-sulfonamide. ES-MS (M+H)$^+$=515.1; 1H-NMR (DMSO-d$_6$) δ (ppm): 9.06-9.00 (s, 1H), 7.66-7.62 (d, J=12.4 Hz, 1H), 7.62-7.58 (d, J=3.7 Hz, 1H), 7.48-7.42 (m, 2H), 7.32-7.26 (m, 2H), 7.24-7.20 (d, J=7.3 Hz, 1H), 6.96-6-90 (d, J=3.6 Hz, 1H), 6.74-6.66 (d, J=8.4 Hz, 1H), 6.58-6.48 (bs, 1H), 6.50-6.46 (d, J=7.3 Hz, 1H), 2.84-2.76 (m, 5H), 1.68-1.56 (tq, J=7.3, 7.6 Hz, 2H), 0.94-0.86 (t, J=7.3 Hz, 3H).

Example 32

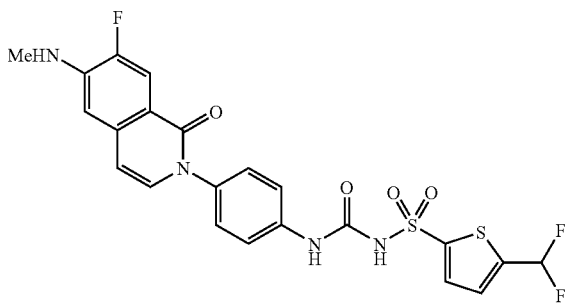

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-difluoromethyl-thiophene-2-sulfonic acid amide to give N-({[4-(6-amino-7-fluoro-1-oxoisoquinolin-2(1H)-yl)phenyl]amino}carbonyl)-5-difluoromethylthiophene-2-sulfonamide. ES-MS (M+H)$^+$=523.1; 1H-NMR (DMSO-d$_6$) δ (ppm): 8.70-8.64 (s, 1H), 7.66-7.60 (d, J=12.4 Hz), 7.56-7.48 (m, 2h), 7.38-7.10 (t, J=55.3 Hz, 1H), 7.36-7.32 (m, 1H), 7.28-7.24 (m, 1H), 7.22-7.18 (d, J=7.7 Hz, 1H), 7.12-7.06 (m, 2H), 6.72-6.66 (d, J=8.4 Hz, 1H), 6.52-6.46 (bs, 1H), 6.48-6.44 (d, J=7.3 Hz, 1H), 2.81-2.77 (bd, J=4.7 Hz, 3H).

Example 33

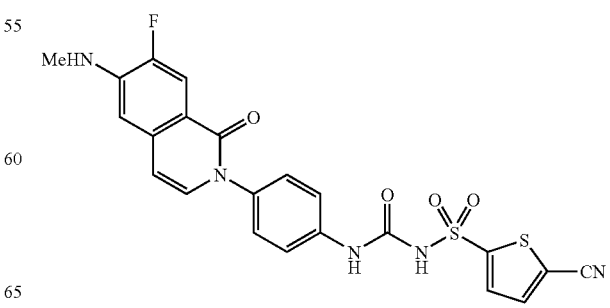

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-cyanothiophene-2-sulfonamide to give N-({[4-(6-amino-7-fluoro-1-oxoisoquinolin-2(1H)-yl)phenyl]amino}carbonyl)-5-cyanothiophene-2-sulfonamide. ES-MS (M+H)$^+$=498.1.

Example 34

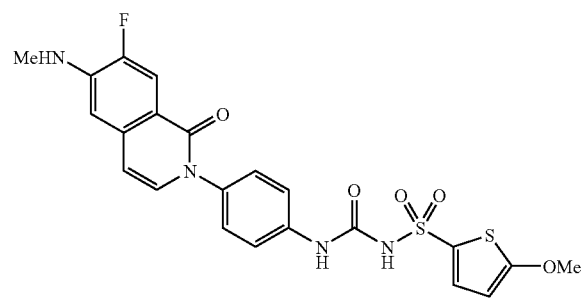

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-methoxythiophene-2-sulfonamide to give N-({[4-(6-amino-7-fluoro-1-oxoisoquinolin-2(1H)-yl)phenyl]amino}carbonyl)-5-ethylthiophene-2-sulfonamide. ES-MS (M+H)$^+$=503.1; 1H-NMR (DMSO-d$_6$) δ (ppm): 9.15-9.00 (s, 1H), 7.68-7.60 (d, J=12.5 Hz, 1H), 7.52-7.50 (d, J=3.3 Hz, 1H), 7.48-7.44 (d, J=8.8 Hz, 2H), 7.34-7.28 (d, J=8.8 Hz, 2H), 7.25-7.20 (d, J=7.3 Hz, 1H), 6.74-6.68 (d, J=7.7 Hz, 1H), 6.56-6.50 (bs, 1H), 6.52 (d, J=7.7 Hz, 1H), 6.44-6.40 (d, J=3.3 Hz, 1H), 3.94-3.92 (s, 3H), 2.82-2.78 (bd, J=4.4 Hz, 3H).

Example 35

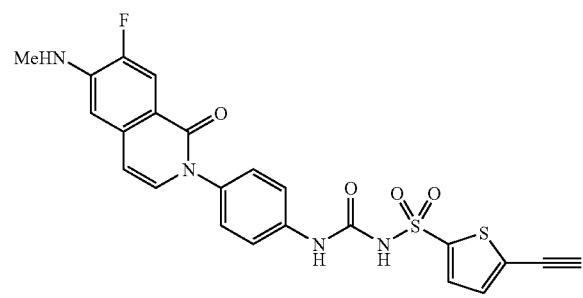

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-ethynylthiophene-2-sulfonamide to give N-({[4-(6-amino-7-fluoro-1-oxoisoquinolin-2(1H)-yl)phenyl]amino}carbonyl)-5-ethynylthiophene-2-sulfonamide.
ES-MS (M+H)$^+$=497.1; 1H-NMR (DMSO-d$_6$) δ (ppm): 9.22-9.18 (bs, 1H), 7.70-7.66 (m, 1H), 7.65-7.60 (d, J=12.4 Hz, 1H), 7.48-7.42 (d, J=9.1 Hz, 2H), 7.40-7.36 (m, 1H), 7.32-7.25 (d, J=8.8 Hz, 2H), 7.24-7.18 (d, J=7.7 Hz, 1H), 6.72-6.66 (d, J=8.4 Hz, 1H), 6.58-6.48 (bs, 1H), 6.50-6.46 (d, J=7.3 Hz, 1H), 4.86-4.84 (s, 1H), 2.82-2.76 (s, 3H).

Example 36

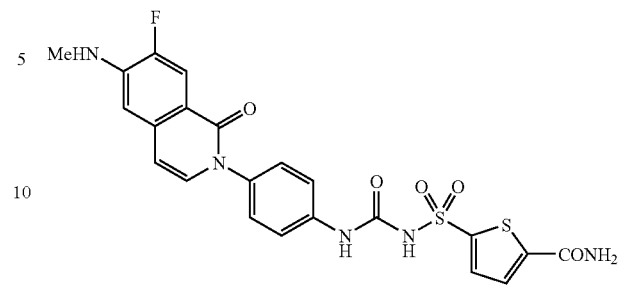

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 5-carboxamidethiophene-2-sulfonamide to give N-({[4-(6-amino-7-fluoro-1-oxoisoquinolin-2(1H)-yl)phenyl]amino}carbonyl)-5-carboxamidethiophene-2-sulfonamide. ES-MS (M+H)$^+$=516.1.

Example 37

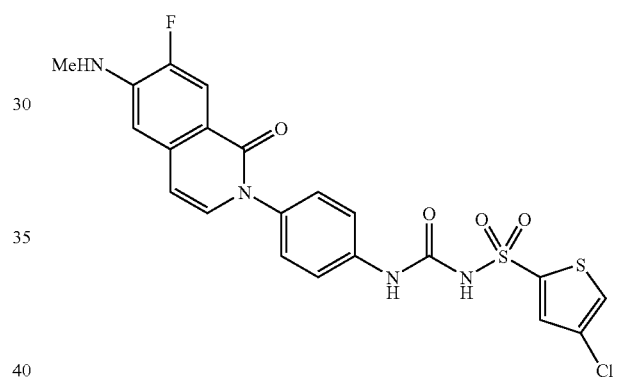

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 4-chlorothiophene-2-sulfonamide to give N-({[4-(6-amino-7-fluoro-1-oxoisoquinolin-2(1H)-yl)phenyl]amino}carbonyl)-4-chlorothiophene-2-sulfonamide. ES-MS (M+H)$^+$=507.0, 509.0 (Cl).

Example 38

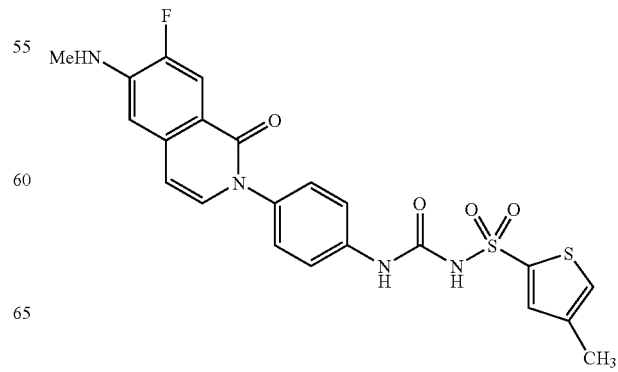

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 4-methylthiophene-2-sulfonamide to give N-({[4-(6-amino-7-fluoro-1-oxoisoquinolin-2(1H)-yl)phenyl]amino}carbonyl)-4-methylthiophene-2-sulfonamide. ES-MS (M+H)$^+$=487.1.

Example 39

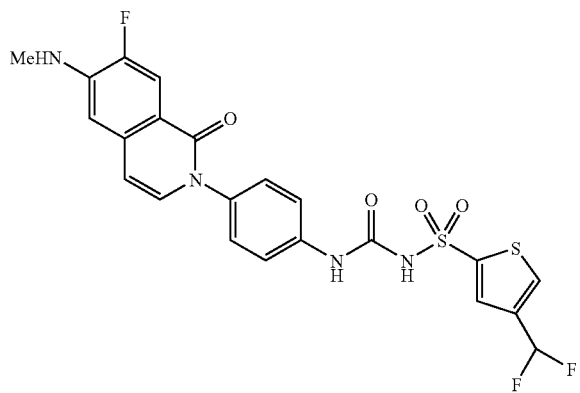

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 4-difluoromethylthiophene-2-sulfonamide to give N-({[4-(6-amino-7-fluoro-1-oxoisoquinolin-2(1H)-yl)phenyl]amino}carbonyl)-4-difluoromethylthiophene-2-sulfonamide. ES-MS (M+H)$^+$=523.1; 1H-NMR (DMSO-d$_6$) δ (ppm): 9.24-9.16 (bs, 1H), 8.34-8.28 (m, 1H), 7.88-7.84 (m, 1H), 7.66-7.60 (d, J=12.4 Hz, 1H), 7.48-7.42 (d, J=8.8 Hz, 2H), 7.34-7.26 (d, J=8.8 Hz, 2H), 7.25-7.20 (d, J=7.3 Hz, 1H), 7.19-6.91 (t, J=55.3 Hz, 1H), 6.72-6.66 (d, 8.4 Hz, 1H), 6.58-6.48 (bs, 1H), 6.50-6.46 (d, J=7.3 Hz, 1H), 2.82-2.77 (s, 3H).

Example 40

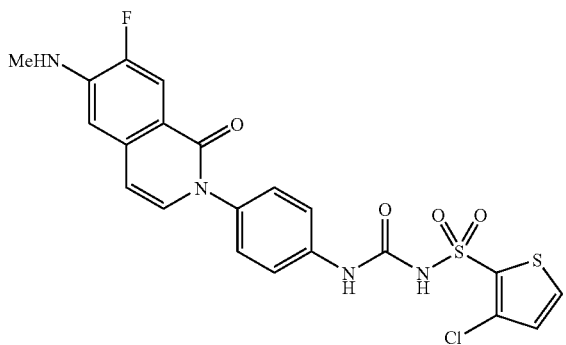

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) using 3-chloro-thiophene-2-sulfonic acid amide as the coupling partner to give N-({[4-(6-amino-7-fluoro-1-oxoisoquinolin-2(1H)-yl)phenyl]amino}carbonyl)-3-chlorothiophene-2-sulfonamide. ES-MS (M+H)$^+$=507.0, 509.0 (Cl); 1H-NMR (DMSO-d$_6$) δ (ppm): 8.98-8.91 (bs, 1H), 8.06-7.98 (m, 1H), 7.66-7.60 (d, J=12.8 Hz, 1H), 7.48-7.40 (d, J=8.8 Hz, 2H), 7.30-7.25 (d, J=8.8 Hz, 2H), 7.24-7.20 (m, 1H), 7.24-7.18 (d, J=7.3 Hz, 1H), 6.72-6.66 (d, J=8.4 Hz, 1H), 6.56-6.48 (bs, 1H), 6.50-6.46 (d, J=7.3 Hz, 1H), 2.82-2.75 (s, 3H).

Example 41

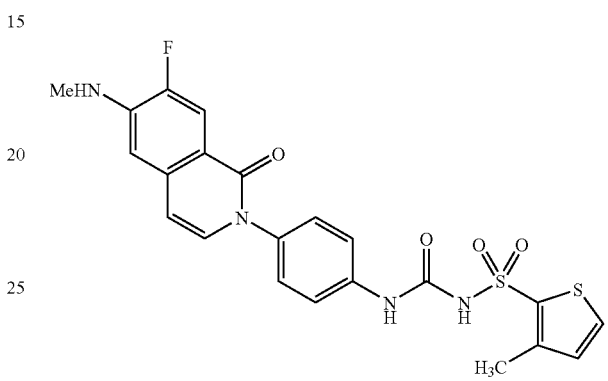

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9) and 3-methyl-thiophene-2-sulfonamide to give N-({[4-(6-amino-7-fluoro-1-oxoisoquinolin-2(1H)-yl)phenyl]amino}carbonyl)-3-methylthiophene-2-sulfonamide.
ES-MS (M+H)$^+$=487.1; 1H-NMR (DMSO-d$_6$) δ (ppm): 8.96-8.92 (bs, 1H), 7.86-7.82 (d, J=5.1 Hz, 1H), 7.66-7.60 (d, J=12.4 Hz, 1H), 7.46-7.40 (m, 2H), 7.32-7.26 (m, 2H), 7.24-7.20 (d, J=7.3 Hz, 1H), 7.03-7.00 (d, J=5.1 Hz, 1H), 6.72-6.68 (d, J=8.8 Hz, 1H), 6.56-6.48 (bs, 1H), 6.50-6.46 (d, J=7.7 Hz, 1H), 2.82-2.78 (bd, J=4.8 Hz, 3H), 2.45-2.43 (s, 3H).

Example 42

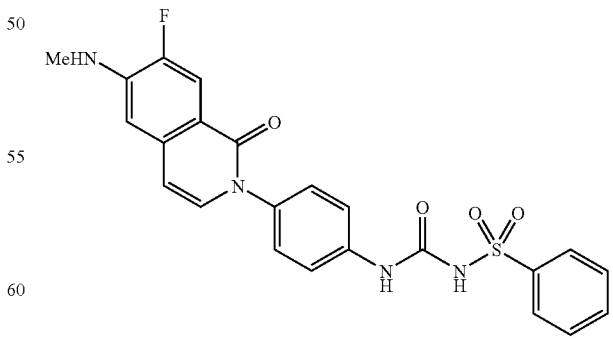

An analogous sulfonylurea coupling and de-protection procedure to that described in Example 29 was performed on [2-(4-Amino-phenyl)-7-fluoro-1-oxo-1,2-dihydro-isoquinolin-6-yl]-methyl-carbamic acid tert-butyl ester (Example 9)

and benzenesulfonamide to give N-({[4-(6-amino-7-fluoro-1-oxoisoquinolin-2(1H)-yl)phenyl]amino}carbonyl)-benzenesulfonamide. ES-MS (M+H)⁺=467.1; 1H-NMP (ΔMΣO-66) δ (ppm): 9.13-9.06 (bs, 1H), 7.98-7.92 (d, J=8.4 Hz, 2H), 7.70-7.56 (m, 4H), 7.44-7.37 (d, J=8.8 Hz, 2H), 7.39-7.24 (d, J=8.8 Hz, 2H), 7.21-7.18 (d, J=7.3 Hz, 1H), 6.74-6.66 (d, J=8.4 Hz, 1H), 6.56-6.48 (bs, 1H), 6.49-6.46 (d, J=7.7 Hz, 1H), 2.82-2.76 (bd, J=4.4 Hz, 3H).

Example 43

Trifluoromethanesulfonic Acid 7-fluoro-1-oxo-1,2-dihydro-isoquinolin-6-yl ester

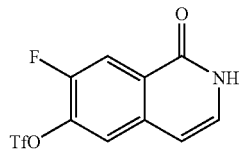

To a chilled suspension of 7-Fluoro-6-methoxy-2H-isoquinolin-1-one (from Example 3) (9.65 g, 50 mmol) in dichloromethane (200 mL) was added neat boron tribromide (21 mL, 220 mmol) via syringe. The yellow suspension was stirred at room temperature for 17 hr. The reaction was slowly poured into methanol (300 mL) on an ice bath. The resulting solution was concentrated in vacuo, washed and concentrated several times with methanol and dichloromethane, and dried to give 13 g of crude phenol. 1H-NMR (DMSO-d₆) δ (ppm): 6.38 (d, 1), 7.04 (m, 2), 7.73 (d, 1), 11.05 (s, 1).

To a suspension of 10.7 g of crude phenol in pyridine (160 mL) was added DMAP (7.6 g, 62.3 mmol) followed by phenyltrifluoromethylsulfonimide (17.4 g, 48.6 mmol) portionwise over approx. 5 min. The reaction mixture was stirred at room temperature for 1.5 hr, extracted into ethyl acetate (600 mL), washed with water (3×250 mL) and brine (250 mL). The organic layer was dried over sodium sulfate, filtered, concentrated and dried to give 24 g crude product, which was triturated with dichloromethane/hexane (2:1) to give 11.6 g (90% yield for 2 steps) of trifluoromethanesulfonic acid 7-fluoro-1-oxo-1,2-dihydro-isoquinolin-6-yl ester. 1H-NMR (DMSO-d₆) δ (ppm): 6.63-6.65 (s, 1), 7.26-7.29 (t, 1), 8.11-8.16 (m, 2), 11.61 (br s, 1).

Example 44

[7-Fluoro-1-oxo-2-(2-trimethylsilanyl-ethoxymethyl)-1,2-dihydro-isoquinolin-6-yl]-carbamic acid tert-butyl ester

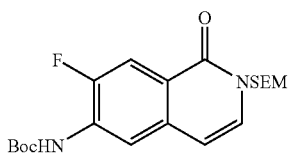

To a solution of trifluoromethane-sulfonic acid 7-fluoro-1-oxo-1,2-dihydro-isoquinolin-6-yl ester (10.5 g, 33.8 mmol) in THF (155 mL) at 0° C. was added neat 2-(trimethylsilyl)-ethoxymethyl chloride (SEM-Cl, 15 mL, 85 mmol) dropwise over 5 min, followed by neat DBU (19 mL, 127 mmol). The reaction slurry was stirred at room temperature for 2 hr, diluted with ethyl acetate (600 mL), washed with 0.25N HCl (200 mL), water (200 mL) and brine (250 mL), dried over Na₂SO₄, filtered, concentrated and dried to give crude product. Silica gel chromatography using 5-20% ethyl acetate/hexane as eluent gave 9.2 g (62%) of pure SEM-protected triflate. 1H-NMR (DMSO-d₆) δ (ppm): 0.085 (s, 9), 0.81-0.85 (d, 2), 3.53-3.57 (t, 2), 5.32 (s, 2), 6.72-6.74 (d, 1), 7.56-7.58 (d, 1), 8.12-8.14 (d, 1), 8.20-8.23 (d, 1).

In a dry flask was combined the triflate (9.2 g, 21 mmol), t-butyl carbamate (3.42 g, 29.2 mmol), dry powdered cesium carbonate (11.3 g, 34.7 mmol), 9,9-dimethyl-4,5-bis(diphenylphosphino)xanthene (Xantphos, 1.45 g, 2.5 mmol), and tris(dibenzylideneacetone)dipalladium(0) (Pd₂dba₃, 0.38 g, 0.83 mmol Pd). Under Ar atmosphere, dry THF (140 mL) was added to the flask, and the mixture was stirred at 70° C. for 3 hr. Upon cooling, the reaction was diluted with hexane (80 mL), filtered and concentrated to give 9.0 g crude product, which was purified by column chromatography (silica, 10-25% EtOAc/hexane) to give 6.1 g (72%) of pure [7-Fluoro-1-oxo-2-(2-trimethyl -silanyl-ethoxymethyl)-1,2-dihydro-isoquinolin-6-yl]-carbamic acid tert-butyl ester. ES-MS (M+H)⁺=409; 1H-NMR (DMSO-d₆) δ (ppm): −0.10 (s, 9), 0.80-0.84 (t, 2), 1.46 (s, 9), 3.51-3.55 (t, 2), 5.27 (s, 2), 6.58-6.60 (d, 1), 7.36-7.38 (d, 1), 7.82-7.85 (d, 1), 8.05-8.07 (d, 1), 9.45 (s, NH).

Example 45

(7-Fluoro-1-oxo-1,2-dihydro-isoquinolin-6-yl)-methyl-carbamic acid tert-butyl ester

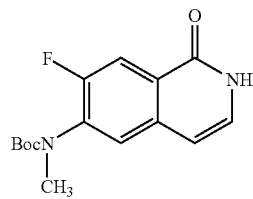

To a solution of [7-Fluoro-1-oxo-2-(2-trimethyl-silanyl-ethoxymethyl)-1,2-dihydro-isoquinolin-6-yl]-carbamic acid tert-butyl ester (5.95 g, 14.6 mmol) in dry dimethylformamide (50 mL) was added powdered cesium carbonate (12 g, 36.8 mmol) followed by neat methyl iodide (0.95 mL, 15.2 mmol). After 1 hr at room temperature the reaction was diluted with ethyl acetate (400 mL), washed with water (2×100 mL) and brine (100 mL), dried over Na₂SO₄, filtered, concentrated and dried to give crude methylated product. This crude material was dissolved in 1M tetrabutylammonium fluoride (85 mL in THF) and stirred at 65° C. for 2 hr. The reaction mixture was extracted into ethyl acetate (400 mL), washed with dilute HCl (100 mL), water (100 mL) and brine (100 mL), and dried to give a crude product, which was purified by column chromatography (silica, 40-70% EtOAc/dichloromethane) to give 3.34 g (78%) of pure (7-Fluoro-1-oxo-1,2-dihydro-isoquinolin-6-yl)-methyl-carbamic acid tert-butyl ester. ES-MS (M+H)⁺=293.1; 1H-NMR (DMSO-d₆) δ (ppm): 1.32 (s, 9), 3.17 (s, 3), 6.50-6.52 (d, 1), 7.13-7.16 (t, 1), 7.70-7.72 (d, 1), 7.81-7.84 (d, 1), 11.35 (br s, 1).

Example 46

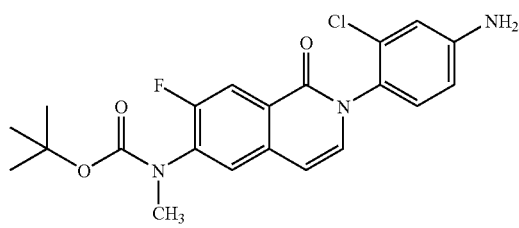

Method A: Using Substituted 4-fluoronitrobenzenes.

To a solution of (7-Fluoro-1-oxo-1,2-dihydro-isoquinolin-6-yl)-methyl-carbamic acid tert-butyl ester (Example 45) (70 mg, 0.24 mmol) and 3-chloro-4-fluoronitrobenzene (55 mg, 0.31 mmol, 1.3 eq) in dry dimethylformamide (2 mL) was added powdered cesium carbonate (0.2 g, 0.6 mmol, 2.5 eq). The mixture was stirred vigorously at 65-70° C. for 5 hr, then chilled on an ice bath. Addition of water precipitated out the desired product which upon filtration and drying under high vacuum gave 95 mg (89%) of pure nitro-aryl product. 1H-NMR (DMSO-$d_6$) δ (ppm): 1.34 (s, 9), 3.21 (s, 3), 6.76-6.78 (d, 1), 7.37-7.39 (d, 1), 7.84-7.85 (d, 1), 7.91-7.93 (d, 2), 8.34-8.36 (dd, 1), 8.54-8.55 (d, 1).

This nitro intermediate (89 mg, 0.2 mmol) was reduced by reaction with tin (II) dichloride dihydrate (134 mg, 0.6 mmol, 3 eq) in ethanol (3 mL) at 70° C. for 2 hr. Upon cooling, the reaction was diluted with ethyl acetate (20 mL), treated with Celite and 5% sodium bicarbonate (10 mL) to precipitate the tin (II) oxide. The Celite/$SnO_2$ was filtered off, and the organic layer washed with 5% $NaHCO_3$ (10 mL) and brine (10 mL), dried over $Na_2SO_4$, conc. in vacuo to gave 83 mg (100%) of the desired aniline [2-(4-Amino-2-chloro-phenyl)-7-fluoro-1-oxo-1,2-dihydro-isoquinolin-6-yl]-methyl-carbamic acid tert-butyl ester. ES-MS (M+H)$^+$= 418, 420 (Cl).

Example 47

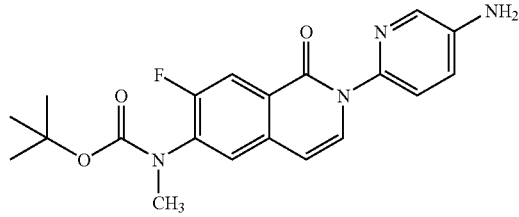

Method B: Using Substituted 4-halo-nitrobenzenes or 2-halo-5-nitropyridines.

In a dry flask was combined (7-Fluoro-1-oxo-1,2-dihydro-isoquinolin-6-yl)-methyl-carbamic acid tert-butyl ester (Example 45) (58 mg, 0.2 mmol), 2-bromo-5-nitropyridine (61 mg, 0.3 mmol, 1.5 eq), dry powdered cesium carbonate (113 mg, 0.35 mmol, 1.73 eq), 9,9-dimethyl-4,5-bis(diphenylphosphino)-xanthene (Xantphos, 15 mg, 0.026 mmol), and tris(dibenzylideneacetone)dipalladium(0) ($Pd_2$ $dba_3$, 4.5 mg, 0.01 mmol Pd). Under Ar atmosphere, dry THF (2 mL) was added to the flask, and the mixture was stirred at 80° C. for 2 hr. Upon cooling, the reaction was concentrated and the crude residue was purified by column chromatography (silica 2-15% EtOAc/dichloromethane) to give 68 mg (83%) of pure nitro-pyridyl product. 1H-NMR (DMSO-$d_6$) δ (ppm): 1.35 (s, 9), 3.21 (s, 3), 6.81-6.83 (d, 1), 7.84-7.85 (d, 1), 7.88-7.90 (d, 1), 7.99-8.01 (d, 1), 8.24-8.26 (d, 1), 8.76-8.79 (dd, 1), 9.39-9.40 (d, 1).

This nitro intermediate (67 mg, 0.16 mmol) was reduced under catalytic hydrogenation conditions using 1 atm $H_2$, 10% Pd/C (26 mg, 0.024 mmol Pd) in ethanol (2 mL) for 3 hr to give 60 mg (97%) of [2-(5-Amino-pyridin-2-yl)-7-fluoro-1-oxo-1,2-dihydro-isoquinolin-6-yl]-methyl-carbamic acid tert-butyl ester. ES-MS (M+H)$^+$=385.

Example 48

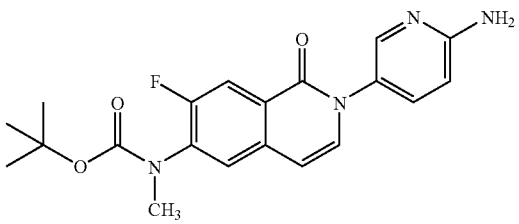

Method C: Using Substituted 4-haloanilines or 5-halo-2-aminopyridines and pyrimidines In a dry flask was combined (7-Fluoro-1-oxo-1,2-dihydro-isoquinolin-6-yl)-methyl-carbamic acid tert-butyl ester (Example 45, compound 10, Scheme B) (102 mg, 0.35 mmol), 2-amino-5-iodopyridine (84 mg, 0.38 mmol, 1.1 eq), copper (I) iodide (7 mg, 0.037 mmol, 0.11 eq), 8-hydroxyquinoline (6 mg, 0.041 mmol, 0.12 eq) and powdered potassium carbonate (58 mg, 0.42 mmol, 1.2 eq). Under Ar atmosphere, dry dimethylsulfoxide (DMSO, 1.5 mL) was added, and the mixture was stirred at 115° C. for 50 hr. The reaction was cooled, concentrated and purified by chromatography (silica, 2-15% isopropyl alcohol/dichloromethane) to give 67 mg (50%) of [2-(6-Amino-pyridin-3-yl)-7-fluoro-1-oxo-1,2-dihydro-isoquinolin-6-yl]-methyl-carbamic acid tert-butyl ester as a grey solid. ES-MS (M+H)$^+$=385. 1H-NMR (DMSO-d) δ (ppm): 1.33 (s, 9), 3.19 (s, 3), 6.25 (br m, $NH_2$), 6.53 (m, 1), 6.64-6.65 (d, 1), 7.37-7.39 (d, 1), 7.44-7.46 (d, 1), 7.77-7.79 (d, 1), 7.87-7.90 (d, 1), 7.95 (m, 1H).

Example 49

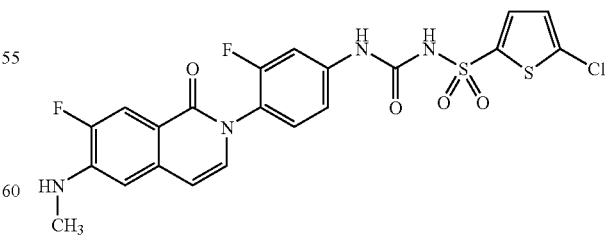

An analogous procedure to that outlined in Example 46 (Method A) using 3,4-difluoronitrobenzene was used to prepare the intermediate aniline. Formation of the sulfonyl urea was achieved using the method described in Example 13, followed by TFA de-protection, to give 5-chloro-N-[({3-fluoro-4-[7-fluoro-6-(methylamino)-1-oxoisoquinolin-2(1H)-yl]phenyl}amino)carbonyl]thiophene-2-sulfonamide. ES-MS (M+H)⁺=525, 527 (Cl).

Example 50

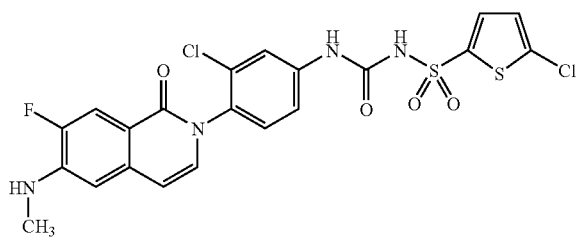

An analogous procedure to that outlined in Example 46 (Method A) using 3-chloro-4-fluoronitrobenzene, was used to prepare the intermediate aniline. Formation of the sulfonyl urea was achieved using the method described in Example 13, followed by TFA de-protection, to give 5-chloro-N-[({3-chloro-4-[7-fluoro-6-(methylamino)-1-oxoisoquinolin-2(1H)-yl]phenyl}amino)carbonyl]thiophene-2-sulfonamide. ES-MS (M+H)⁺=541, 543 (2Cl).

Example 51

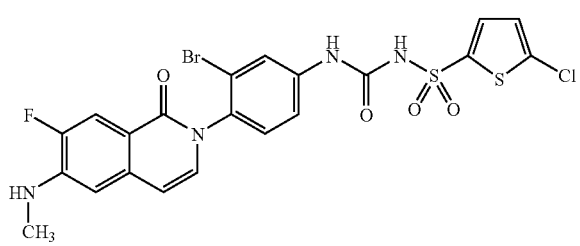

An analogous procedure to that outlined in Example 46 (Method A) using 3-bromo-4-fluoronitrobenzene was used to prepared the intermediate aniline. Formation of the sulfonyl urea was achieved using the method described in Example 13, followed by TFA de-protection, to give N-[({3-bromo-4-[7-fluoro-6-(methylamino)-1-oxoisoquinolin-2(1H)-yl]phenyl}amino)carbonyl]-5-chlorothiophene-2-sulfonamide. ES-MS (M+H)⁺=585, 587, 589 (BrCl).

Example 52

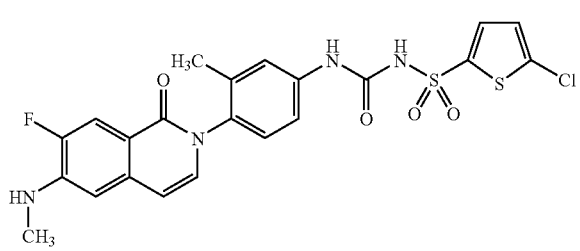

An analogous procedure to that outlined in Example 46 (Method A) using 4-fluoro-3-methylnitrobenzene was used to afford the substituted aniline. Formation of the sulfonyl urea was achieved using the method described in Example 13, followed by TFA deprotection, to give 5-chloro-N-[({4-[7-fluoro-6-(methylamino)-1-oxoisoquinolin-2(1H)-yl]-3-methylphenyl}amino)carbonyl]thiophene-2-sulfonamide. ES-MS (M+H)⁺=520, 522 (Cl).

Example 53

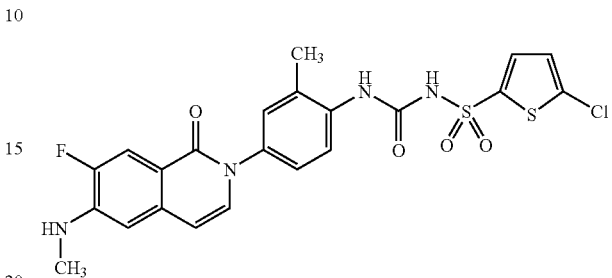

An analogous procedure to that outlined in Example 46 (Method A) using 4-fluoro-2-methylnitrobenzene was used to prepare the substituted aniline. Formation of the sulfonyl urea was achieved using the method described in Example 13, followed by TFA deprotection, to give 5-chloro-N-[({4-[7-fluoro-6-(methylamino)-1-oxoisoquinolin-2(1H)-yl]-2-methylphenyl}amino)carbonyl]thiophene-2-sulfonamide. ES-MS (M+H)⁺=520, 522 (Cl).

Example 54

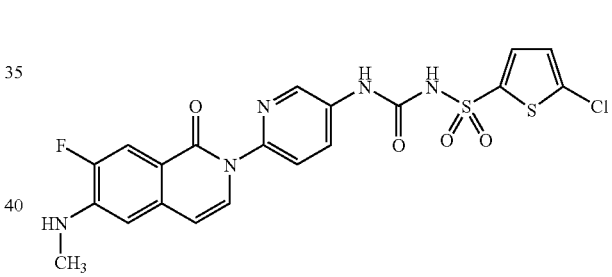

An analogous procedure to that outlined in Example 47 (Method B) using 2-bromo-5-nitropyridine was used to prepare the substituted aminopyridine. Formation of the sulfonyl urea was achieved using the method described in Example 13, followed by TFA deprotection, to give 5-chloro-N-[({6-[7-fluoro-6-(methylamino)-1-oxoisoquinolin-2(1H)-yl]pyridin-3-yl}amino)carbonyl]thiophene-2-sulfonamide. ES-MS (M+H)⁺=508, 510 (Cl).

Example 55

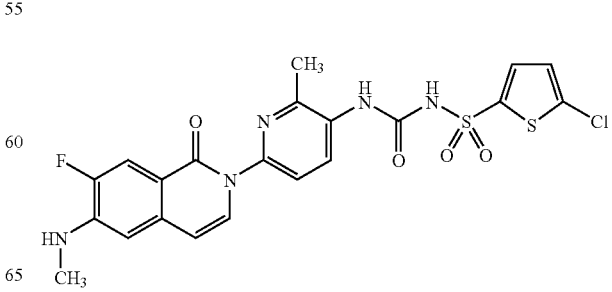

An analogous procedure to that outlined in Example 47 (Method B) using 2-chloro-5-nitro-6-methylpyridine was used to prepare the substituted aminopyridine. Formation of the sulfonyl urea was achieved using the method described in Example 13, followed by TFA deprotection, to give 5-chloro-N-[({6-[7-fluoro-6-(methylamino)-1-oxoisoquinolin-2(1H)-yl]-2-methylpyridin-3-yl}amino)carbonyl]thiophene-2-sulfonamide. ES-MS (M+H)$^+$=522, 524 (Cl).

Example 56

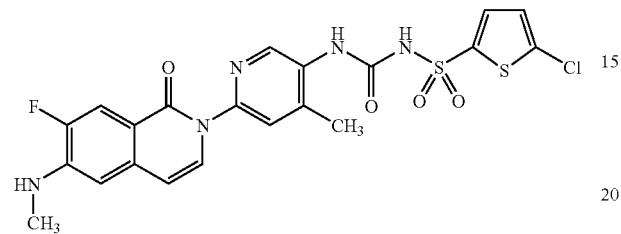

An analogous procedure to that outlined in Example 47 (Method B) using 2-chloro-4-methyl-5-nitropyridine was used to prepare the substituted aminopyridine. Formation of the sulfonyl urea was achieved using the method described in Example 13, followed by TFA deprotection, to give 5-chloro-N-[({6-[7-fluoro-6-(methylamino)-1-oxoisoquinolin-2(1H)-yl]-4-methylpyridin-3-yl}amino)carbonyl]thiophene-2-sulfonamide. ES-MS (M+H)$^+$=522, 524 (Cl).

Example 57

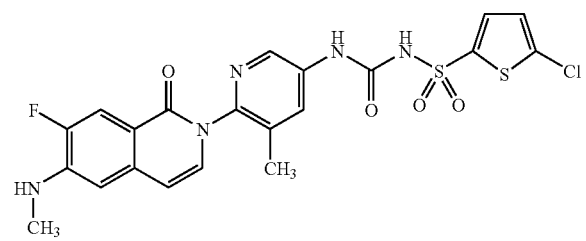

An analogous procedure to that outlined in Example 47 (Method B) using 2-chloro-3-methyl-5-nitropyridine was used to prepare the substituted aminopyridine. Formation of the sulfonyl urea was achieved using the method described in Example 13, followed by TFA deprotection, to give 5-chloro-N-[({6-[7-fluoro-6-(methylamino)-1-oxoisoquinolin-2(1H)-yl]-5-methylpyridin-3-yl}amino)carbonyl]thiophene-2-sulfonamide. ES-MS (M+H)$^+$=522, 524 (Cl).

Example 58

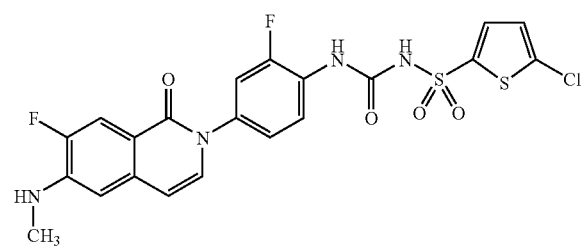

An analogous procedure to that outlined in Example 48 (Method C) using 2-fluoro-4-iodoaniline was used to prepare the substituted aniline. Formation of the sulfonyl urea was achieved using the method described in Example 13, followed by TFA deprotection, to give 5-chloro-N-[({2-fluoro-4-[7-fluoro-6-(methylamino)-1-oxoisoquinolin-2(1H)-yl]phenyl}amino)carbonyl]thiophene-2-sulfonamide. ES-MS (M+H)$^+$=525, 527 (Cl).

Example 59

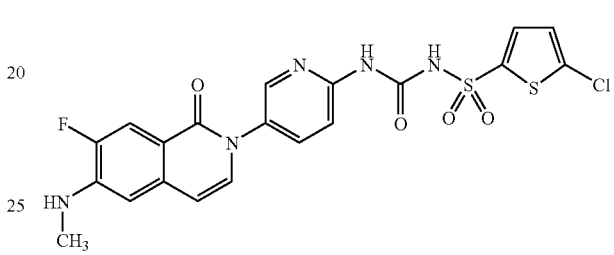

An analogous procedure to that outlined in Example 48 (Method C) using 2-amino-5-bromopyridine was used to prepare the intermediate aminopyridine. Formation of the sulfonyl urea was achieved using the method described in Example 13, followed by TFA deprotection, to give 5-chloro-N-[({5-[7-fluoro-6-(methylamino)-1-oxoisoquinolin-2(1H)-yl]pyridin-2-yl}amino)carbonyl]thiophene-2-sulfonamide. ES-MS (M+H)$^+$=508, 510 (Cl).

Example 60

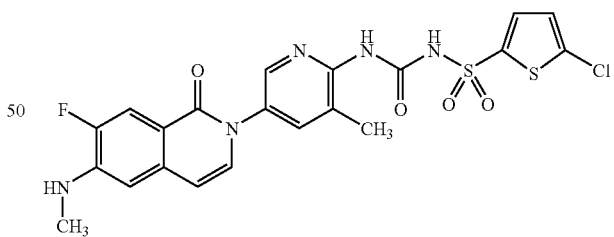

An analogous procedure to that outlined in Example 48 (Method C) using 2-amino-3-methyl-5-bromopyridine was used to prepare the substituted aniline. Formation of the sulfonyl urea was achieved using the method described in Example 13, followed by TFA deprotection, to give 5-chloro-N-[({5-[7-fluoro-6-(methylamino)-1-oxoisoquinolin-2(1H)-yl]-3-methylpyridin-2-yl}amino)carbonyl]thiophene-2-sulfonamide. ES-MS (M+H)$^+$=521, 523 (Cl).

Example 61

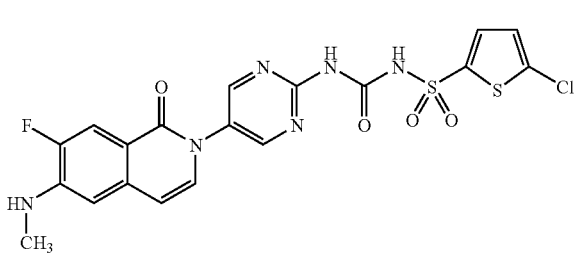

An analogous procedure to that outlined in Example 48 (Method C) using 2-amino-5-iodopyrimidine was used to prepare the intermediate aminopyrimidine. Formation of the sulfonyl urea was achieved using the method described in Example 13, followed by TFA deprotection, to give 5-chloro-N-[({5-[7-fluoro-6-(methylamino)-1-oxoisoquinolin-2(1H)-yl]pyrimidin-2-yl}amino)carbonyl]thiophene-2-sulfonamide. ES-MS (M+H)$^+$=509, 511(Cl).

Example 62

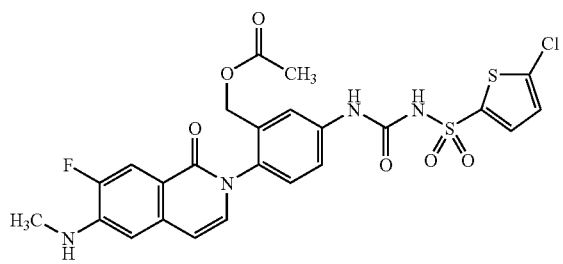

To a solution of 2-fluoro-5-nitrobenzyl alcohol (1 g, 5.84 mmol) in 5 mL dichloromethane and triethylamine (0.81 ml, 5.84 mmol), was added acetyl chloride (0.415 ml, 1 eq) dropwise. The solution was stirred at room temperature for 12 hours, diluted with ethyl acetate and extracted with brine. Combine organic layers was dried over sodium sulfate, concentrated in vacuo to give acetic acid 2-fluoro-5-nitrobenzyl ester.

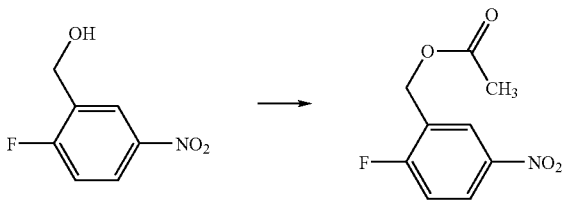

Acetic acid 2-fluoro-5-nitro-benzyl ester was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-[({[(5-chlorothien-2-yl)sulfonyl]amino}carbonyl)amino]-2-[7-fluoro-6-(methylamino)-1-oxoisoquinolin-2(1H)-yl]benzyl acetate. ES-MS (M+H)$^+$=579, 581(Cl).

Example 63

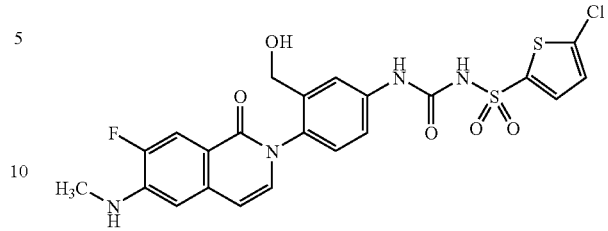

This analog compound was obtained from hydrolysis of the intermediate, Boc protected compound of Example 62, then followed by TFA deprotection to give 5-chloro-N-({[4-[7-fluoro-6-(methylamino)-1-oxoisoquinolin-2(1H)-yl]-3-(hydroxymethyl)phenyl]amino}carbonyl)thiophene-2-sulfonamide. ES-MS (M+H)$^+$=537, 539(Cl).

Example 64

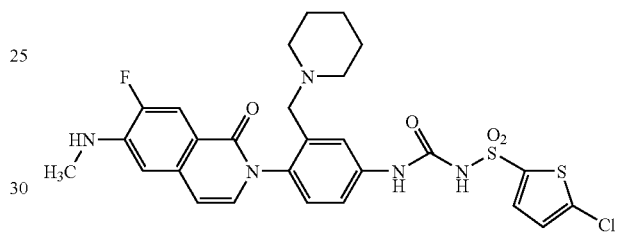

To a solution of 2-fluoro-5-nitrobenzyl alcohol (1 g, 5.84 mmol) in 25 mL ether, was added tetrabromomethane (3.87 g, 11.7 mmol), followed by triphenylphosphine (3.39 g, 11.7 mmol). The mixture was stirred at room temperature for 2 hours. The reaction was concentrated and the crude residue purified by column chromatography (silica, 10% EtOAc/hexane) to give pure 2-bromomethyl-1-fluoro-4-nitro-benzene.

To a solution of 2-bromomethyl-1-fluoro-4-nitro-benzene (0.2 g, 0.85 mmol) in 5 mL dry THF, was added piperidine (0.11 ml, 1 mmol) and DIEA (0.3 ml, 1.7 mmol) at 0° C. The resulting reaction was stirred at 0° C. to room temperature for 1 hour, then diluted with EtOAc and washed with brine. Combined organic layer was dried over sodium sulfate, concentrated in vacuo and the crude residue was purified by column chromatography (10% EtOAc/hexane) to give pure 1-(2-fluoro-5-nitro-benzyl)piperidinebenzene.

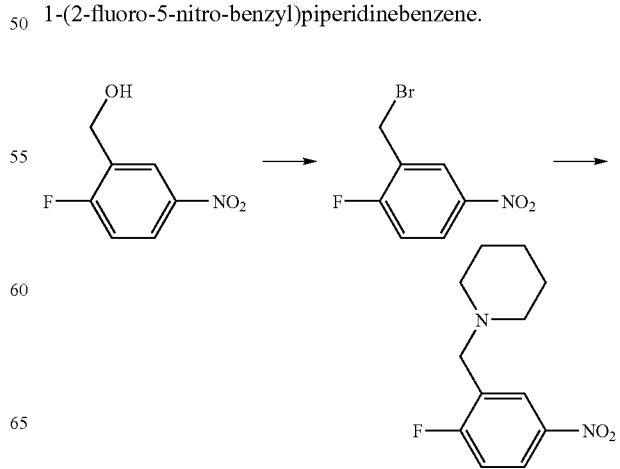

1-(2-Fluoro-5-nitro-benzyl)piperidinebenzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-3-(piperidin-1-ylmethyl)phenyl]amino}carbonyl)thiophene-2-sulfonamide. ES-MS (M+H)⁺=604, 606(Cl).

Example 65

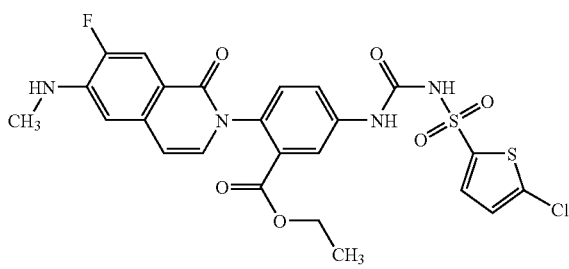

To a solution of 2-fluoro-5-nitro-benzoic acid (0.269 g, 1.45 mmol) in 3 mL ethanol, was added concentrated sulfuric acid (0.5 ml). The solution was refluxed under argon for 3 hours. The mixture was stirred at room temperature for 2 hours, then diluted with ethyl acetate and washed with brine. The organic layer was dried over sodium sulfate, concentrated in vacuo to give pure 2-fluoro-5-nitro-benzoic acid ethyl ester.

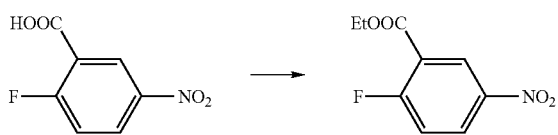

2-Fluoro-5-nitro-benzoic acid ethyl ester was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give ethyl 5-[({[(5-chlorothien-2-yl)sulfonyl]amino}carbonyl)amino]-2-[7-fluoro-6-(methylamino)-1-oxoisoquinolin-2(1H)-yl]benzoate. ES-MS (M+H)⁺=579, 581(Cl).

Example 66

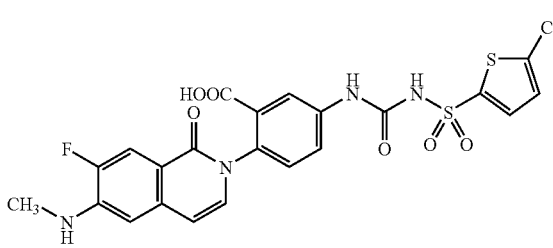

This analog compound was obtained from hydrolysis of ethyl 5-[({[(5-chlorothien-2-yl)sulfonyl]amino}carbonyl)amino]-2-[7-fluoro-6-(methylamino)-1-oxoisoquinolin-2(1H)-yl]benzoate of Example 65 using the procedure described in Example 63. 5-[({[(5-chlorothien-2-yl)sulfonyl]amino}carbonyl)amino]-2-[7-fluoro-6-(methylamino)-1-oxoisoquinolin-2(1H)-yl]benzoic acid. ES-MS (M+H)⁺= 551, 553(Cl).

Example 67

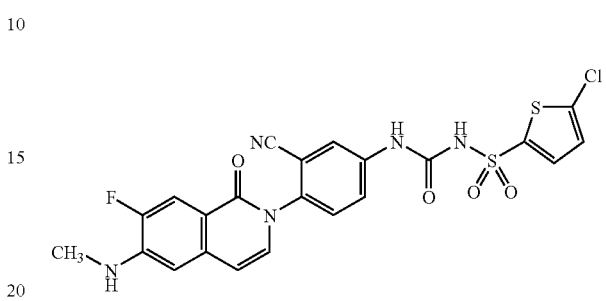

The substituted aniline was generated by Method A (Example 46) using 2-fluoro-5-nitro-benzonitril. Formation of the sulfonyl urea was achieved using the method described in Example 10, followed by TFA deprotection, to give 5-chloro-N-[({3-cyano-4-[7-fluoro-6-(methylamino)-1-oxoisoquinolin-2(1H)-yl]phenyl}amino)carbonyl]thiophene-2-sulfonamide. ES-MS (M+H)⁺=532, 534 (Cl).

Example 68

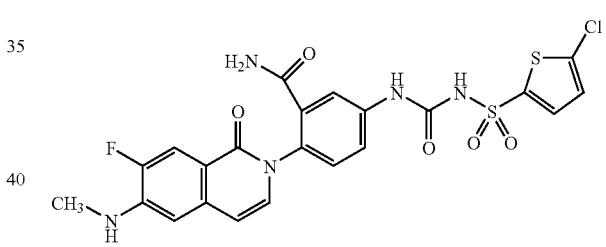

This analog compound was obtained during the TFA de-protection step in Example 67. 5-[({[(5-chlorothien-2-yl)sulfonyl]amino}carbonyl)amino]-2-[7-fluoro-6-(methylamino)-1-oxoisoquinolin-2(1H)-yl]benzamide. ES-MS (M+H)⁺=550, 552 (Cl).

Example 69

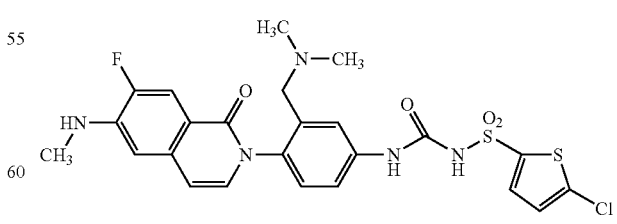

To a solution of 2-bromomethyl-1-fluoro-4-nitro-benzene (131 mg, 0.56 mmol), which was generated in Example 64) and dimethylamine hydrochloride (44 mg, 0.54 mmol) in 4 mL dioxane, was added cesium carbonate (546 mg, 1.68 mmol). The mixture was heated to 70° C. under argon for 12 hours. Work up and RP prep HPLC to give (2-fluoro-5-nitro-benzyl)-dimethyl-amine.

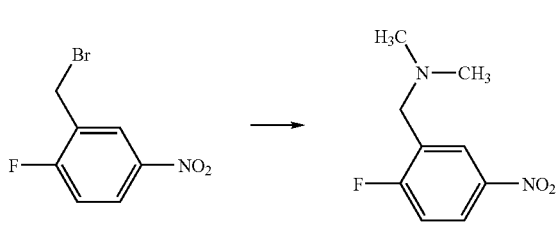

(2-Fluoro-5-nitro-benzyl)-dimethyl-amine was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[(f{3-[(dimethylamino)methyl]-4-[7-fluoro-6-(methylamino)-1-oxoisoquinolin-2(1H)-yl]phenyl}amino)carbonyl]thiophene-2-sulfonamide. ES-MS (M+H)$^+$=564, 566(Cl).

Example 70

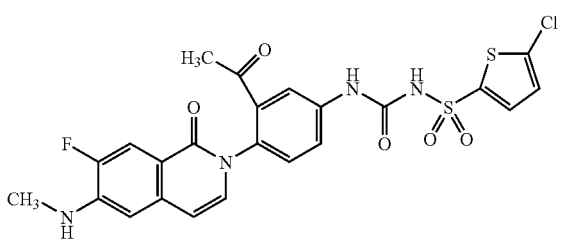

To a solution of 3-bromo-4-fluoronitrobenzene (696 mg, 3.16 mmol) and tributyl(1-ethoxyvinyl)tin (1.07 ml, 3.5 mmol) in 10 mL toluene, was added tetrakis(triphenylphosphine)palladium(0) (183 mg, 016 mmol). The mixture was purged with argon for 3 minutes, and then heated to 110° C. under argon for 2 days. The reaction mixture was cooled to room temperature, 3 mL 1 N HCl was added and stirred at room temperature for 40 minutes. Workup followed by column chromatographic purification (silica 10%-30% EtOAc/hexane) to give pure 1-(2-fluoro-5-nitro-phenyl)-ethanone.

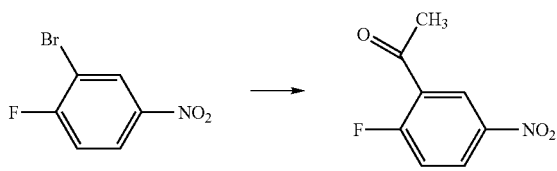

1-(2-fluoro-5-nitro-phenyl)-ethanone was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give N-[({3-acetyl-4-[7-fluoro-6-(methylamino)-1-oxoisoquinolin-2(1H)-yl]phenyl}amino)carbonyl]-5-chlorothiophene-2-sulfonamide. ES-MS(M+H)$^+$=549, 551 (Cl).

Example 71

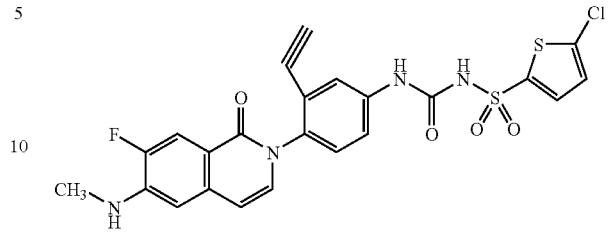

A mixture of bis(benzonitril)dichloropalladium(II) (53 mg, 0.14 mmol) and copper (I) iodide (26 mg, 0.14 mmol) in 6 mL dry THF was purged with argon for 3 minutes, then was added tri(tert-butyl phosphine) (69 ul, 0.28 mmol), TMS acetylene (0.77 ml, 5.5 mmol), 3-bromo-4-fluoronitrobenzene 505 mg, 2.295 mmol), and di-isopropylamine (0.77 ml, 5.5 mmol). The mixture was stirred at room temperature for 5 hours under argon. To the reaction mixture was added 7 mL 1 M TBAF/THF and the mixture was stirred at room temperature for 10 minutes. Workup and purification by column chromatography (silica, 5%-35% EtOAc/hexane) give 2-ethynyl-1-fluoro-4-nitro-benzene.

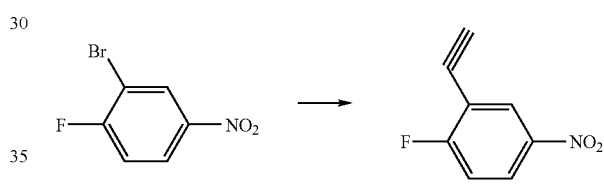

2-Ethynyl-1-fluoro-4-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({3-ethynyl-4-[7-fluoro-6-(methylamino)-1-oxoisoquinolin-2(1H)-yl]phenyl}amino)carbonyl]thiophene-2-sulfonamide. ES-MS (M+H)$^+$=531, 533 (Cl).

Example 72

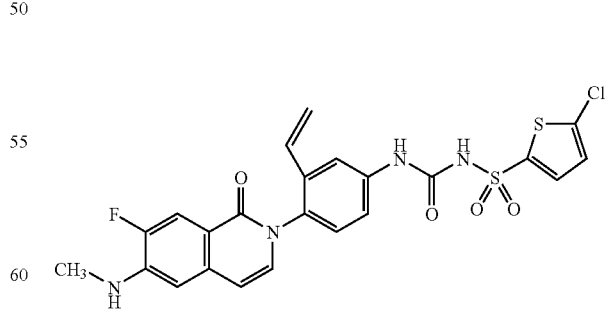

To a solution of 2-ethynyl-1-fluoro-4-nitro-benzene (70 mg, 0.42 mmol, obtained in Example 71) in 3 mL ethanol, 5% Pd/BaSO4 (48 mg) was added. The mixture was hydrogenated at 1 atm for 1.5 hrs. Catalyst was removed by filtering through a celite pad. The filtrate was concentrated to give pure 1-fluoro-4-nitro-2-vinyl-benzene.

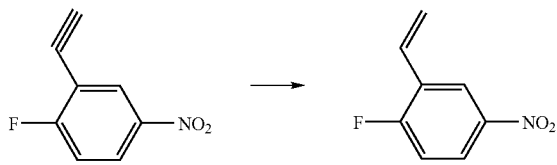

1-Fluoro-4-nitro-2-vinyl-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-3-vinylphenyl}amino)carbonyl]thiophene-2-sulfonamide. ES-MS (M+H)+=533, 535(Cl).

Example 73

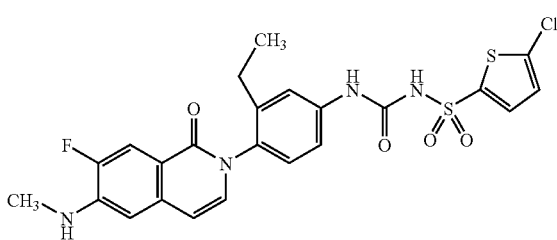

To a solution of [7-fluoro-2-(4-nitro-2-vinyl-phenyl)-1-oxo-1,2-dihydro-isoquinolin-6-yl]-methyl-carbamic acid tert-butyl ester (60 mg, 0.137 mmol, the intermediate material generated in Example 72) in 1.5 mL ethanol and 2.5 mL ethylacetate, 5% Pd/C (60 mg) was added and the mixture was hydrogenated at 1 atm for 10 hrs. Catalyst was removed by filtering through a celite pad. The filtrate was concentrated to give desired aniline.

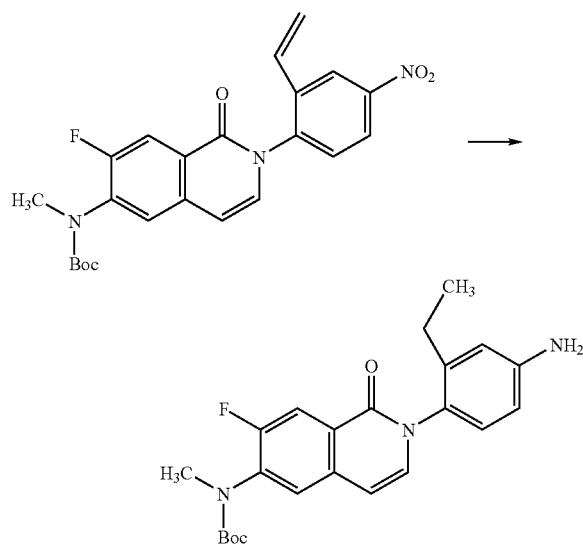

Formation of the sulfonyl urea was achieved using the method described in Example 10, followed by TFA deprotection, to give 5-chloro-N-[({3-ethyl-4-[7-fluoro-6-(methylamino)-1-oxoisoquinolin-2(1H)-yl]phenyl}amino)carbonyl]thiophene-2-sulfonamide. ES-MS (M+H)+=535, 537(Cl).

Example 74

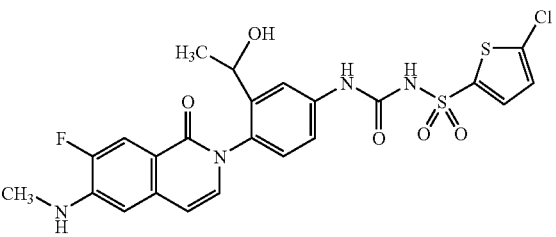

This analog compound was obtained from reduction of N-[({3-acetyl-4-[7-fluoro-6-(methylamino)-1-oxoisoquinolin-2(1H)-yl]phenyl}amino)carbonyl]-5-chlorothiophene-2-sulfonamide of Example 70. To a solution of N-[({3-acetyl-4-[7-fluoro-6-(methylamino)-1-oxoisoquinolin-2(1H)-yl]phenyl}amino)carbonyl]-5-chlorothiophene-2-sulfonamide (18 mg, 0.033 mmol) in 2 mL ethanol, was added sodium borohydride (20 mg, 0.53 mmol). The mixture was stirred at room temperature for 30 minutes. Workup and purification provided 5-chloro-N-({[4-[7-fluoro-6-(methylamino)-1-oxoisoquinolin-2(1H)-yl]-3-(1-hydroxyethyl)phenyl]amino}carbonyl)thiophene-2-sulfonamide as a mixture of rotamers. ES-MS (M+H)+=551, 553(Cl).

Example 75

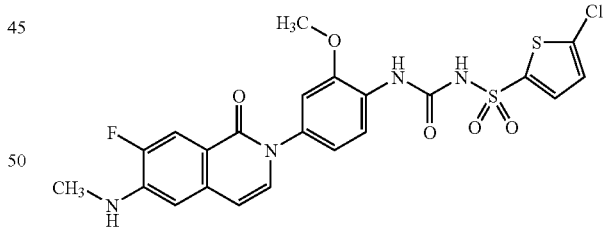

To a solution of 5-fluoro-2-nitro-phenol (369 mg, 2.35 mmol) in 5 mL THF, sodium hydride (96 mg, 2.46 mmol) was added at room temperature, followed by methyl iodide (0.88 ml, 14 mmol). The mixture was stirred at room temperature for 10 hours, and then cesium carbonate (744 mg, 2.35 mmol) was added. The mixture was stirred at room temperature for additional 4 hours, then diluted with ethyl acetate and washed with brine. The organic layers were combined and concentrated in vacuo to give a crude residue, which was purified by column chromatography (silica 5-25% EtOAc/hexane) to give pure 4-fluoro-2-methoxy-1-nitro-benzene.

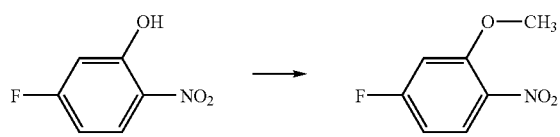

4-Fluoro-2-methoxy-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2-methoxyphenyl}amino)carbonyl]thiophene-2-sulfonamide. ES-MS (M+H)$^+$=537, 539 (Cl).

Example 76

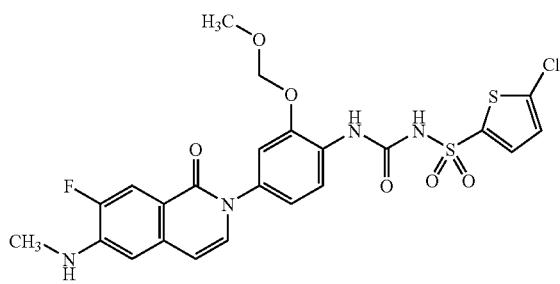

To a solution of 5-fluoro-2-nitro-phenol (234 mg, 1.49 mmol) in 5 mL THF, sodium hydride (122 mg, 2.9 mmol) was added, followed by chloromethoxy methane (113 ul, 1.49 mmol) at 0° C. The mixture was warmed to room temperature and stirred for 10 hours, then diluted with ethyl acetate and washed with brine. The organic layers were combined and concentrated in vacuo to give a crude residue, which was purified by column chromatography (silica 5-25% EtOAc/hexane) to give 4-fluoro-2-methoxymethoxy-1-nitro-benzene.

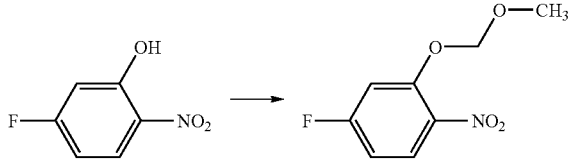

4-Fluoro-2-methoxymethoxy-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(methoxymethoxy)phenyl]amino}carbonyl)thiophene-2-sulfonamide. ES-MS (M+H)$^+$=567, 569(Cl).

Example 77

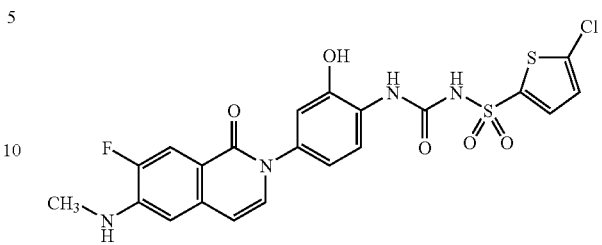

This analog compound was obtained from TFA deprotection step in Example 76. 5-chloro-N-[({4-[7-fluoro-6-(methylamino)-1-oxoisoquinolin-2(1H)-yl]-2-hydroxyphenyl}amino)carbonyl]thiophene-2-sulfonamide. ES-MS (M+H)$^+$=523, 525(Cl).

Example 78

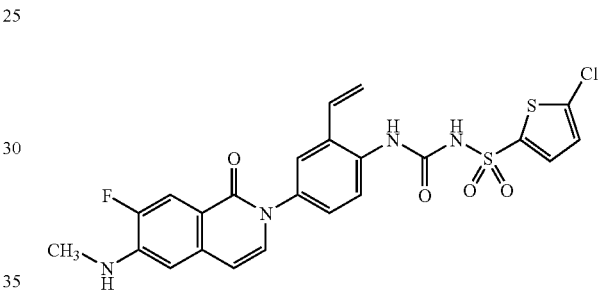

2-Ethynyl-4-fluoro-1-nitro-benzene was obtained from 2-bromo-4-fluoro-1-nitro-benzene using the procedure described in Example 71.

4-Fluoro-1-nitro-2-vinyl-benzene was obtained using 2-ethynyl-4-fluoro-1-nitro-benzene using the procedure described in Example 72.

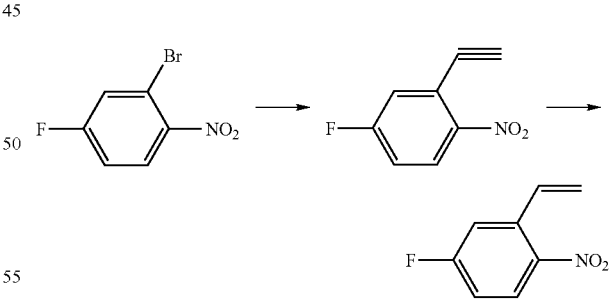

4-Fluoro-1-nitro-2-vinyl-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2-vinylphenyl}amino)carbonyl]thiophene-2-sulfonamide. ES-MS (M+H)$^+$=533, 535(Cl).

Example 79

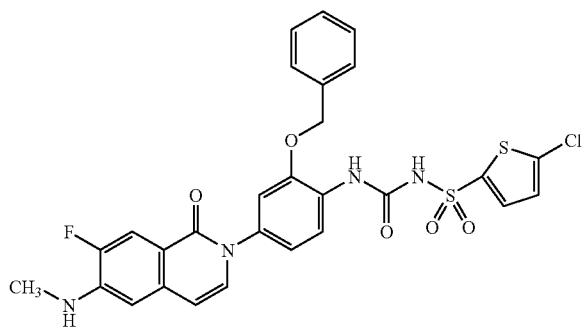

A mixture of 5-fluoro-2-nitro-phenol (464 mg, 2.95 mmol), benzyl bromide (0.37 ml, 3.10 mmol) and cesium carbonate (1.055 g, 3.24 mmol) in MeCN (10 mL) was stirred room temperature under argon for 48 hours. The reaction mixture was diluted with ethyl acetate and washed with brine. The organic layers were combined and concentrated in vacuo to give a crude residue, which was purified by column chromatography (silica 5-25% EtOAc/hexane) to give 2-benzyloxy-4-fluoro-1-nitro-benzene.

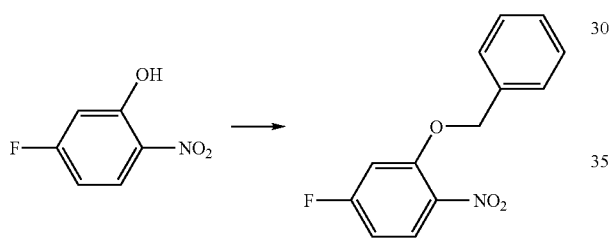

2-Benzyloxy-4-fluoro-1-nitro-benzene was coupled to (7-Fluoro-1-oxo-1,2-dihydro-isoquinolin-6-yl)-methyl-carbamic acid tert-butyl ester using Method A (Example 46).

Formation of the sulfonyl urea was achieved using the method described in Example 10, followed by TFA deprotection, to give N-[({2-(benzyloxy)-4-[7-fluoro-6-(methylamino)-1-oxoisoquinolin-2(1H)-yl]phenyl}amino)carbonyl]-5-chlorothiophene-2-sulfonamide. ES-MS (M+H)+ =613, 615(Cl).

Example 80

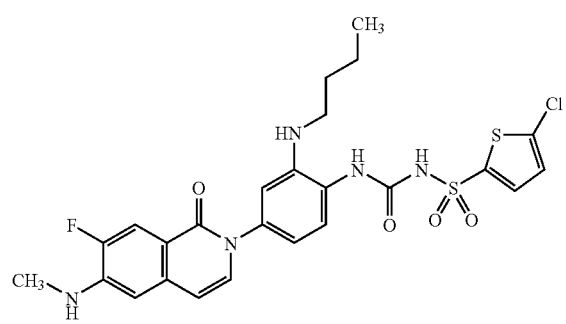

[2-(3-Bromo-4-nitro-phenyl)-7-fluoro-1-oxo-1,2-dihydro-isoquinolin-6-yl]-methyl-carbamic acid tert-butyl ester was generated by Method A (Example 46) using 2-bromo-4-fluoro-1-nitro-benzene. A mixture of [2-(3-Bromo-4-nitro-phenyl)-7-fluoro-1-oxo-1,2-dihydro-isoquinolin-6-yl]-methyl-carbamic acid tert-butyl ester (21 mg, 0.0427 mmol), tetrakis(triphenylphosphine)palladium(0) (2.5 mg, 0.002 mmol), copper (I) iodide (2 mg, 0.008 mmol), TMS acetylene (10 ul, 0.07 mmol), n-butylamine (1.5 ml) and 1 mL DMF was purged with argon for 2 minutes. The mixture was then subjected to microwave irradiation (120° C.) for 5 minutes, then diluted with ethyl acetate and washed with brine. The organic layers were combined and concentrated in vacuo to give a crude residue, which was purified by column chromatography (silica 5-25% EtOAc/hexane) to give [2-(3-butylamino-4-nitro-phenyl)-7-fluoro-1-oxo-1,2-dihydro-isoquinolin-6-yl]-methyl-carbamic acid tert-butyl ester.

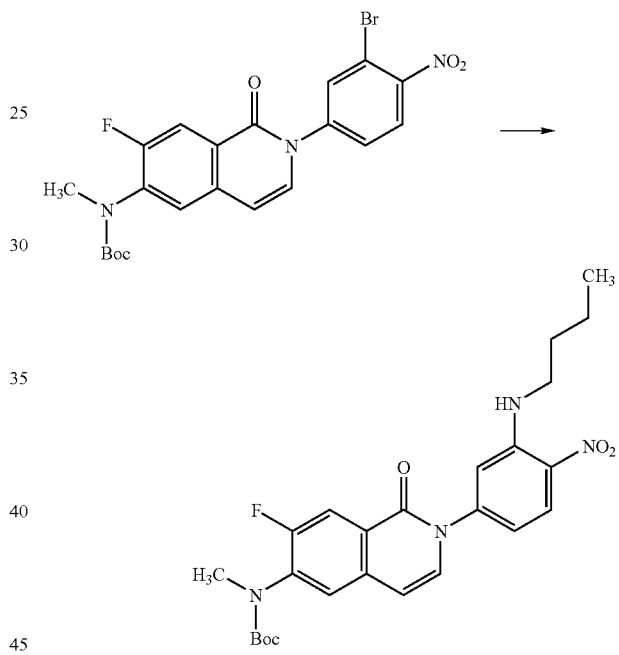

Reduction of the nitro group, sulfonyl urea formation, followed by TFA deprotection, provided N-[({2-(butylamino)-4-[7-fluoro-6-(methylamino)-1-oxoisoquinolin-2(1H)-yl]phenyl}amino)carbonyl]-5-chlorothiophene-2-sulfonamide. ES-MS (M+H)+=578, 580(Cl).

Example 81

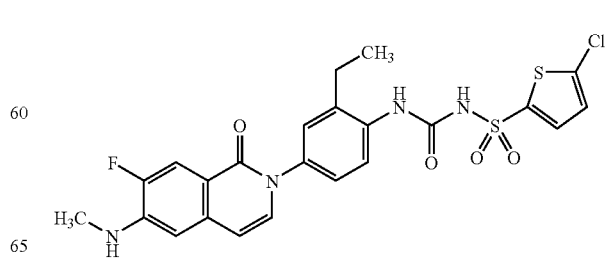

This analog compound was obtained from [7-fluoro-2-(4-nitro-3-vinyl-phenyl)-1-oxo-1,2-dihydro-isoquinolin-6-yl]-methyl-carbamic acid tert-butyl ester (intermediate in Example 78) using the reduction procedure described in Example 73.

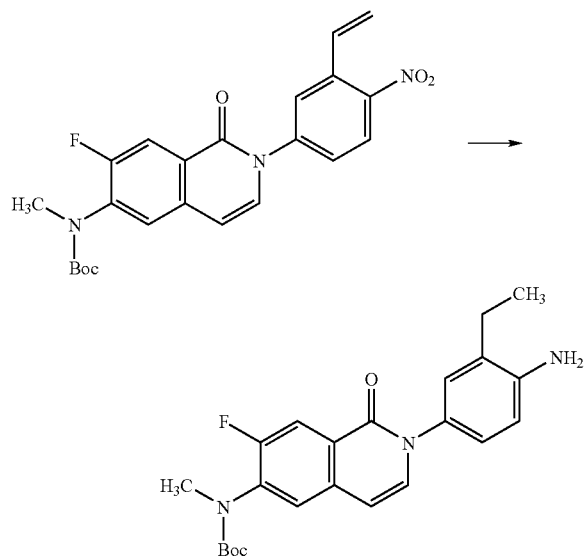

Formation of the sulfonyl urea was achieved using the method described in Example 10, followed by TFA deprotection, to give 5-chloro-N-[({2-ethyl-4-[7-fluoro-6-(methylamino)-1-oxoisoquinolin-2(1H)-yl]phenyl}amino)carbonyl]thiophene-2-sulfonamide. ES-MS (M+H)⁺=535, 537(Cl).

Example 82

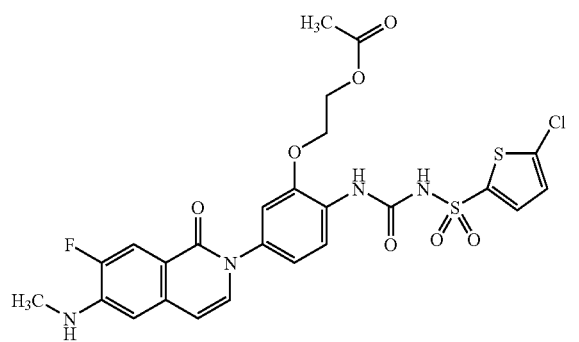

Acetic acid 2-(5-fluoro-2-nitro-phenoxy)-ethyl ester was obtained starting with acetic acid 2-bromo-ethyl ester and using the procedure described in Example 79.

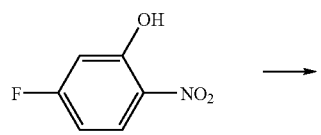

-continued

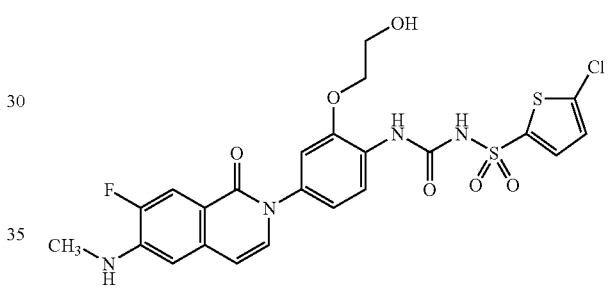

Acetic acid 2-(5-fluoro-2-nitro-phenoxy)-ethyl ester was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 2-{2-[({[(5-chlorothien-2-yl)sulfonyl]amino}carbonyl)amino]-5-[7-fluoro-6-(methylamino)-1-oxoisoquinolin-2(1H)-yl]phenoxy}ethyl acetate. ES-MS (M+H)⁺=609, 611(Cl).

Example 83

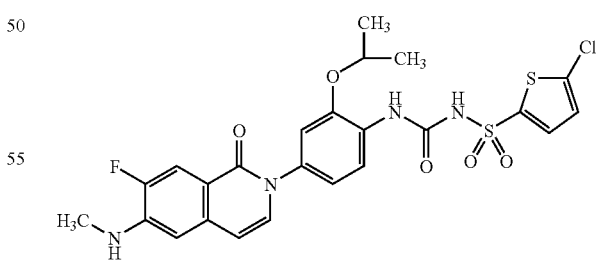

This analog compound was obtained from hydrolysis (as described in Example 63) of the intermediate Boc protected compound of Example 82, followed by TFA deprotection. 5-chloro-N-({[4-[7-fluoro-6-(methylamino)-1-oxoisoquinolin-2(1H)-yl]-2-(2-hydroxyethoxy)phenyl]amino}carbonyl)thiophene-2-sulfonamide. ES-MS (M+H)⁺=567, 569(Cl).

Example 84

4-Fluoro-2-isopropoxy-1-nitro-benzene was obtained using 5-fluoro-2-nitro-phenol and isopropanol under Mitsunobu reaction condition. The general procedure is described as follows: to a solution of 4-fluoro-2-isopropoxy-1-nitro-benzene (313 mg, 1.99 mmol), triphenylphosphine (783 mg, 2.98 mmol) and ispropanol (161 mg, 2.59 mmol) in 2 mL THF, was added diethyl azodicarboxylate (0.49 ml, 2.99 mmol) dropwise at 0° C. The mixture was warmed to room temperature and stirred for 30 minutes, then diluted with ethyl acetate and washed with brine. The organic layers were combined and concentrated in vacuo to give a crude residue, which was purified by column chromatography (silica 5-25% EtOAc/hexane) to give 4-fluoro-2-isopropoxy-1-nitro-benzene.

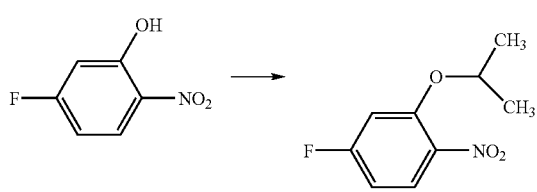

4-Fluoro-2-isopropoxy-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2-isopropoxyphenyl}amino)carbonyl]thiophene-2-sulfonamide. ES-MS (M+H)$^+$=565, 567(Cl).

Example 85

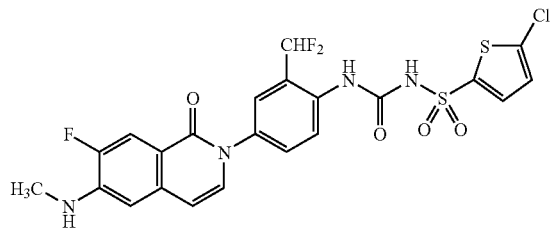

To a solution of 5-fluoro-2-nitro-benzaldehyde (573 mg, 3.39 mmol) in 4 mL DCM, was added (diethylamino)sulfurtrifluride (0.448 ml, 3.39 mmol) dropwise at 0° C. over 3 minutes. The reaction mixture was stirred at 0° C. for 1 hour, then diluted with dichloromethane and washed with brine. The organic layers were combined and concentrated in vacuo to give a crude residue, which was purified by column chromatography (silica 15-40% EtOAc/hexane) to give 2-difluoromethyl-4-fluoro-1-nitro-benzene.

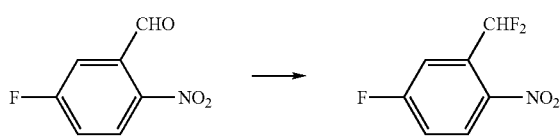

2-Difluoromethyl-4-fluoro-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to 5-chloro-N-[({2-(difluoromethyl)-4-[7-fluoro-6-(methylamino)-1-oxoisoquinolin-2(1H)-yl]phenyl}amino)carbonyl]thiophene-2-sulfonamide. ES-MS (M+H)$^+$=557, 559(Cl).

Example 86

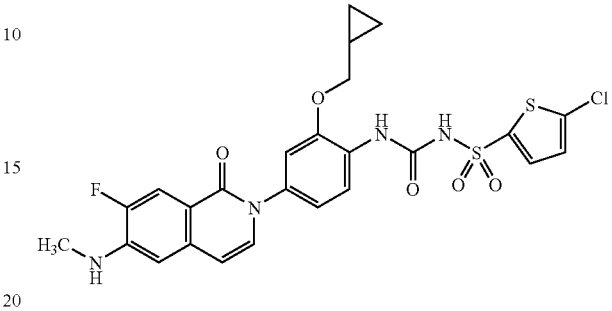

2-Cyclopropylmethoxy-4-fluoro-1-nitro-benzene was obtained from cyclopropyl methanol using the procedure described in Example 84.

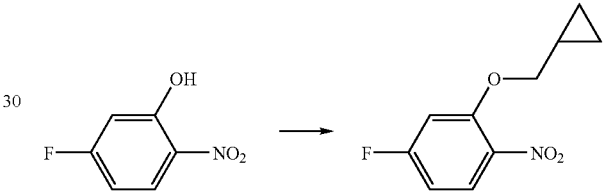

2-Cyclopropylmethoxy-4-fluoro-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to 5-chloro-N-[({2-(cyclopropylmethoxy)-4-[7-fluoro-6-(methylamino)-1-oxoisoquinolin-2(1H)-yl]phenyl}amino)carbonyl]thiophene-2-sulfonamide. ES-MS (M+H)$^+$=577, 579(Cl).

Example 87

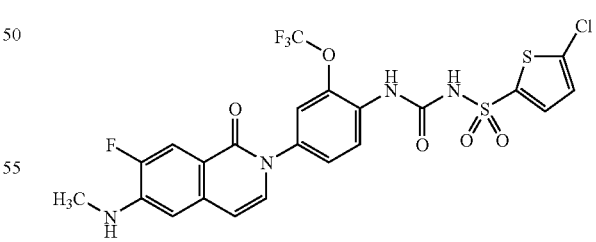

The substituted aniline was generated by Method C (Example 48) using 4-bromo-2-trifluoromethoxy-phenylamine. Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(trifluoromethoxy)phenyl]amino}carbonyl)thiophene-2-sulfonamide. ES-MS (M+H)$^+$=591, 593(Cl).

Example 88

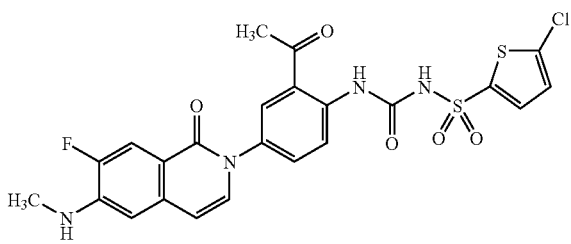

1-(5-Fluoro-2-nitro-phenyl)-ethanone was obtained using 2-bromo-4-fluoro-1-nitro-benzene with the procedure described in Example 70.

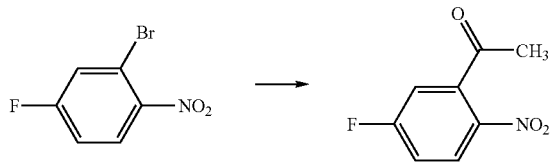

1-(5-fluoro-2-nitro-phenyl)-ethanone was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give N-[({2-acetyl-4-[7-fluoro-6-(methylamino)-1-oxoisoquinolin-2(1H)-yl]phenyl}amino)carbonyl]-5-chlorothiophene-2-sulfonamide. ES-MS (M+H)⁺=549, 551 (Cl).

Example 89

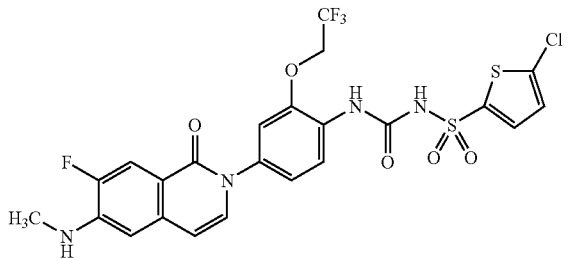

To a solution of trifluoroethanol in 4 mL dry THF, was added tert-butoxide (378 mg, 3.37 mmol) at 0° C. The resulting mixture was added dropwise to the solution of 2,4-difluoro-1-nitro-benzene (536 mg, 3.37 mmol) in 5 mL dry THF at 0° C. The mixture was stirred at 0° C. for 30 minutes, then diluted with ethyl acetate and washed with brine. The organic layers were combined and concentrated in vacuo to give 4-fluoro-1-nitro-2-(2,2,2-trifluoro-ethoxy)-benzene.

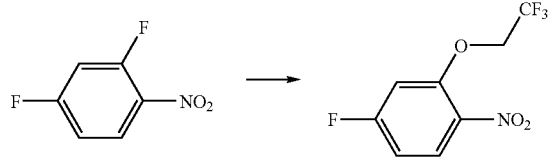

4-Fluoro-1-nitro-2-(2,2,2-trifluoro-ethoxy)-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(2,2,2-trifluoroethoxy)phenyl]amino}carbonyl)thiophene-2-sulfonamide. ES-MS (M+H)⁺=605, 607(Cl).

Example 90

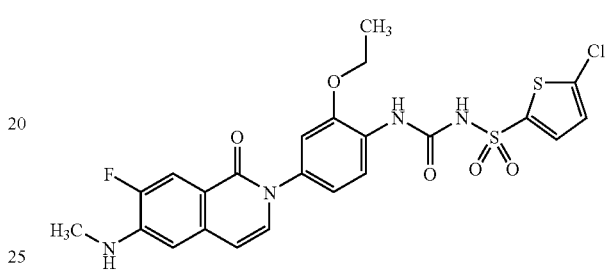

2-Ethoxy-4-fluoro-1-nitro-benzene was obtained as a side product when prepared Example 89 using 2,2,2-trifluoroethanol as described in Example 84.

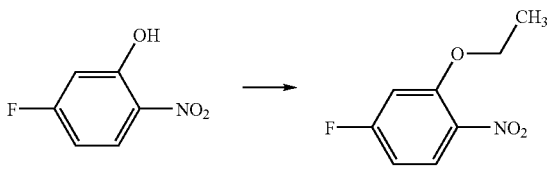

2-Ethoxy-4-fluoro-1-nitro-benzene was coupled to (7-Fluoro-1-oxo-1,2-dihydro-isoquinolin-6-yl)-methyl-carbamic acid tert-butyl ester using Method A (Example 46).

Formation of the sulfonyl urea was achieved using the method described in Example 10, followed by TFA deprotection, to give 5-chloro-N-[({2-ethoxy-4-[7-fluoro-6-(methylamino)-1-oxoisoquinolin-2(1H)-yl]phenyl}amino)carbonyl]thiophene-2-sulfonamide. ES-MS (M+H)⁺=551, 553 (Cl).

Example 91

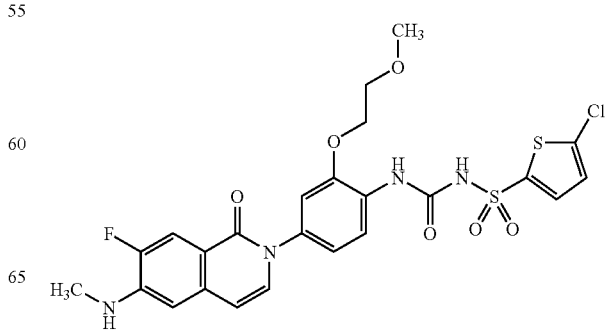

4-Fluoro-2-(2-methoxy-ethoxy)-1-nitro-benzene was obtained from 2-methoxy-ethanol using the procedure described in Example 89.

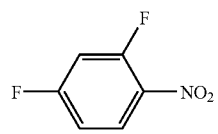 

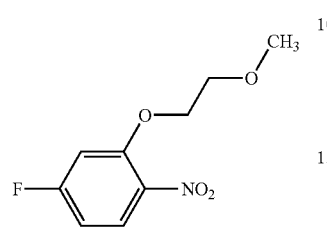

4-Fluoro-2-(2-methoxy-ethoxy)-1-nitro-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(2-methoxyethoxy)phenyl]amino}carbonyl)thiophene-2-sulfonamide. ES-MS (M+H)$^+$=581, 583(Cl).

Example 92

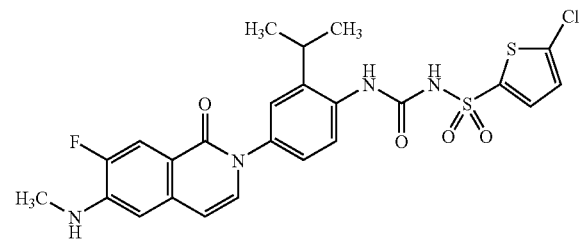

To a solution of 2-isopropyl-phenylamine (262 mg, 1.94 mmol) and sodium acetate (159 mg, 1.94 mmol) in 5 mL acetic acid, was added iodide monochloride (409 mg, 2.58 mmol) at room temperature. The mixture was stirred at room temperature for 20 minutes, then diluted with ethyl acetate and washed with saturated sodium bicarbonate. The organic layers were combined and concentrated in vacuo to give a crude residue, which was purified by column chromatography (silica 5-25% EtOAc/hexane) to give 4-iodo-2-isopropyl-phenylamine.

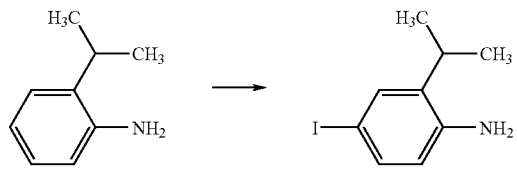

4-Iodo-2-isopropyl-phenylamine was coupled to (7-Fluoro-1-oxo-1,2-dihydro-isoquinolin-6-yl)-methyl-carbamic acid tert-butyl ester using Method C (Example 48). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2-isopropylphenyl}amino)carbonyl]thiophene-2-sulfonamide. ES-MS (M+H)$^+$=549, 551 (Cl).

Example 93

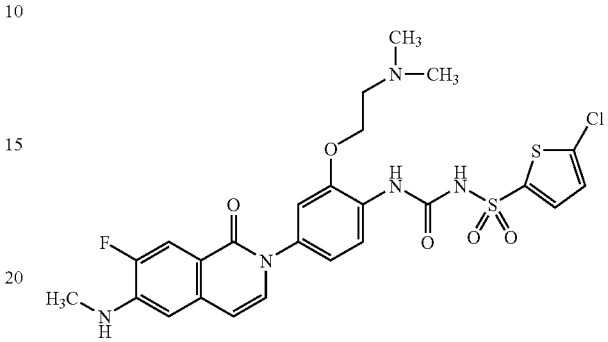

[2-(5-Fluoro-2-nitro-phenoxy)-ethyl]-dimethyl-amine was obtained from 2-dimethylamino-ethanol using the procedure described in Example 89.

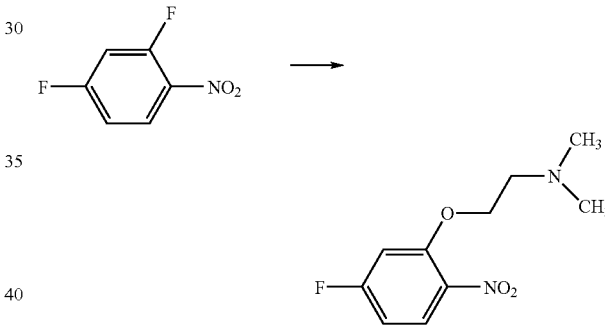

[2-(5-Fluoro-2-nitro-phenoxy)-ethyl]-dimethyl-amine was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-[({2-[2-(dimethylamino)ethoxy]-4-[7-fluoro-6-(methylamino)-1-oxoisoquinolin-2(1H)-yl]phenyl}amino)carbonyl]thiophene-2-sulfonamide. ES-MS (M+H)$^+$=594, 596(Cl).

Example 94

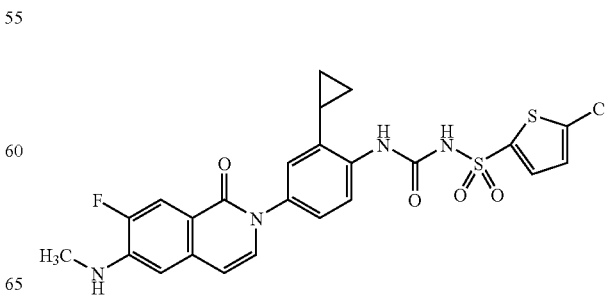

[2-(3-Cyclopropyl-4-nitro-phenyl)-7-fluoro-1-oxo-1,2-dihydro-isoquinolin-6-yl]-methyl-carbamic acid tert-butyl ester was obtained from [7-fluoro-2-(4-nitro-3-vinyl-phenyl)-1-oxo-1,2-dihydro-isoquinolin-6-yl]-methyl-carbamic acid tert-butyl (intermediate in Example 78).

To a solution of [7-fluoro-2-(4-nitro-3-vinyl-phenyl)-1-oxo-1,2-dihydro-isoquinolin-6-yl]-methyl-carbamic acid tert-butyl (12 mg, 0.027 mmol) in 1 mL ether and 1 mL THF, was added diazomethane solution (generated by adding 40% potassium hydroxide aqueous solution to 2-methyl-3-nitro-nitrosoguanidine (40 mg, 0.27 mmol) in 2 mL ether at −78° C.) at 0° C., followed by 10 mg palladium (II) acetate (10 mg, 0.4 mmol). The reaction mixture was stirred at 0° C. for 1 hour, then diluted with ethyl acetate and washed with brine. The organic layers were combined and concentrated in vacuo to give a crude residue, which was purified by column chromatography (silica 25-50% EtOAc/hexane) to give [2-(3-cyclopropyl-4-nitro-phenyl)-7-fluoro-1-oxo-1,2-dihydro-isoquinolin-6-yl]-methyl-carbamic acid tert-butyl ester.

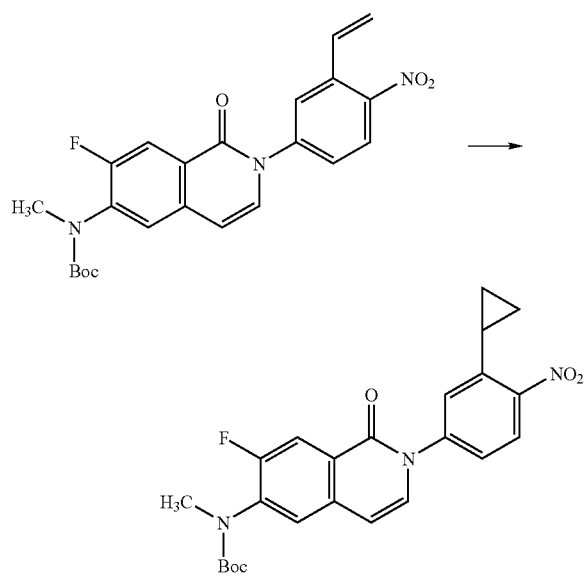

Catalytic hydrogenation of [2-(3-cyclopropyl-4-nitro-phenyl)-7-fluoro-1-oxo-1,2-dihydro-isoquinolin-6-yl]-methyl-carbamic acid tert-butyl ester, formation of the sulfonyl urea, followed by TFA deprotection, provided 5-chloro-N-[({2-cyclopropyl-4-[7-fluoro-6-(methylamino)-1-oxoisoquinolin-2(1H)-yl]phenyl}amino)carbonyl]thiophene-2-sulfonamide. ES-MS (M+H)$^+$=547, 549(Cl).

Example 95

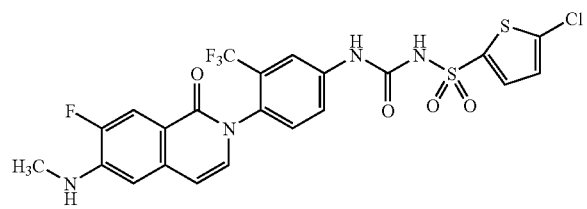

The substituted aniline was generated by Method A (Example 46) using 1-fluoro-4-nitro-2-trifluoromethyl-benzene.

Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-3-(trifluoromethyl)phenyl]amino}carbonyl)thiophene-2-sulfonamide. ES-MS (M+H)$^+$=575, 577 (Cl).

Example 96

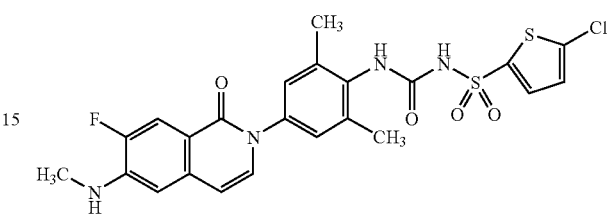

The substituted aniline was generated by Method C (Example 48) coupling 4-bromo-2,6-dimethyl-phenylamine to (7-Fluoro-1-oxo-1,2-dihydro-isoquinolin-6-yl)-methyl-carbamic acid tert-butyl ester. Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2,6-dimethylphenyl}amino)carbonyl]thiophene-2-sulfonamide. ES-MS (M+H)$^+$=535, 537(Cl).

Example 97

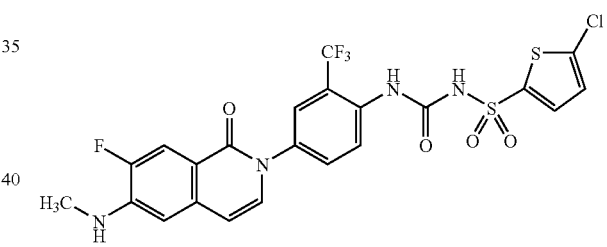

4-Fluoro-1-nitro-2-trifluoromethyl-benzene was coupled to (7-Fluoro-1-oxo-1,2-dihydro-isoquinolin-6-yl)-methyl-carbamic acid tert-butyl ester using Method A (Example 46). Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(trifluoromethyl)phenyl]amino}carbonyl)thiophene-2-sulfonamide. ES-MS (M+H)$^+$=575, 577 (Cl).

Example 98

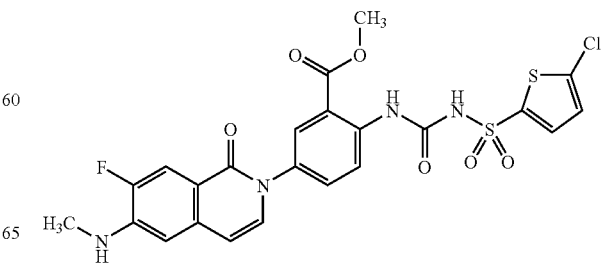

To a solution of 5-fluoro-2-nitro-benzoic acid (1 g, 5.4 mmol in 5 mL THF, was added (trimethylsilyl)diazomethane (2 M in ether, 11 ml, 22 mmol) at 0° C. The reaction mixture was warmed to room temperature under argon and stirred for 30 minutes, then diluted with ethyl acetate and washed with brine. The organic layers were combined and concentrated in vacuo to give a crude residue, which was purified by column chromatography (silica 5-30% EtOAc/hexane) to give 5-fluoro-2-nitro-benzoic acid methyl ester.

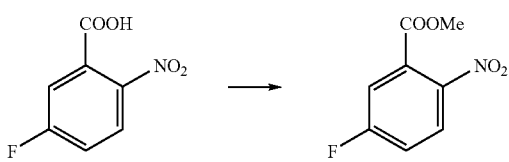

5-Fluoro-2-nitro-benzoic acid methyl ester was coupled to (7-Fluoro-1-oxo-1,2-dihydro-isoquinolin-6-yl)-methyl-carbamic acid tert-butyl ester using Method A (Example 46).

Formation of the sulfonyl urea was achieved using the method described in Example 10, followed by TFA deprotection, to give methyl 2-[({[(5-chlorothien-2-yl)sulfonyl]amino}carbonyl)amino]-5-[7-fluoro-6-(methylamino)-1-oxoisoquinolin-2(1H)-yl]benzoate. ES-MS (M+H)$^+$=565, 567(Cl).

Example 99

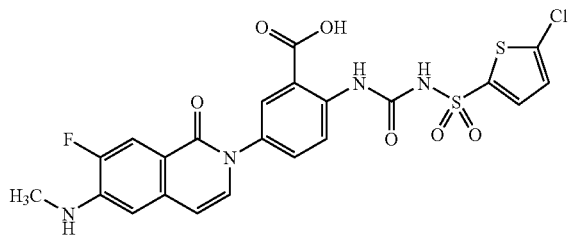

This analog compound was obtained from hydrolysis (as described in Example 63) of methyl 2-[({[(5-chlorothien-2-yl)sulfonyl]amino}carbonyl)amino]-5-[7-fluoro-6-(methylamino)-1-oxoisoquinolin-2(1H)-yl]benzoate obtained in Example 98. 2-[({[(5-chlorothien-2-yl)sulfonyl]amino}carbonyl)amino]-5-[7-fluoro-6-(methylamino)-1-oxoisoquinolin-2(1H)-yl]benzoic acid. ES-MS (M+H)$^+$=551, 553(Cl).

Example 100

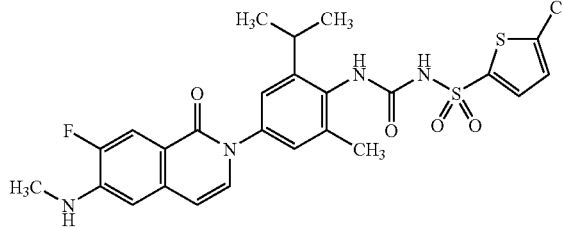

To a solution of 2-isopropyl-6-methyl-phenylamine (1 ml, 6.4 mmol) in 6.5 mL acetic acid, was added bromine (0.33 ml, 6.4 mmol) dropwise over 10 minutes at room temperature. The mixture was stirred at room temperature under argon for 20 minutes. A precipitate was formed and collected by filtration and washed with ether to give pure 4-bromo-2-isopropyl-6-methyl-phenyl amine.

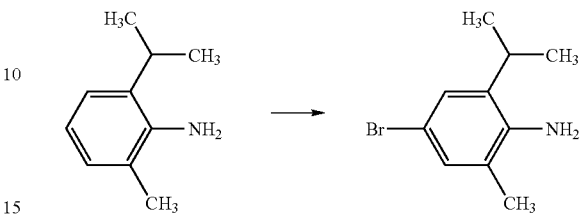

4-Bromo-2-isopropyl-6-methyl-phenylamine was coupled to (7-Fluoro-1-oxo-1,2-dihydro-isoquinolin-6-yl)-methyl-carbamic acid tert-butyl ester using Method C (Example 48). Formation of the sulfonyl urea was achieved using the method described in Example 10, followed by TFA deprotection, to give 5-chloro-N-[({4-[7-fluoro-6-(methylamino)-1-oxoisoquinolin-2(1H)-yl]-2-isopropyl-6-methylphenyl}amino)carbonyl]thiophene-2-sulfonamide. ES-MS (M+H)$^+$=563, 565(Cl).

Example 101

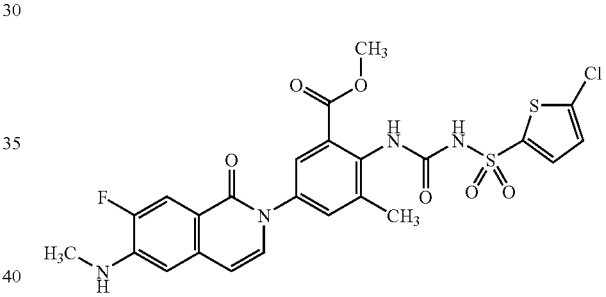

3-Methyl-2-nitro-benzoic acid methyl ester was obtained from 3-methyl-2-nitro-benzoic acid using the procedure described in Example 98, then reduced to 2-amino-3-methyl-benzoic acid methyl ester by hydrogenation as described in Method A (Example 46). 2-Amino-5-bromo-3-methyl-benzoic acid methyl ester was obtained using the procedure in Example 100.

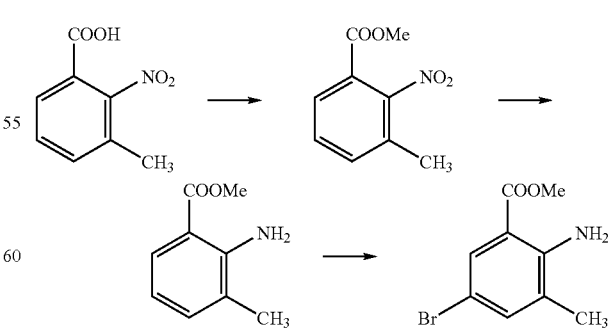

2-Amino-5-bromo-3-methyl-benzoic acid methyl ester was coupled to (7-Fluoro-1-oxo-1,2-dihydro-isoquinolin-6-yl)-methyl-carbamic acid tert-butyl ester using Method C (Example 48). Formation of the sulfonyl urea was achieved using the method described in Example 10, followed by TFA deprotection, to methyl 2-[({[(5-chlorothien-2-yl)sulfonyl]amino}carbonyl)amino]-5-[7-fluoro-6-(methylamino)-1-oxoisoquinolin-2(1H)-yl]-3-methylbenzoate. ES-MS (M+H)⁺=579, 581 (Cl).

Example 102

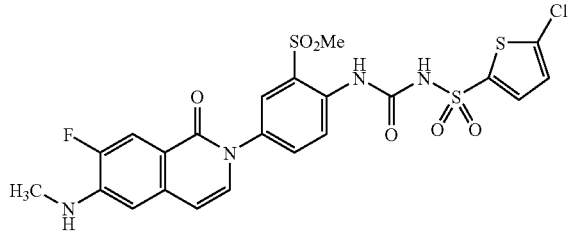

[7-Fluoro-2-(3-methanesulfonyl-4-nitro-phenyl)-1-oxo-1,2-dihydro-isoquinolin-6-yl]-methyl-carbamic acid tert-butyl ester was obtained from [2-(3-bromo-4-nitro-phenyl)-7-fluoro-1-oxo-1,2-dihydro-isoquinolin-6-yl]-methyl-carbamic acid tert-butyl ester in Example 78.

To a slolution of [2-(3-bromo-4-nitro-phenyl)-7-fluoro-1-oxo-1,2-dihydro-isoquinolin-6-yl]-methyl-carbamic acid tert-butyl ester (10 mg, 0.02 mmol) in DMSO 0.5 ml, sodium methanesulfinate (62 mg, 0.06 mmol) was added. The reaction mixture was subjected to microwave irradiation (temperature 12° C.) for 45 seconds. A precipitate was formed and collected by filtration to give [7-fluoro-2-(3-methanesulfonyl-4-nitro-phenyl)-1-oxo-1,2-dihydro-isoquinolin-6-yl]-methyl-carbamic acid tert-butyl ester.

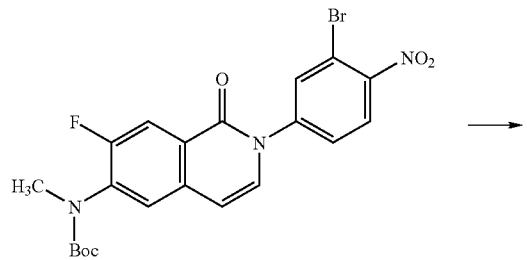

[7-fluoro-2-(3-methanesulfonyl-4-nitro-phenyl)-1-oxo-1,2-dihydro-isoquinolin-6-yl]-methyl-carbamic acid tert-butyl ester was hydrogenated to provide an aniline. Formation of the sulfonyl urea was achieved using the method described in Example 10, followed by TFA deprotection, to give 5-chloro-N-({[4-[7-fluoro-6-(methylamino)-1-oxoisoquinolin-2(1H)-yl]-2-(methylsulfonyl)phenyl]amino}carbonyl)thiophene-2-sulfonamide. ES-MS (M+H)⁺=585, 587(Cl).

Example 103

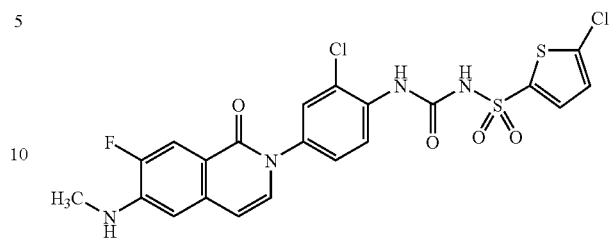

The substituted aniline was generated by Method C (Example 48) using 2-chloro-4-iodo-phenylamine. Formation of the sulfonyl urea was achieved using the method described in Example 10, followed by TFA deprotection, to give 5-chloro-N-[({2-chloro-4-[7-fluoro-6-(methylamino)-1-oxoisoquinolin-2(1H)-yl]phenyl}amino)carbonyl]thiophene-2-sulfonamide. ES-MS (M+H)⁺=541, 543(Cl).

Example 104

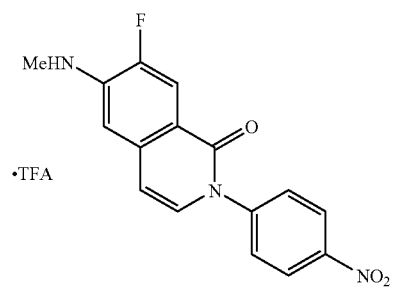

[7-Fluoro-2-(4-nitro-phenyl)-1-oxo-1,2-dihydro-isoquinolin-6-yl]-methyl-carbamic acid tert-butyl ester (1.0 g, 24 mmol, from Example 8) was dissolved in 12.5 mL of TFA and stirred for 0.5 h. The solvent was removed in vacuo and re-dissolved in dichloromethane/heptane and concentrated to give 1.0 g (97%) of the TFA salt as a yellowish solid. ES-MS (M+H)⁺=314.2.

Example 105

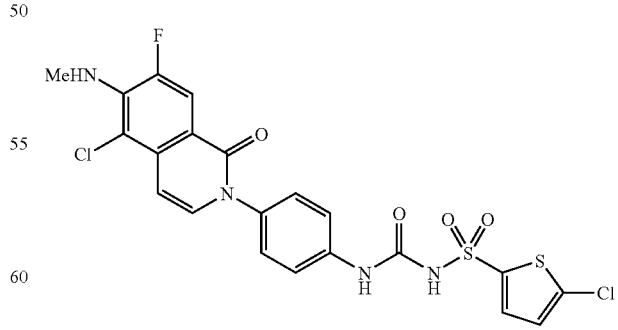

To a mixture of 7-Fluoro-6-methylamino-2-(4-nitro-phenyl)-2H-isoquinolin-1-one (100 mg, 0.27 mmol) (Example 104) in DMF (3 mL) was added N-chlorosuccinimide (76 mg, 0.57 mmol). After 18 hours all starting material was consumed. Tin dichloride dehydrate 244 mg (0.11 mmol) was added to the reaction mixture, and the reaction was heated to 80° C. for 2 hr. Upon cooling the reaction mixture was treated with 1 mL of 10% sodium carbonate and extracted 3 times with EtOAc. The combined organic layers were dried over Na$_2$SO$_4$ anhydrous and concentrated in vacuo to give a mixture of the 5-Cl and 4,5-dichloro anilines. This mixture was coupled directly with 76 mg (0.28 mmol) of (5-Chloro-thiophene-2-sulfonyl)-carbamic acid ethyl ester (Example 12) in toluene (0.54 mL) and refluxed for 4 h. The resulting mixture of monochloro and dichloro sulfonylureas were separated by preparative RP-HPLC to give 9.4 mg (6% yield overall) of 5-chloro-N-[({4-[5-chloro-7-fluoro-6-(methylamino)-1-oxoisoquinolin-2(1H)-yl]phenyl}amino)carbonyl]thiophene-2-sulfonamide. ES-MS (M+H)$^+$=541.3 (2Cl).

Example 106

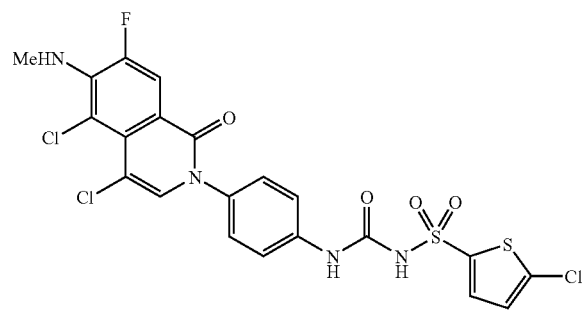

The dichloro sulfonylurea was purified from the above reaction in Example 105 to afford 15 mg (10% overall yield) of 5-chloro-N-[({4-[4,5-dichloro-7-fluoro-6-(methylamino)-1-oxoisoquinolin-2(1H)-yl]phenyl}amino)carbonyl]thiophene-2-sulfonamide. ES-MS (M+H)$^+$=576.2 (3Cl).

Example 107

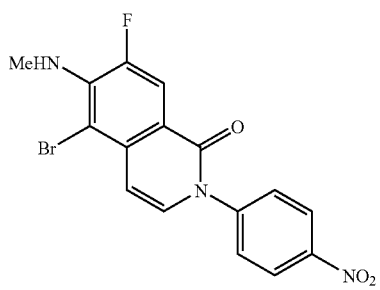

7-Fluoro-6-methylamino-2-(4-nitro-phenyl)-2H-isoquinolin-1-one (800 mg, 1.9 mmol, TFA salt from example 104) was partially dissolved in 18 mL of DMF containing 517 mg (2 equiv) of K$_2$CO$_3$. Recrystallized N-bromosuccinimide (433 mg, 2.4 mmol) was added and the reaction was warmed to 70° C. and stirred for 18 h. The reaction mixture was quenched with 25 mL of water and cooled to 0° C. The resulting precipitate was collected by filtration, washed with water, and dried in vacuo at 23° C. to give 600 mg (82%) of an off-white solid. ES-MS (M+H)$^+$=392.3 (Br).

Example 108

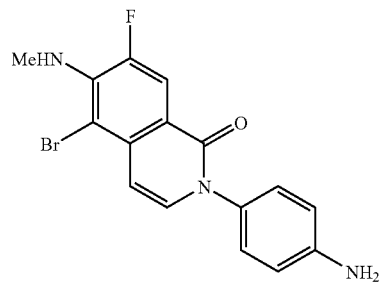

5-Bromo-7-fluoro-6-methylamino-2-(4-nitro-phenyl)-2H-isoquinolin-1-one (400 mg, 1.0 mmol, Example 107) was combined with 920 mg (4.0 mmol) of tin dichloride dehydrate in 5 mL of DMF and heated to 70° C. for 2 h. The reaction was then cooled to 40° C. and 1 mL of 10% sodium carbonate was added slowly along with 2 g of celite. The reaction mixture was then extracted 3 times with EtOAc and the combined organic layers were dried over sodium sulfate, concentrated in vacuo to afford 338 mg (94%) of a yellowish solid. ES-MS (M+H)$^+$=361.2 (Br).

Example 109

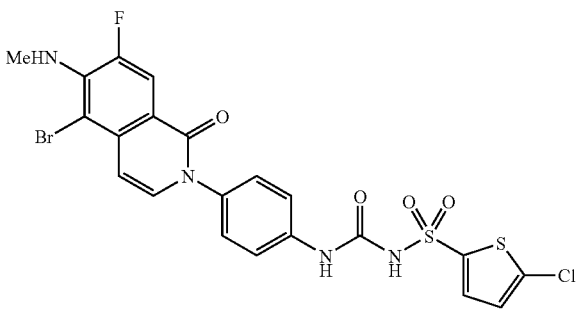

The sulfonylurea is prepared via the method described in Example 13. N-[({4-[5-bromo-7-fluoro-6-(methylamino)-1-oxoisoquinolin-2(1H)-yl]phenyl}amino) carbonyl]-5-chlorothiophene-2-sulfonamide. ES-MS (M+H)$^+$=585.5(Cl,Br).

Example 110

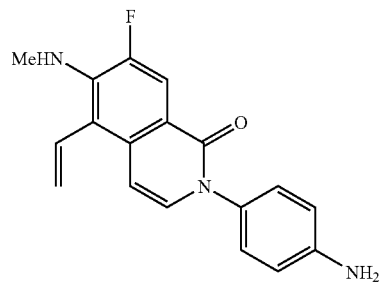

To a suspension of 2-(4-Amino-phenyl)-5-bromo-7-fluoro-6-methylamino-2H-isoquinolin-1-one from Example 108 (26 mg, 0.07 mmol) in DME (0.5 mL) was added tetrakis(triphenylphosphine)palladium (4 mg, 5 mol %). The suspension was degassed and purged with Ar. K$_2$CO$_3$ (10 mg, 0.07 mmol), water (0.2 mL) and the pyridine complex of 2,4,6-trivinylcyclotriboroxance (9 mg, 0.04 mmol) were then added and the mixture heated to 100° C. After 30 min., the reaction mixture was cooled to room temperature. The product was then extracted with EtOAc (20 mL), washed with brine (10 mL). The combined organic layers was dried over sodium sulfate and concentrated in vacuo to give 26 mg of the crude product, which was used without additional purification. ES-MS (M+H)$^+$=310.3.

Example 111

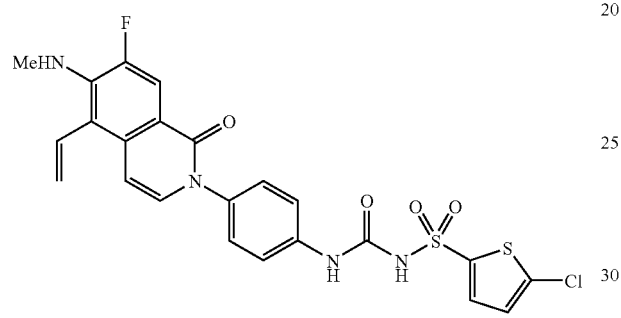

Coupling to form the sulfonyl urea was achieved using the method described in Example 13 using Example 110 as a coupling partner to give 5-chloro-N-[({4-[7-fluoro-6-(methylamino)-1-oxo-5-vinylisoquinolin-2(1H)-yl]phenyl}amino)carbonyl]thiophene-2-sulfonamide. ES-MS (M+H)$^+$=533.0, 535.0 (Cl).

Example 112

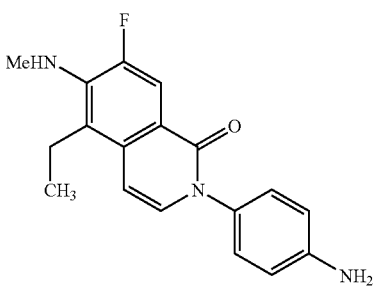

To a solution of 2-(4-Amino-phenyl)-7-fluoro-6-methylamino-5-vinyl-2H-isoquinolin-1-one from Example 110 (27 mg, 0.09 mmol) in ethyl acetate (1 mL) and ethanol (1 mL) under Ar was added 10% Pd/C (19 mg, 0.18 mmol Pd). The mixture was hydrogenated under 1 atm H$_2$ for 2 hr, filtered through Celite and concentrated to give 26 mg of the crude product, which was used without additional purification. ES-MS (M+H)$^+$=312.3.

Example 113

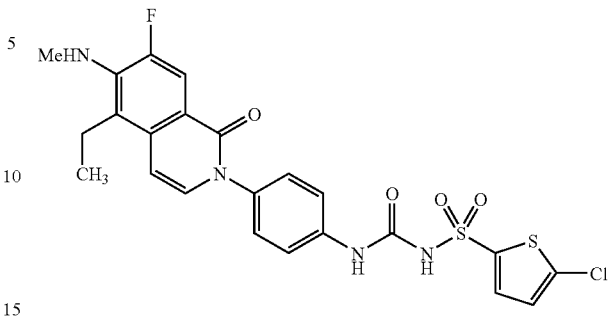

Coupling to form the sulfonyl urea was achieved using the method described in Example 13 using 2-(4-Amino-phenyl)-5-ethyl-7-fluoro-6-methylamino-2H-isoquinolin-1-one from previous example as a coupling partner to give 5-chloro-N-[({4-[5-ethyl-7-fluoro-6-(methylamino)-1-oxoisoquinolin-2(1H)-yl]phenyl}amino)carbonyl]thiophene-2-sulfonamide. ES-MS (M+H)$^+$=535.0, 537.0 (Cl).

Example 114

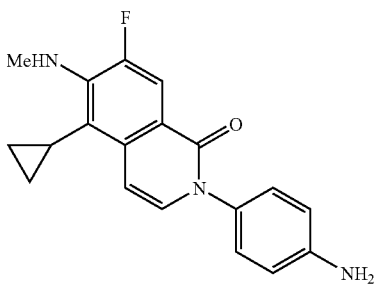

To a suspension of 2-(4-Amino-phenyl)-5-bromo-7-fluoro-6-methylamino-2H-isoquinolin-1-one from Example 108 (50 mg, 0.14 mmol) in toluene (0.6 mL) was added tetrakis(triphenylphosphine)palladium (16 mg). The suspension was degassed and purged with Ar. K$_3$PO$_4$ (103 mg, 0.49 mmol), water (0.2 mL) and cyclopropyl boronic acid (15 mg, 0.18 mmol) were then added and the mixture heated to 100° C. After reacting overnight, the mixture was cooled to r.t. The reaction mixture was then extracted with EtOAc (20 mL), washed with brine (10 mL), dried over sodium sulfate and concentrated in vacuo to give 48 mg of the crude product. The crude was purified over silica gel to give 12 mg (25%) of the pure product. ES-MS (M+H)$^+$=324.1.

Example 115

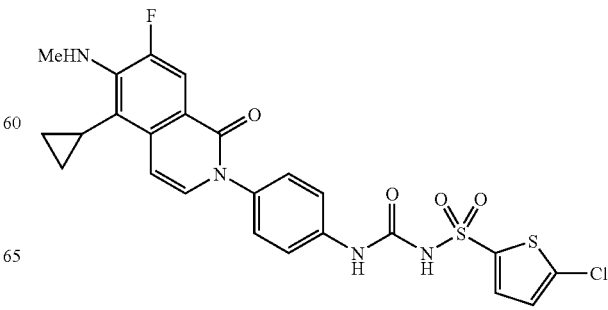

Coupling to form the sulfonyl urea was achieved using the method described in Example 13 using to give 5-chloro-N-[({4-[5-cyclopropyl-7-fluoro-6-(methylamino)-1-oxoisoquinolin-2(1H)-yl]phenyl}amino)carbonyl]thiophene-2-sulfonamide ES-MS (M+H)$^+$=547.1, 549.1 (Cl).

Example 116

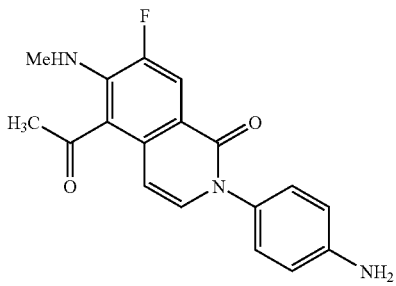

2-(4-Amino-phenyl)-5-bromo-7-fluoro-6-methylamino-2H-isoquinolin-1-one from Example 108 (50 mg, 0.14 mmol) and tributylethoxyvinyl tin (102 µL, 0.28 mmol) were combined in toluene (0.7 mL) and then the mixture degassed and purged with Ar. Tetrakis(triphenylphosphine) palladium (16 mg, 10 mol %) was added and the mixture heated to 100° C. The mixture was stirred under Ar for 3 h, after which the reaction mixture was cooled to room temperature. Water (30 mL) was added to the reaction mixture and the product extracted with EtOAc (30 mL), washed with a 5% ammonia/water solution (30 mL) and brine (30 mL), dried over sodium sulfate and concentrated in vacuo to give 146 mg of the crude ethoxyvinyl compound. The crude mixture was then dissolved in THF (10 mL), treated with 2N HCl (3 mL) and stirred at room temperature for 1.5 h. The mixture was then neutralized with NaHCO$_3$ and extracted with EtOAc (30 mL). The EtOAc layer was washed with brine (25 mL), dried over sodium sulfate and concentrated in vacuo to give the crude ketone, which was purified over silica gel to give the final product. ES-MS (M+H)$^+$=326.1.

Example 117

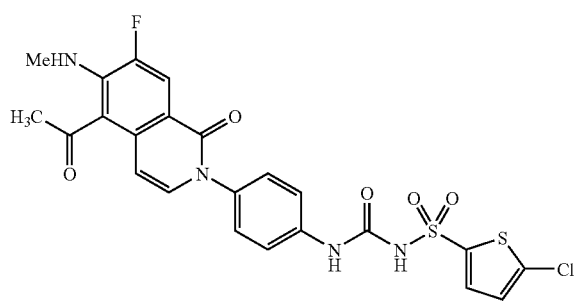

Coupling to form the sulfonyl urea was achieved using the method described in Example 13 to give N-[({4-[5-acetyl-7-fluoro-6-(methylamino)-1-oxoisoquinolin-2(1H)-yl]phenyl}amino)carbonyl]-5-chlorothiophene-2-sulfonamide. ES-MS (M+H)$^+$=549.0, 551.0 (Cl).

Example 118

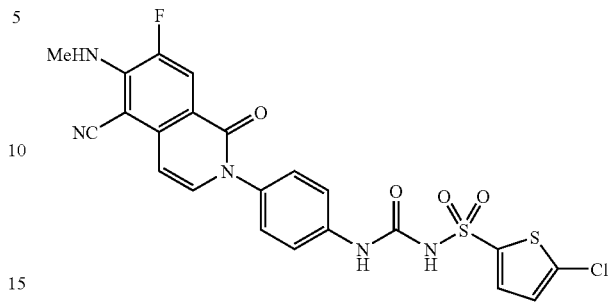

A 110 mg (0.28 mmol) portion of 5-Bromo-7-fluoro-6-methylamino-2-(4-nitro-phenyl)-2H-isoquinolin-1-one (Example 107) and 55 mg (2.2 equiv) of CuCN in 1.4 mL of NMP was heated to 200° C. for 2 h. After cooling to 50° C., 10 mL of 10% aq KCN was added, and mixture was stirred, filtered, washed with water and dried to give 123 mg (130%) of 7-Fluoro-6-methylamino-2-(4-nitro-phenyl)-1-oxo-1,2-dihydro-isoquinoline-5-carbonitrile. A 50 mg (0.15 mmol) portion of this 5-cyano material was reduced with 36 mg of Raney Nickel (Aldrich) in 1:1:2 water/AcOH/pyridine containing 58 mg of sodium hypophosphite. The reaction was then extracted 3 times with ethyl acetate, drying over Na$_2$SO$_4$ (anh.), and concentration in vacuo afforded 10 mg (20%) of the resulting aniline. This material was then coupled using the method described in Example 13 to give 7.8 mg (46%) of 5-chloro-N-[({4-[5-cyano-7-fluoro-6-(methylamino)-1-oxoisoquinolin-2(1H)-yl]phenyl}amino)carbonyl]thiophene-2-sulfonamide. ES-MS (M+H)$^+$=532.1 (Cl).

Example 119

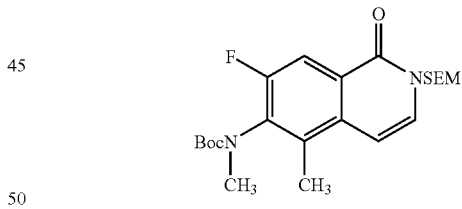

[7-Fluoro-1-oxo-2-(2-trimethyl-silanyl-ethoxymethyl)-1,2-dihydro-isoquinolin-6-yl]-carbamic acid tert-butyl ester (200 mg, 0.5 mmol, Example 44) was dissolved in 1.5 mL of dry THF and further dried by stirring for 1 h in the presence of 3A molecular sieves. The reaction mixture was then cooled to −78° C. and 1.0 mL of t-BuLi (1.9M) was added dropwise. After 1 h, 123 µL (4 equiv) of MeI was added and the reaction mixture was warmed slowly to 23° C. After addition of 2 mL of sat. NH$_4$Cl and extraction 3 times with ethyl acetate, the combined organic layers were dried over Na$_2$SO$_4$, concentrated and purified on silica gel eluting with a 5% to 20% ethyl acetate/hexane gradient to afford 44 mg (20%) of [7-Fluoro-5-methyl-1-oxo-2-(2-trimethylsilanyl-ethoxymethyl)-1,2-dihydro-isoquinolin-6-yl]-methyl-carbamic acid tert-butyl ester. ES-MS (M+H)$^+$=437.4.

Example 120

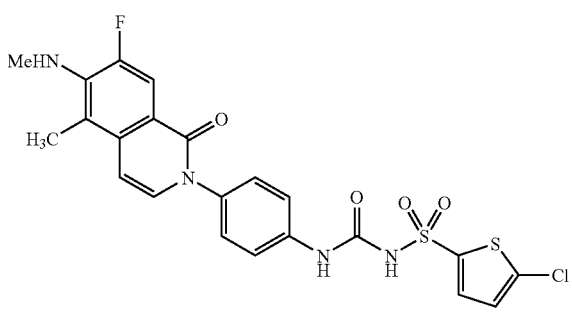

[7-Fluoro-5-methyl-1-oxo-2-(2-trimethylsilanyl-ethoxymethyl)-1,2-dihydro-isoquinolin-6-yl]-methyl-carbamic acid tert-butyl ester (44 mg, 0.10 mmol, Example 119) was treated with TFA for 1 h and concentrated in vacuo. Treatment of this crude material with 25 mg (0.115 mmol) of p-iodoaniline, 4 mg of CuI, 3 mg 8-hydroxyquinoline and 17 mg of $K_2CO_3$ in 200 μL of DMSO at 120° C. for 18 hrs, after which the reaction was cooled to room temperature, diluted with ethyl acetate and washed with brine. The combined organic layers were dried over $Na_2SO_4$ and concentrated in vacuo to give a crude residue, which was subjected to coupling with 57 mg of (5-Chloro-thiophene-2-sulfonyl)-carbamic acid ethyl ester as described in Example 13, gave 10 mg of 5-chloro-N-[({4-[7-fluoro-5-methyl-6-(methylamino)-1-oxoisoquinolin-2(1H)-yl]phenyl}amino)carbonyl]thiophene-2-sulfonamide after RP-HPLC purification. ES-MS $(M+H)^+=521.1$ (Cl).

Example 121

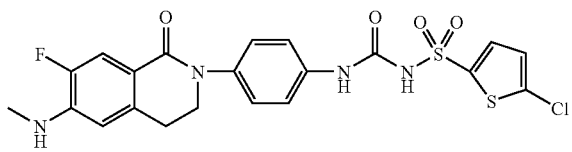

Step 1: Preparation of 7-fluoro-6-(methylamino)-3,4-dihydroisoquinolin-1(2H)-one

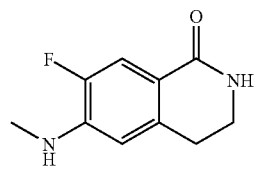

A mixture of tert-butyl 7-fluoro-1-oxo-1,2-dihydroisoquinolin-6-yl(methyl)carbamate (Example 45, 700 mg, 2.40 mmol) and $PtO_2$ (470 mg) in MeOH (30 mL) containing concentrated HCl (8 drops) was hydrogenated under 300 psi in a high pressure vessel overnight. The reaction mixture was then filtered and the filtrate was concentrated in vacuo. The residue was treated with TFA (10 mL) and stirred for 1 hr, after which, the TFA solution was concentrated in vacuo. The residue was purified by RP-HPLC to give the noted intermediate compound (142 mg). ES-MS $(M+H)^+=195$.

Step 2: Preparation of 2-(4-aminophenyl)-7-fluoro-6-(methylamino)-3,4-dihydroisoquinolin-1(2H)-one

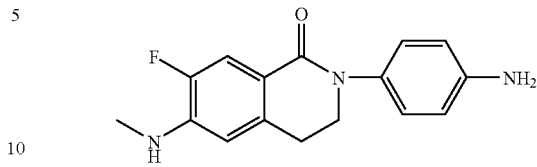

A mixture of 7-fluoro-6-(methylamino)-3,4-dihydroisoquinolin-1(2H)-one (70 mg, 0.36 mmol), 4-iodoaniline (119 mg, 0.543 mmol), CuI (27 mg, 0.14 mmol), 1,2-diaminocyclohexane (44 uL, 0.36 mmol) and $K_3PO_4$ (153 mg, 0.722 mmol) in dioxane (1.5 mL) was heated at 110° C. overnight, then diluted with $CH_3CN$ (5 mL) and $H_2O$ (5 mL) and filtered. The filtrate was purified by RP-HPLC to give the noted intermediate compound as a solid (62 mg). ES-MS $(M+H)^+=286$.

Step 3: Preparation of 1-(5-chlorothiophen-2-ylsulfonyl)-3-(4-(7-fluoro-6-(methylamino)-1-oxo-3,4-dihydroisoquinolin-2(1H)-yl)phenyl)urea

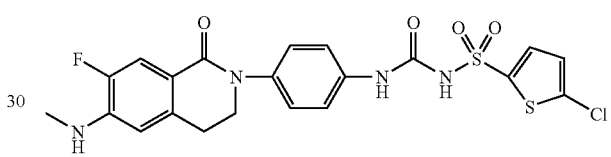

To a solution of 2-(4-aminophenyl)-7-fluoro-6-(methylamino)-3,4-dihydroisoquinolin-1(2H)-one (62 mg, 0.22 mmol) in HOAc (4 mL) at 100 C, ethyl 5-chlorothiophen-2-ylsulfonylcarbamate (119 mg, 0.44 mmol) was added. After being stirred at room temperature for 1 h, the reaction mixture was concentrated in vacuo. The residue was purified by RP-HPLC to give the titled compound as a powder (25 mg). ES-MS $(M+H)^+=509, 511$ (Cl pattern).

Example 122

1-(5-chlorothiophen-2-ylsulfonyl)-3-(4-(5,7-difluoro-6-(methylamino)-1-oxo-3,4-dihydroisoquinolin-2(1H)-yl)phenyl)urea

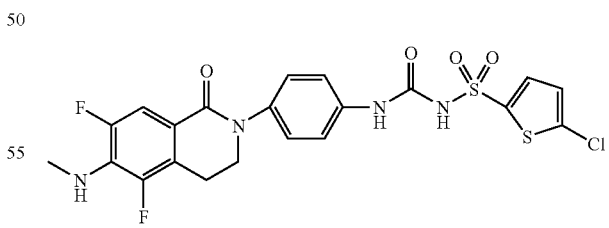

To a solution of 1-(5-chlorothiophen-2-ylsulfonyl)-3-(4-(7-fluoro-6-(methylamino)-1-oxo-3,4-dihydroisoquinolin-2(1H)-yl)phenyl)urea (17 mg, 0.033 mmol) in DMF (2 mL) at room temperature, selectFluor (1-(chloromethyl)-4-fluoro-1,4-diazoniabicyclo[2.2.2]octanebis(tetrafluoroborate), 32 mg, 0.090 mmol) was added. After being stirred at room temperature for 1 h, the reaction mixture was concentrated in vacuo. The residue was purified by RP-HPLC to give the titled compound as a powder (1 mg). ES-MS (M+H)+=527, 529 (Cl pattern).

Example 123

This Example Provides an Assay for the Inhibition of ADP-Mediated Platelet Aggregation In Vitro Using Platelet-Rich Plasma (PRP)

The effect of compounds of the invention on ADP-induced human platelet aggregation using platelet-rich plasma (PRP) is preferably assessed in a 96-well microtiter assay. Human venous blood is collected from healthy, drug-free volunteers into 0.38% sodium citrate (final concentration; e.g., 6 mL of 3.8% per 60 mL of blood). Platelet-rich plasma (PRP) is prepared by centrifugation at 160×g for 20 minutes at room temperature. PRP is collected, and the platelet concentration is determined using a Coulter counter or hemocytometer (platelet concentration should be $2-4\times10^8$ platelets per mL).

Inhibition of ADP-dependent aggregation is preferably determined in 96-well flat-bottom microtiter plates using a microtiter plate shaker and plate reader similar to the procedure described by Frantantoni et al., *Am. J. Clin. Pathol.* 94:613 (1990). All steps are performed at room temperature. The total reaction volume of 0.2 mL/well includes: PRP (~$6\times10^7$ total platelets in the presence of plasma), serial dilutions of test compounds (buffer for control wells) in 0.6% DMSO. After about 5 minutes preincubation at room temperature, ADP is added to a final concentration of 2 μM which induces submaximal aggregation. Buffer is added instead of ADP to one set of control wells (ADP-control). The OD of the samples is then determined at 650 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 650 nm at t=5 minutes compared to t=0 minutes and is expressed as % of the decrease in the ADP control samples after correcting for changes in the unaggregated control samples.

Inhibition of [$^3$H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [$^3$H]2-MeS-ADP binding to whole platelets is determined. [$^3$H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at $3-6\times10^9$ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of $6.66\times10^8$ platelets/ml. Binding experiments are performed after >45 minutes resting of the platelets.

Alternatively, binding experiments are performed with fresh human platelets prepared as described in I. (Inhibition of ADP-Mediated Platelet Aggregation in vitro), except that platelets are resuspended in Hepes-Tyrode's buffer containing 0.1% BSA (Sigma, St. Louis, Mo.) at a concentration of $6.66\times10^8$ platelets/ml. Very similar results are obtained with fresh and outdated platelets.

A platelet ADP receptor binding assay using the tritiated potent agonist ligand [$^3$H]2-MeS-ADP (Jantzen, H. M. et al. (1999) Thromb. Hemost. 81:111-117) has been adapted to the 96-well microtiter format. In an assay volume of 0.2 ml Hepes-Tyrode's buffer with 0.1% BSA and 0.6% DMSO, $1\times10^8$ apyrase-washed platelets are preincubated in 96-well flat bottom microtiter plates for 5 minutes with serial dilutions of test compounds before addition of 1 nM [$^3$H]2-MeS-ADP ([$^3$H]2-methylthioadenosine-5'-diphosphate, ammonium salt; specific activity 48-49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain $10^{-5}$ M unlabelled 2-MeS-ADP (RBI, Natick, Mass.). After incubation for 15 minutes at room temperature, unbound radioligand is separated by rapid filtration and two washes with cold (4-8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glassfiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compounds dilutions.

Example 124

This Example Provides Activity for Selected Compounds of the Invention, Evaluated as Described Above. In the Table Below, Activity in the PRP Assay is Provided as Follows: +++, $IC_{50}<10$ μM; ++, 10 μM<$IC_{50}$<30 μM; and +, $IC_{50}>30$ μM

| Example No. | Activity |
|---|---|
| Example 10 | +++ |
| Example 13 | ++ |
| Example 14 | + |
| Example 19 | +++ |
| Example 20 | +++ |
| Example 21 | ++ |
| Example 22 | +++ |
| Example 23 | +++ |
| Example 26 | + |
| Example 27 | +++ |
| Example 28 | +++ |
| Example 29 | +++ |
| Example 30 | +++ |
| Example 31 | ++ |
| Example 32 | +++ |
| Example 33 | ++ |
| Example 34 | +++ |
| Example 35 | +++ |
| Example 37 | +++ |
| Example 38 | +++ |
| Example 39 | ++ |
| Example 40 | + |

-continued

| Example No. | Activity |
|---|---|
| Example 41 | ++ |
| Example 42 | +++ |
| Example 49 | +++ |
| Example 50 | +++ |
| Example 51 | +++ |
| Example 52 | +++ |
| Example 53 | +++ |
| Example 54 | +++ |
| Example 55 | +++ |
| Example 56 | +++ |
| Example 57 | + |
| Example 58 | +++ |
| Example 59 | +++ |
| Example 60 | +++ |
| Example 61 | +++ |
| Example 62 | ++ |
| Example 63 | +++ |
| Example 65 | ++ |
| Example 67 | ++ |
| Example 68 | ++ |
| Example 70 | ++ |
| Example 73 | ++ |
| Example 74 | + |
| Example 75 | +++ |
| Example 76 | +++ |
| Example 77 | +++ |
| Example 79 | + |
| Example 80 | + |
| Example 81 | +++ |
| Example 82 | ++ |
| Example 83 | +++ |
| Example 84 | ++ |
| Example 85 | +++ |
| Example 86 | +++ |
| Example 87 | +++ |
| Example 88 | +++ |
| Example 89 | +++ |
| Example 90 | +++ |
| Example 91 | +++ |
| Example 92 | ++ |
| Example 93 | +++ |
| Example 94 | +++ |
| Example 95 | + |
| Example 96 | +++ |
| Example 97 | +++ |
| Example 98 | +++ |
| Example 99 | +++ |
| Example 100 | ++ |
| Example 101 | +++ |
| Example 102 | + |
| Example 103 | +++ |
| Example 109 | + |
| Example 118 | ++ |
| Example 120 | +++ |

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound having the formula:

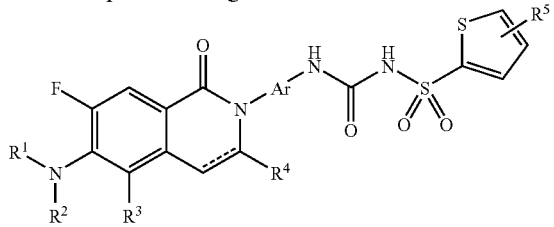

or a pharmaceutically acceptable salt thereof, wherein the dotted line represents an optional double bond;

$R^1$ is a member selected from the group consisting of $C_{1-6}$ alkyl, $C_{1-6}$ haloalkyl, $C_{3-5}$ cycloalkyl, $C_{3-5}$ cycloalkyl-alkyl and benzyl;

$R^2$ is a member selected from the group consisting of H, $C_{1-6}$ alkyl and $C_{1-6}$ haloalkyl;

$R^3$ is a member selected from the group consisting of H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, cyano and $-C(O)R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di-$C_{1-6}$ alkylamino;

$R^4$ is a member selected from the group consisting of H and $C_{1-6}$ alkyl;

$R^5$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and $-C(O)R^{5a}$, wherein $R^{5a}$ is a member selected from the group consisting of $C_{1-6}$ alkoxy, amino, $C_{1-6}$ alkylamino and di-$C_{1-6}$ alkylamino; and Ar is an aromatic ring selected from the group consisting of benzene, pyridine and pyrimidine, each of which is optionally substituted with from 1-2 $R^6$ substituents, wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, amino, $C_{1-6}$ alkylamino, di-$C_{1-6}$ alkylamino, $-C(O)R^{6a}$, $-O(CH_2)_mOR^{6b}$, $-(CH_2)_mOR^{6b}$, $-O(CH_2)_mN(R^{6b})_2$ and $-(CH_2)_mN(R^{6b})_2$, wherein the subscript m is an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di-$C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine or piperidine ring.

2. A compound of claim 1, having the formula:

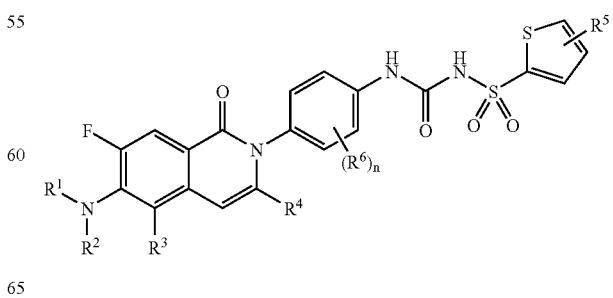

wherein the subscript n is an integer of from 0 to 2.

3. A compound of claim 1, having the formula:

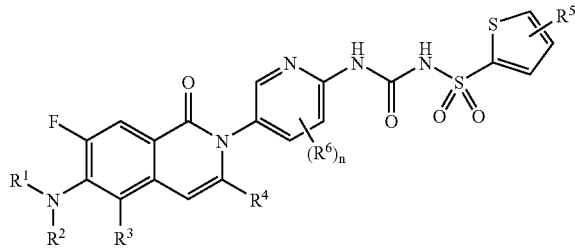

wherein the subscript n is an integer of from 0 to 2.

4. A compound of claim 1, having the formula:

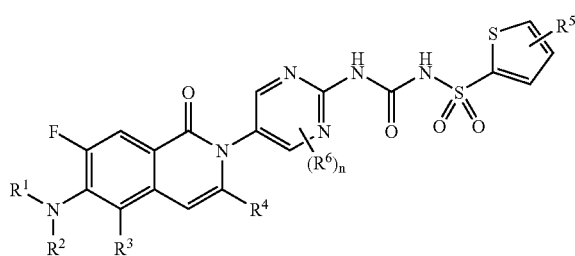

wherein the subscript n is an integer of from 0 to 2.

5. A compound of claim 2, wherein n is an integer of from 0 to 2; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

6. A compound of claim 5, wherein $R^1$ is $C_{1-4}$ alkyl; $R^4$ is H or CH$_3$; $R^5$ is halogen or $C_{1-4}$ alkyl; and $R^6$ when present is selected from $C_{1-4}$ alkyl, —O(CH$_2$)$_m$OR$^{6b}$ and —O(CH$_2$)$_m$ N(R$^{6b}$)$_2$.

7. A compound of claim 6, wherein $R^1$ is methyl; $R^5$ is chloro, and is attached at the 5-position of the thienyl ring; and $R^6$ when present is selected from the group consisting of CH$_3$, —OCH$_2$CH$_2$OH, —OCH$_2$CH$_2$OCH$_3$, —OCH$_2$OCH$_3$, —OCH$_2$CH$_2$OC(O)CH$_3$ and —O(CH$_2$)$_2$N(CH$_3$)$_2$.

8. A compound of claim 7, wherein n is 0.

9. A compound of claim 7, wherein n is 1.

10. A compound of claim 7, wherein n is 2.

11. A compound of claim 3, wherein n is 0 or 1; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

12. A compound of claim 11, wherein $R^1$ is $C_{1-4}$ alkyl; $R^4$ is H or CH$_3$; $R^5$ is halogen or $C_{1-4}$ alkyl; and $R^6$ when present is selected from $C_{1-4}$ alkyl, —O(CH$_2$)$_m$OR$^{6b}$ and —O(CH$_2$)$_m$ N(R$^{6b}$)$_2$.

13. A compound of claim 12, wherein $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or CH$_3$; $R^5$ is chloro and is attached at the 5-position of the thienyl ring; and $R^6$, when present is selected from the group consisting of $C_{1-4}$ alkyl, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

14. A compound of claim 4, wherein n is 0 or 1; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

15. A compound of claim 14, wherein $R^1$ is $C_{1-4}$ alkyl; $R^4$ is H or CH$_3$; $R^5$ is halogen or $C_{1-4}$ alkyl; and $R^6$ when present is selected from $C_{1-4}$ alkyl, —O(CH$_2$)$_m$OR$^{6b}$ and —O(CH$_2$)$_m$ N(R$^{6b}$)$_2$.

16. A compound of claim 15, wherein $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or CH$_3$; $R^5$ is chloro and is attached at the 5-position of the thienyl ring; and $R^6$, when present is selected from the group consisting of $C_{1-4}$ alkyl, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

17. A compound of claim 1, selected from the group consisting of:

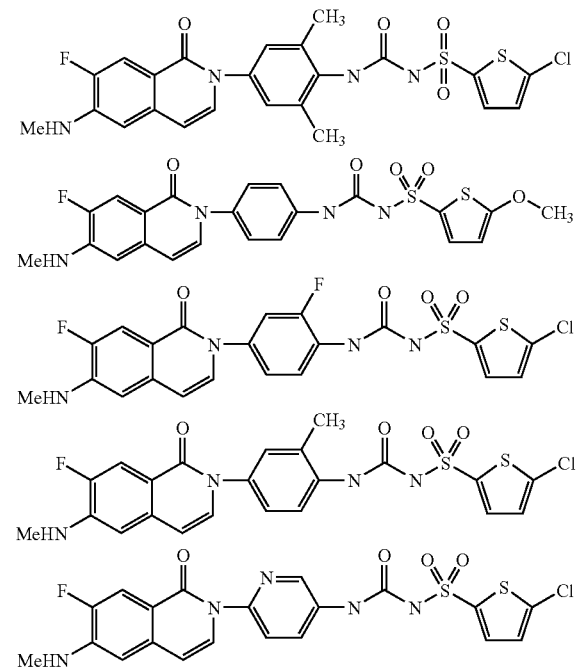

-continued
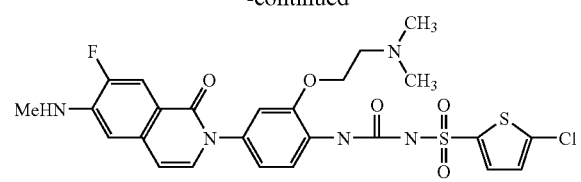
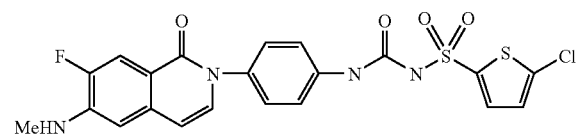
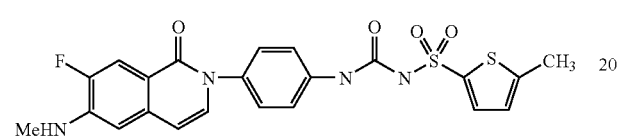
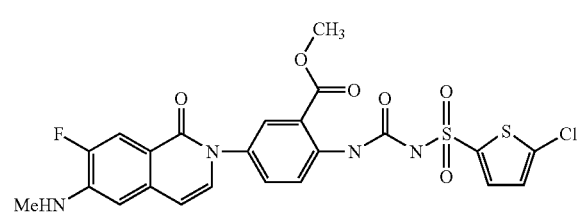
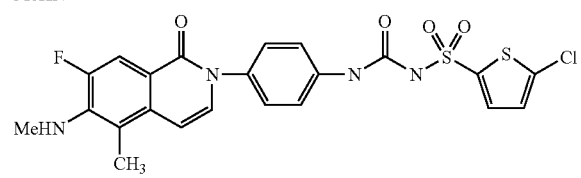
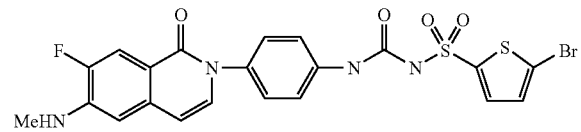
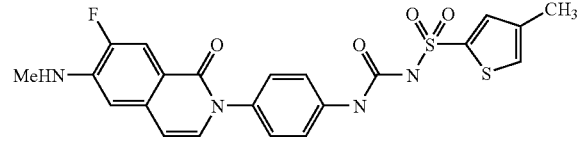
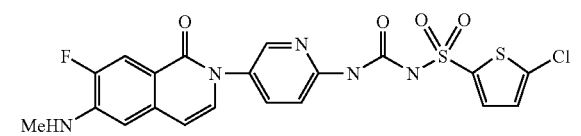
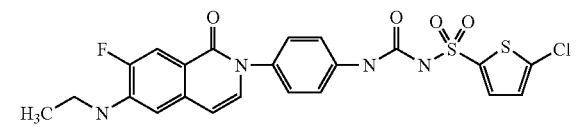
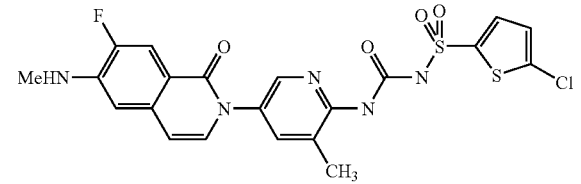
-continued
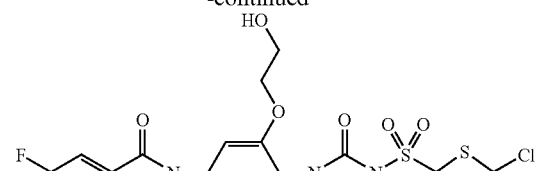
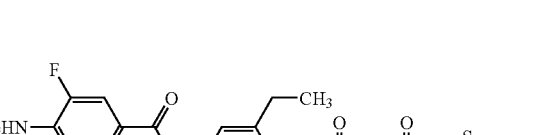
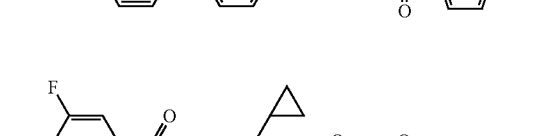
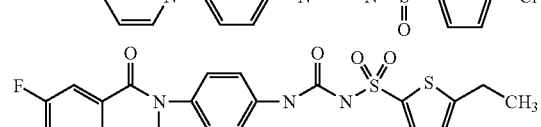
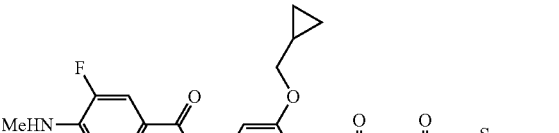
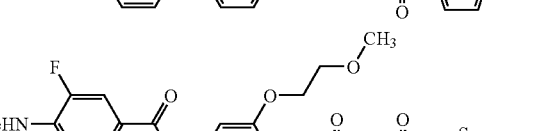
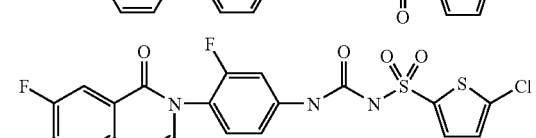
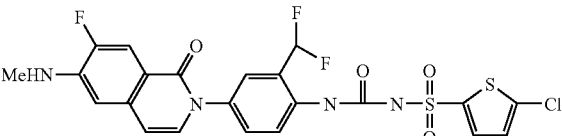
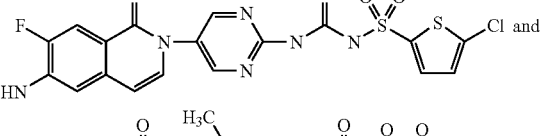
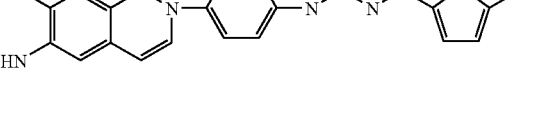

18. A pharmaceutical composition comprising a pharmaceutically acceptable excipient and a compound having the formula:

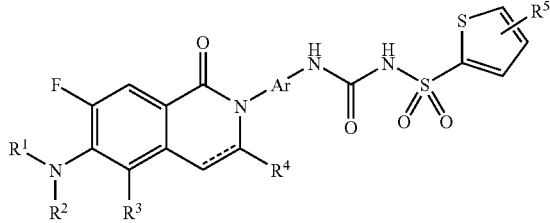

or a pharmaceutically acceptable salt thereof, wherein the dotted line represents an optional double bond;

$R^1$ is a member selected from the group consisting of $C_{1-6}$ alkyl, $C_{1-6}$ haloalkyl, $C_{3-5}$ cycloalkyl, $C_{3-5}$ cycloalkyl-alkyl and benzyl;

$R^2$ is a member selected from the group consisting of H, $C_{1-6}$ alkyl and $C_{1-6}$ haloalkyl;

$R^3$ is a member selected from the group consisting of H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, cyano and —C(O)$R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di-$C_{1-6}$ alkylamino;

$R^4$ is a member selected from the group consisting of H and $C_{1-6}$ alkyl;

$R^5$ is a member selected from the group consisting of H, halogen, $C_{1-6}$ alkyl, $C_{2-6}$ alkenyl, $C_{2-6}$ alkynyl, C-6 haloalkyl, $C_{1-6}$ alkoxy, cyano and —C(O)$R^{5a}$, wherein $R^{5a}$ is a member selected from the group consisting of $C_{1-6}$ alkoxy, amino, $C_{1-6}$ alkylamino and di- C-6 alkylamino; and Ar is an aromatic ring selected from the group consisting of benzene, pyridine and pyrimidine, each of which is optionally substituted with from 1-2 $R^6$ substituents, wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, amino, $C_{1-6}$ alkylamino, di-$C_{1-6}$ alkylamino, —C(O)$R^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_m$N(R$^{6b}$)$_2$, wherein the subscript m is an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di- $C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine or piperidine ring.

19. A pharmaceutical composition of claim 18, wherein said compound has the formula:

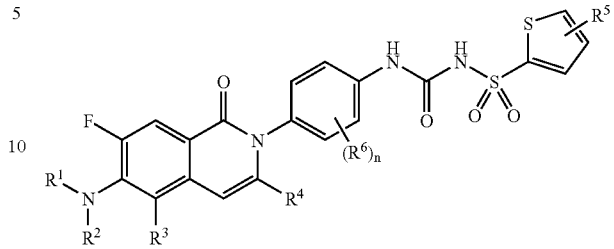

wherein n is 0 or 1; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano and —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

20. A pharmaceutical composition of claim 19, wherein $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or CH$_3$; $R^5$ is chloro and is attached at the 5-position of the thienyl ring; and $R^6$, when present is selected from the group consisting of $C_{1-4}$ alkyl, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

21. A pharmaceutical composition of claim 18, wherein said compound is selected from the group consisting of:

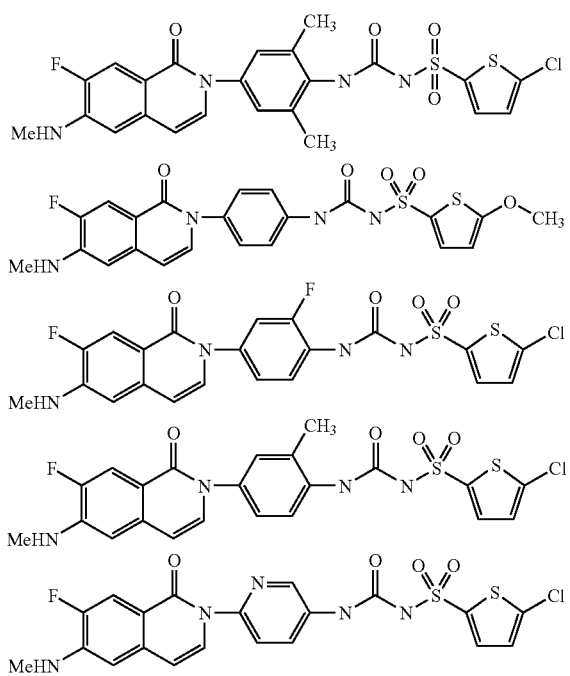

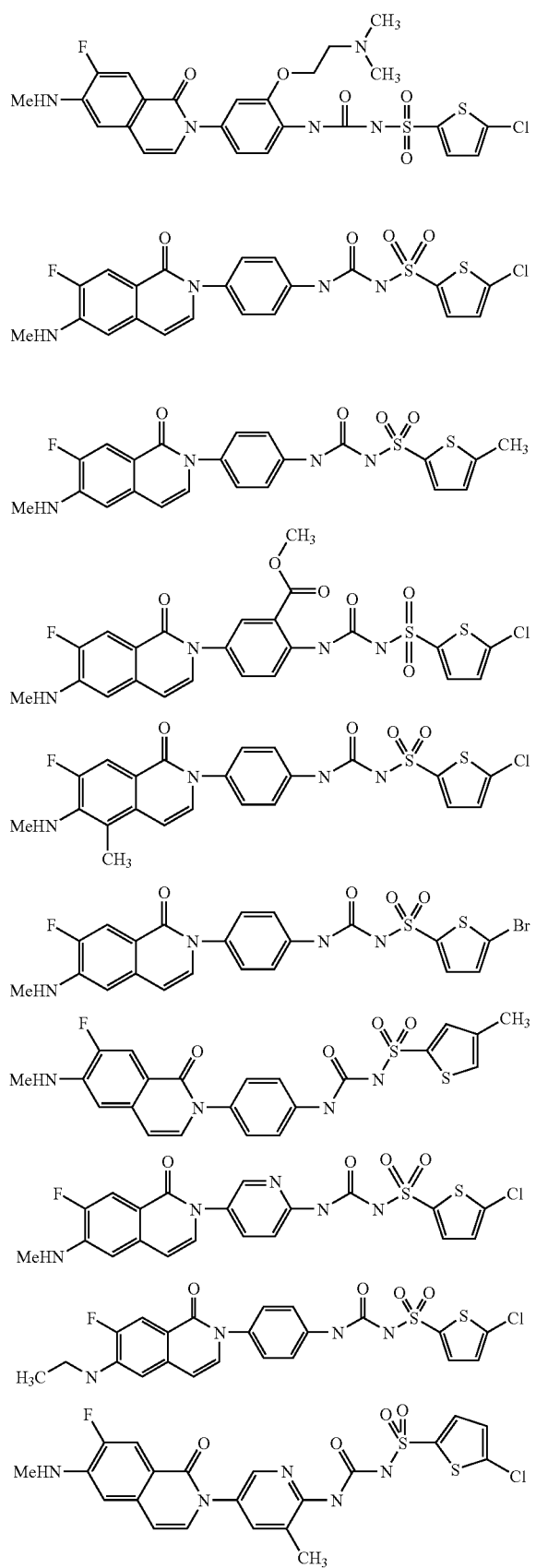
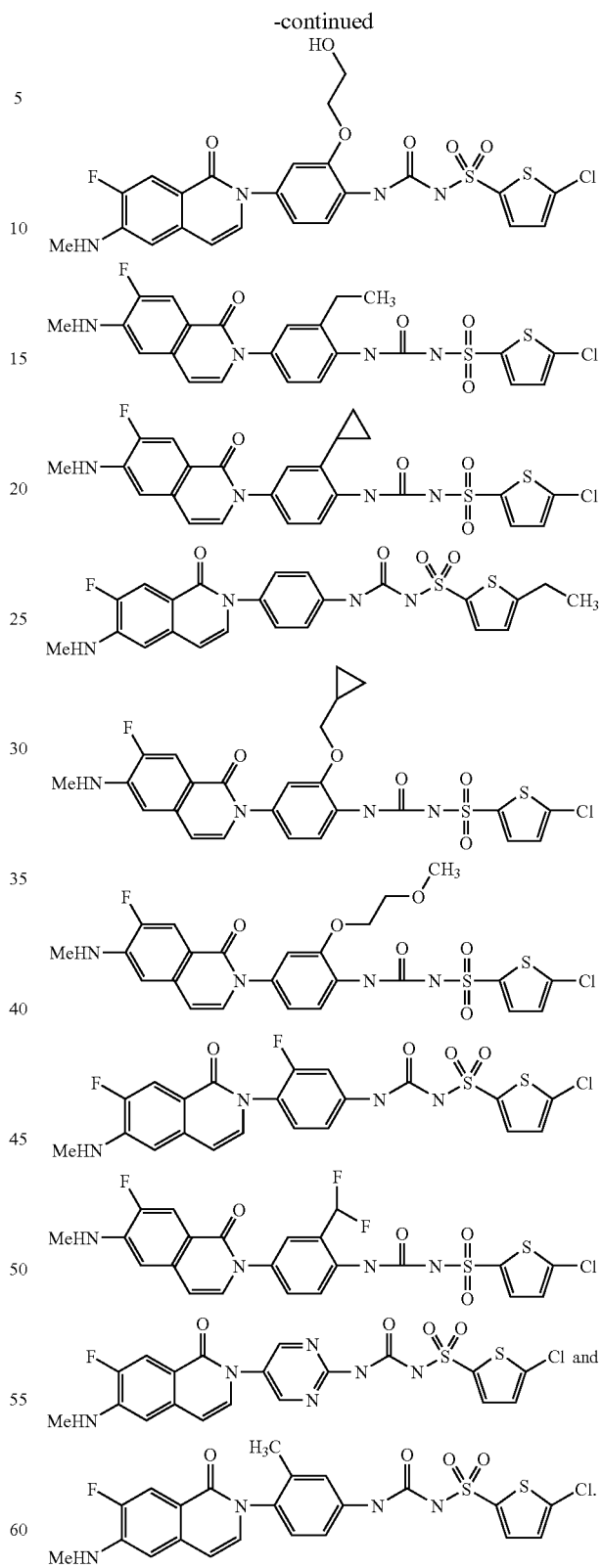
22. A method of treating thrombosis in a subject comprising administering to a subject in need thereof, a therapeutically effective amount of a compound having the formula:

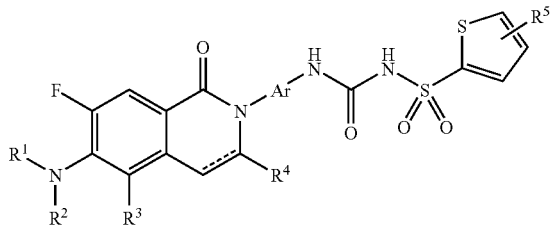

or a pharmaceutically acceptable salt thereof, wherein the dotted line indicates an optional double bond;

$R^1$ is a member selected from the group consisting of $C_{1-6}$ alkyl, $C_{1-6}$ haloalkyl, $C_{3-5}$ cycloalkyl, $C_{3-5}$ cycloalkyl-alkyl and benzyl;

$R^2$ is a member selected from the group consisting of H, $C_{1-6}$ alkyl and $C_{1-6}$ haloalkyl;

$R^3$ is a member selected from the group consisting of H, $C_{1-6}$ alkyl, $C_{2-6}$ alkenyl, $C_{2-6}$ alkynyl, $C_{3-5}$ cycloalkyl, $C_{3-5}$ cycloalkyl-alkyl, $C_{1-6}$ haloalkyl, $C_{1-6}$ hydroxyalkyl, cyano and —C(O)$R^{3a}$, wherein $R^{3a}$ is a member selected from the group consisting of H, hydroxy, $C_{1-6}$ alkyl, $C_{1-6}$ alkoxy, amino, $C_{1-6}$ alkylamino and di- $C_{1-6}$ alkylamino;

$R^4$ is a member selected from the group consisting of H and $C_{1-6}$ alkyl;

$R^5$ is a member selected from the group consisting of H, halogen, $C_{1-6}$ alkyl, $C_{2-6}$ alkenyl, $C_{2-6}$ alkynyl, $C_{1-6}$ haloalkyl, $C_{1-6}$ alkoxy, cyano and —C(O)$R^{5a}$, wherein $R^{5a}$ is a member selected from the group consisting of $C_{1-6}$ alkoxy, amino, $C_{1-6}$ alkylamino and di- $C_{1-6}$ alkylamino; and Ar is an aromatic ring selected from the group consisting of benzene, pyridine and pyrimidine, each of which is optionally substituted with from 1-2 $R^6$ substituents, wherein each $R^6$ is independently selected from the group consisting of halogen, cyano, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, $C_{3-5}$ cycloalkyl, $C_{3-5}$ cycloalkyl-alkyl, $C_{3-5}$ cycloalkyl-alkoxy, amino, $C_{1-6}$ alkylamino, di-$C_{1-6}$ alkylamino, —C(O)$R^{6a}$, —O(CH$_2$)$_m$OR$^{6b}$, —(CH$_2$)$_m$OR$^{6b}$, —O(CH$_2$)$_m$N(R$^{6b}$)$_2$ and —(CH$_2$)$_m$N(R$^{6b}$)$_2$, wherein the subscript m is an integer of from 1 to 3, each $R^{6a}$ is a member independently selected from the group consisting of H, hydroxy, $C_{1-6}$ alkyl, $C_{1-6}$ alkoxy, amino, $C_{1-6}$ alkylamino and di- $C_{1-6}$ alkylamino, and each $R^{6b}$ is a member independently selected from the group consisting of H, $C_{1-4}$ alkyl and $C_{1-4}$ alkanoyl, and optionally, two $R^{6b}$ groups attached to nitrogen are combined with the nitrogen atom to form an azetidine, pyrrolidine or piperidine ring.

23. A method in accordance with claim 22, wherein said compound is administered in combination with a second therapeutic agent selected from the group consisting of antiplatelet compounds, anticoagulants, fibrinolytics, anti-inflammatory compounds, cholesterol-lowering agents, blood pressure-lowering agents and serotonin blockers.

24. A method in accordance with claim 23, wherein said second therapeutic agent is an antiplatelet compound selected from the group consisting of GPIIB-IIIa antagonists, aspirin, phosphodiesterase III inhibitors and thromboxane A2 receptor antoagonists.

25. A method in accordance with claim 23, wherein said second therapeutic agent is an anticoagulant selected from the group consisting of thrombin inhibitors, coumadin, heparin and Lovenox®.

26. A method in accordance with claim 23, wherein said second therapeutic agent is an anti-inflammatory compound selected from the group consisting of non-steroidal anti-inflammatory agents, cyclooxygenase-2 inhibitors and rheumatoid arthritis agents.

27. A method in accordance with claim 23, wherein said compound is administered orally.

28. A method in accordance with claim 22, wherein said compound has the formula:

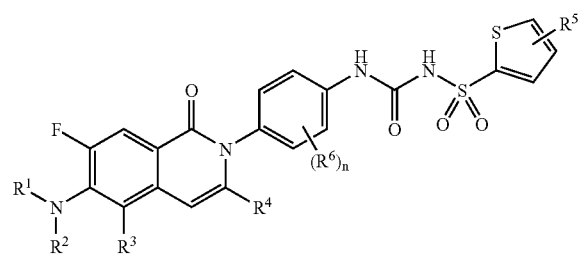

wherein n is 0 or 1; $R^1$ is $C_{1-4}$ alkyl, $C_{3-5}$ cycloalkyl, or $C_{3-5}$ cycloalkyl-alkyl; $R^2$ is H; $R^3$ is H, $C_{1-4}$ alkyl, $C_{2-4}$ alkenyl, $C_{2-4}$ alkynyl, $C_{3-5}$ cycloalkyl, $C_{3-5}$ cycloalkyl-alkyl, $C_{1-4}$ haloalkyl, cyano or —C(O)$R^{3a}$; $R^4$ is H or $C_{1-4}$ alkyl; $R^5$ is halogen, $C_{1-4}$ alkyl, $C_{1-4}$ alkoxy, $C_{1-4}$ haloalkyl, —CN, —C≡CH or —CONH$_2$; and $R^6$, when present is selected from the group consisting of $C_{1-4}$ alkyl, $C_{1-4}$ alkoxy, $C_{3-5}$ cycloalkyl-alkoxy, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

29. A method in accordance with claim 28, wherein $R^1$ is methyl; $R^3$ is H, $C_{1-4}$ alkyl, $C_{2-4}$ alkenyl, $C_{2-4}$ alkynyl, $C_{3-5}$ cycloalkyl or $C_{3-5}$ cycloalkyl-alkyl; $R^4$ is H or CH$_3$; $R^5$ is chloro and is attached at the 5-position of the thienyl ring; and $R^6$, when present is selected from the group consisting of $C_{1-4}$ alkyl, —O(CH$_2$)$_m$OR$^{6b}$ and —O(CH$_2$)$_m$N(R$^{6b}$)$_2$ wherein the subscript m is 1 or 2 and each $R^{6b}$ is independently selected from the group consisting of H, $C_{1-4}$ alkyl and $C_{1-4}$ alkanoyl.

30. A method in accordance with claim 22, wherein said compound is selected from the group consisting of:

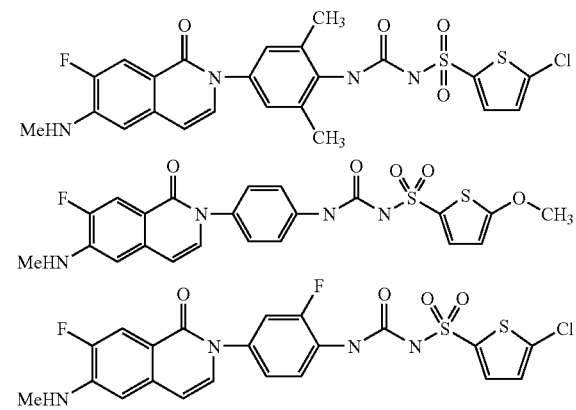

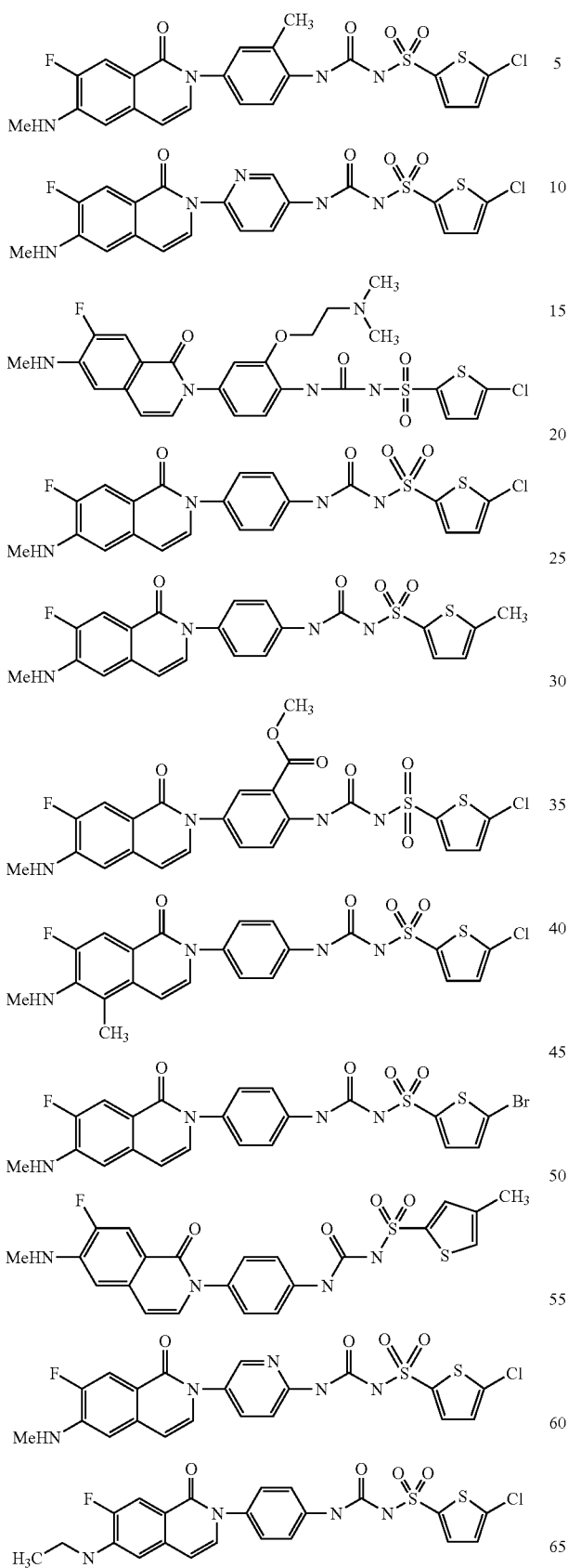
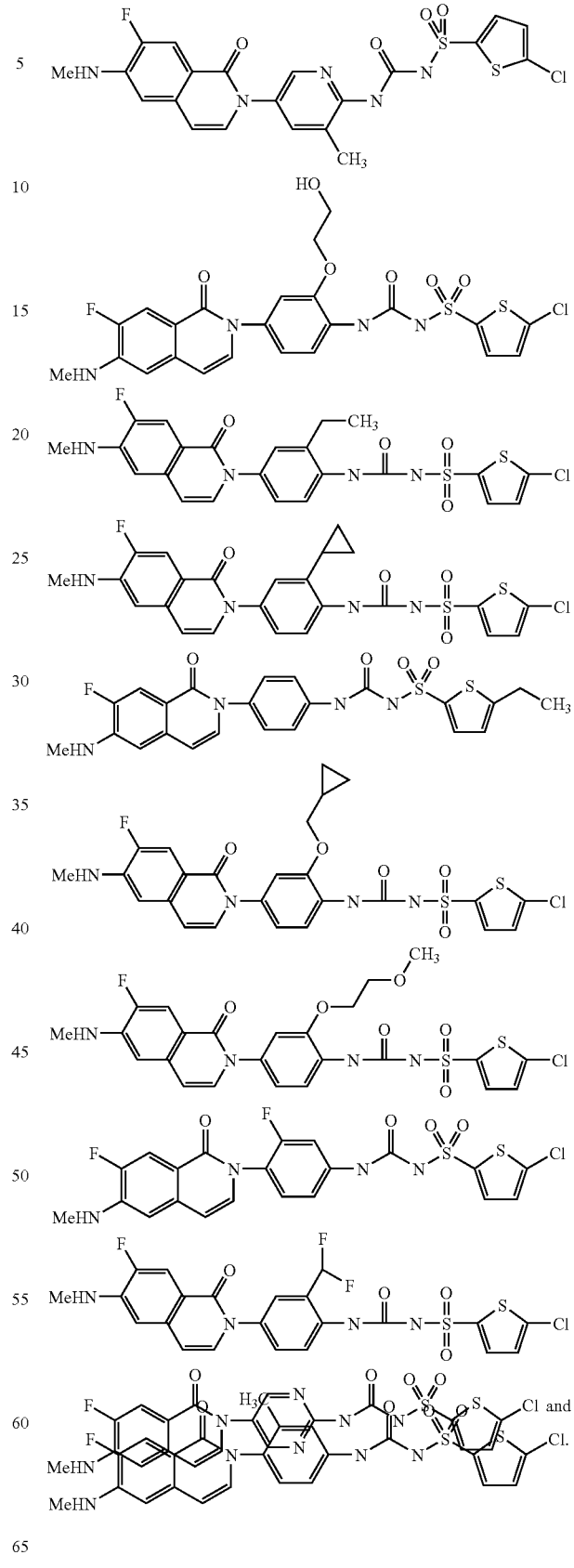
* * * * *